US012734230B2

(12) United States Patent
Livengood et al.

(10) Patent No.: US 12,734,230 B2
(45) **Date of Patent: *Sep. 15, 2026**

(54) COMPOSITIONS AND METHODS FOR STABILIZING FLAVIVIRUSES WITH IMPROVED FORMULATIONS

(71) Applicant: TAKEDA VACCINES, INC., Cambridge, MA (US)

(72) Inventors: Jill Ann Livengood, Fort Collins, CO (US); Linda Marie Strange, Framingham, MA (US); Steven Michael Erb, Fort Collins, CO (US)

(73) Assignee: TAKEDA VACCINES, INC., Cambridge, MA (US)

( * ) Notice: Subject to any disclaimer, the term of this patent is extended or adjusted under 35 U.S.C. 154(b) by 142 days.

This patent is subject to a terminal disclaimer.

(21) Appl. No.: 18/113,193

(22) Filed: Feb. 23, 2023

(65) Prior Publication Data

US 2023/0263880 A1 Aug. 24, 2023

Related U.S. Application Data

(63) Continuation of application No. 17/062,923, filed on Oct. 5, 2020, now Pat. No. 11,701,421, which is a continuation of application No. 16/322,791, filed as application No. PCT/US2017/045375 on Aug. 3, 2017, now Pat. No. 10,835,597.

(60) Provisional application No. 62/370,611, filed on Aug. 3, 2016.

(51) Int. Cl.

| | |
|---|---|
| ***A61K 39/00*** | (2006.01) |
| ***A61K 31/7088*** | (2006.01) |
| ***A61K 38/17*** | (2006.01) |
| ***A61K 39/12*** | (2006.01) |
| ***C12N 7/00*** | (2006.01) |

(52) U.S. Cl.

CPC ................ *A61K 39/12* (2013.01); *C12N 7/00* (2013.01); *A61K 2039/5254* (2013.01); *A61K 2039/55505* (2013.01); *A61K 2039/55511* (2013.01); *A61K 2039/55516* (2013.01); *C12N 2770/24034* (2013.01); *C12N 2770/24134* (2013.01)

(58) Field of Classification Search

CPC .. A61K 2039/5254; A61K 2039/55505; A61K 2039/55511; A61K 2039/55516; A61K 39/12

See application file for complete search history.

(56) References Cited

U.S. PATENT DOCUMENTS

2008/0248551 A1 10/2008 Stinchcomb et al.

FOREIGN PATENT DOCUMENTS

| | | | |
|---|---|---|---|
| AU | 2013260732 | A1 | 12/2013 |
| CN | 104984357 | A | 10/2015 |
| EP | 2143440 | A1 | 1/2010 |
| JP | 2010509226 | A | 3/2010 |
| JP | 2011527300 | A | 10/2011 |
| JP | 2016-041753 | A | 3/2016 |
| WO | 2005/066333 | A1 | 7/2005 |
| WO | 2008/057550 | A2 | 5/2008 |
| WO | 2010003670 | A1 | 1/2010 |
| WO | 2017/179017 | A1 | 10/2017 |

OTHER PUBLICATIONS

O'Neil, et al., "Novel formulations enhance the thermal stability of live-attenuated flavivirus vaccines", Vaccine, vol. 29, pp. 7456-7462, 2011.

Kumru, et al., "Vaccine instability in the cold chain: Mechanisms, analysis and formulation strategies", Biologicals, vol. 42, pp. 237-259, 2014.

International Search Report dated Nov. 15, 2017 issued in corresponding International Application No. PCT/US2017/045375.

Written Opinion of the International Searching Authority dated Nov. 15, 2017 issued in corresponding International Application No. PCT/US2017/045375.

Livengood, et al., "Combining DOE with an empirical approach to improve vaccine formulation development", Engineering Conferences International, ECI Digital Archives, Vaccine Technology VI, Jun. 13, 2016.

*Primary Examiner* — Barry A Chestnut

(74) *Attorney, Agent, or Firm* — Nath, Goldberg & Meyer; Joshua B. Goldberg

(57) ABSTRACT

Embodiments herein relate to compositions and methods for stabilizing Flaviviruses. In certain embodiments, compositions and methods disclosed herein concern stabilizing live, attenuated or unattenuated (e.g. live whole) flaviviruses. Other embodiments relate to compositions and methods for reducing degradation of live, attenuated or unattenuated flaviviruses. Other embodiments relate to improved formulations for prolonging stabilization of live attenuated or unattenuated Flaviviruses during manufacturing, storage, accelerated storage and transport. Yet other embodiments relate to uses of compositions disclosed herein in kits for transportable applications and methods.

29 Claims, 18 Drawing Sheets

LIQUID
LYO
LOG 10 (pfu/0.5mL)
5
4
3
2
1
0
*
*
PF127
MgC12
SUCROSE
SORBITOL
POLYSORBATE 80
EDTA
MANNITOL
METHIONINE
UREA
ALANINE
LACTOSE
MSG
GELATIN
DEXTRAN 40
HSA LYO LOG LOSS
0.4
0.3
0.2
0.1
0.0
-0.1
-0.2
*
*
MANNITOL
SUCROSE
LACTOSE
SORBITOL
UREA
EDTA
METHIONINE
ALANINE
POLYSORBATE 80
GELATIN
HSA
MSG
DEXTRAN 40
PF127
MgC12

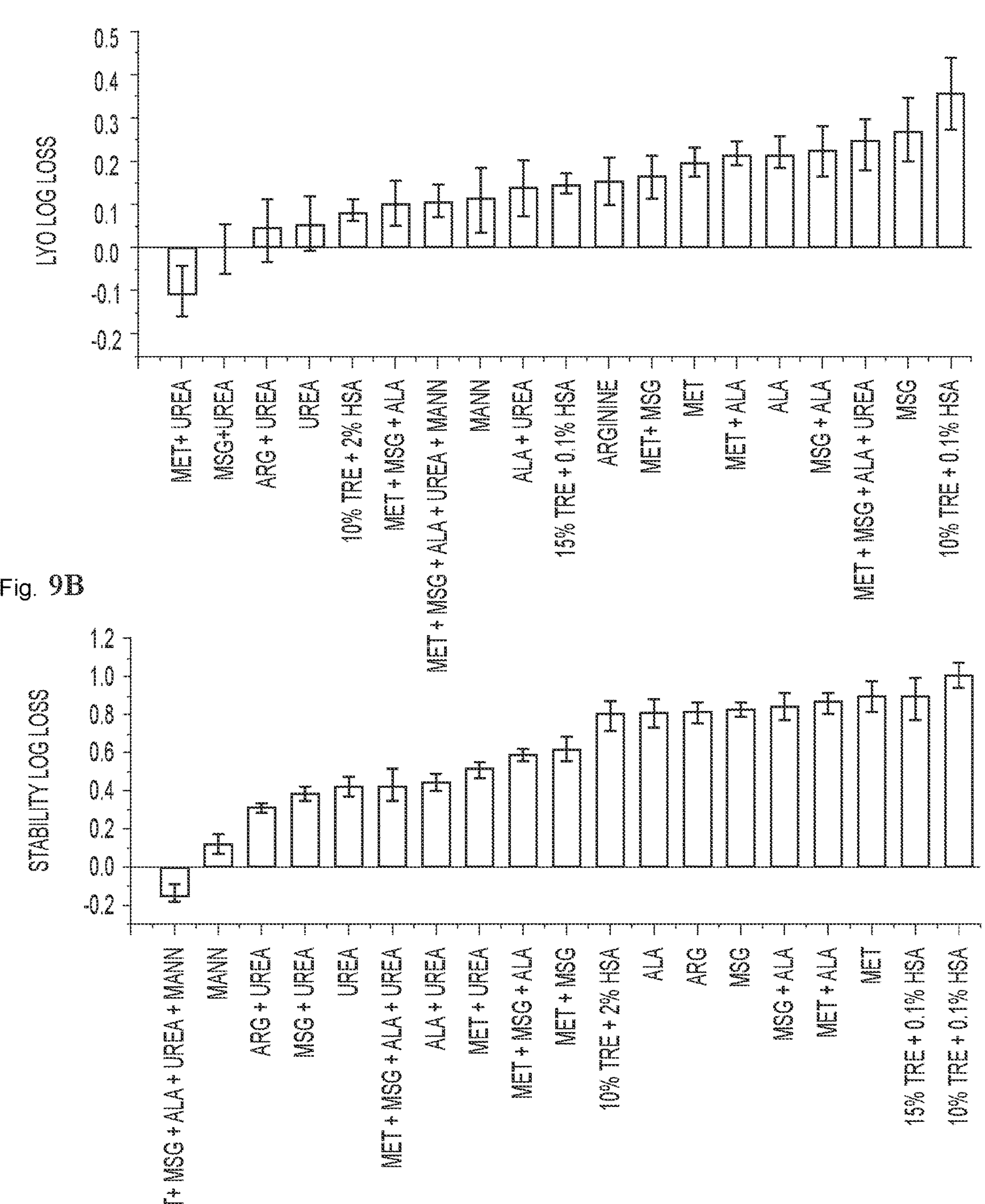
Fig. 9A
LYO LOG LOSS
0.5
0.4
0.3
0.2
0.1
0.0
-0.1
-0.2
MET+ UREA
MSG+UREA
ARG + UREA
UREA
10% TRE + 2% HSA
MET + MSG + ALA
MET + MSG + ALA + UREA + MANN
MANN
ALA + UREA
15% TRE + 0.1% HSA
ARGININE
MET+ MSG
MET
MET + ALA
ALA
MSG + ALA
MET + MSG + ALA + UREA
MSG
10% TRE + 0.1% HSA
Fig. 9B
STABILITY LOG LOSS
1.2
1.0
0.8
0.6
0.4
0.2
0.0
-0.2
MET+ MSG + ALA + UREA + MANN
MANN
ARG + UREA
MSG + UREA
UREA
MET + MSG + ALA + UREA
ALA + UREA
MET + UREA
MET + MSG + ALA
MET + MSG
10% TRE + 2% HSA
ALA
ARG
MSG
MSG + ALA
MET + ALA
MET
15% TRE + 0.1% HSA
10% TRE + 0.1% HSA

11A

| Term | Std Error | t Ratio | Prob>\|t\| |
|---|---|---|---|
| (HSA (%)-0.18986)*(HSA (%)-0.18986) | 0.204587 | -4.18 | 0.0001* |
| HSA (%) | 0.342905 | 4.13 | 0.0001* |
| Urea (%) | 0.136339 | -3.59 | 0.0007* |
| Sucrose % | 0.008072 | -3.47 | 0.0010* |
| Mannitol (%) | 0.07305 | -2.86 | 0.0058* |
| (Mannitol (%)-0.85507)*(Mannitol (%)-0.85507) | 0.022518 | 2.80 | 0.0069* |
| Trehalose % | 0.00811 | -2.56 | 0.0133* |
| Met (mM) | 0.015594 | -1.15 | 0.2546 |
| Ala (mM) | 0.003898 | 0.48 | 0.6298 |
| MSG (mM) | 0.003854 | 0.25 | 0.8004 |

11B

| Term | Std Error | t Ratio | Prob>\|t\| |
|---|---|---|---|
| Urea (%) | 0.165159 | -7.11 | <.0001* |
| Mannitol (%) | 0.01342 | -5.49 | <.0001* |
| (Trehalose %-4.81818)*(Urea (%)-0.07576) | 0.06008 | -3.92 | 0.0003* |
| (Trehalose %-4.81818)*(Mannitol (%)-0.81818) | 0.003985 | -2.95 | 0.0047* |
| (Sucrose %-4.51515)*(Urea (%)-0.07576) | 0.060134 | -2.85 | 0.0062* |
| HSA (%) | 0.438094 | 2.23 | 0.0301* |
| (HSA (%)-0.19848)*(HSA (%)-0.19848) | 0.263223 | -2.13 | 0.0382* |
| Sucrose % | 0.011029 | -1.94 | 0.0584 |
| (Sucrose %-4.51515)*(Mannitol (%)-0.81818) | 0.004138 | -1.80 | 0.0780 |
| Ala (mM) | 0.004622 | -1.05 | 0.2971 |
| Trehalose % | 0.011031 | -1.00 | 0.3208 |
| Met (mM) | 0.018489 | -0.59 | 0.5555 |
| MSG (mM) | 0.004657 | -0.33 | 0.7418 |

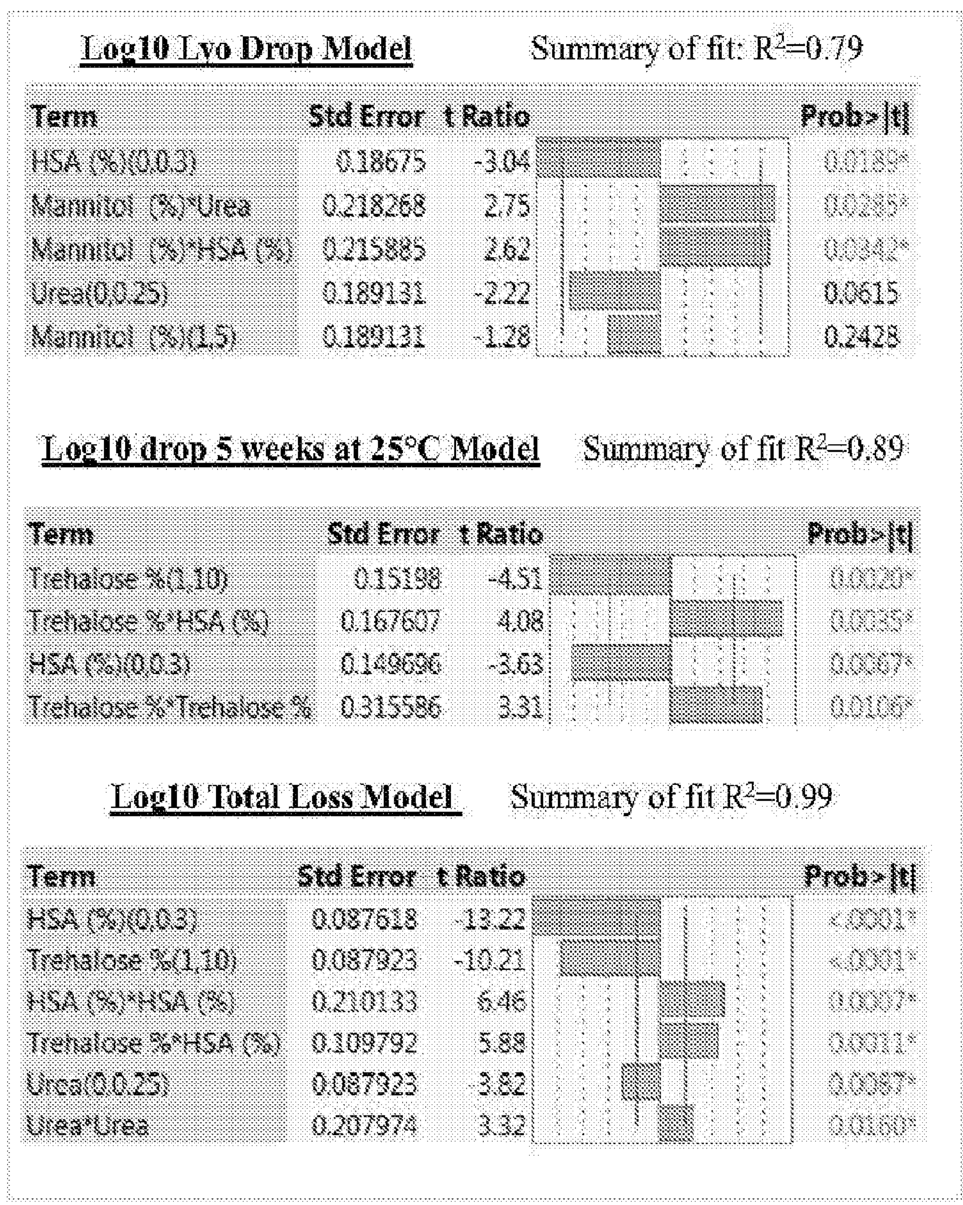

Log10 Lyo Drop Model Summary of fit: $R^2$=0.79

| Term | Std Error | t Ratio | Prob>\|t\| |
|---|---|---|---|
| HSA (%)(0,0.3) | 0.18675 | -3.04 | 0.0189* |
| Mannitol (%)*Urea | 0.218268 | 2.75 | 0.0285* |
| Mannitol (%)*HSA (%) | 0.215885 | 2.62 | 0.0342* |
| Urea(0,0.25) | 0.189131 | -2.22 | 0.0615 |
| Mannitol (%)(1,5) | 0.189131 | -1.28 | 0.2428 |

Log10 drop 5 weeks at 25°C Model Summary of fit $R^2$=0.89

| Term | Std Error | t Ratio | Prob>\|t\| |
|---|---|---|---|
| Trehalose %(1,10) | 0.15198 | -4.51 | 0.0020* |
| Trehalose %*HSA (%) | 0.167607 | 4.08 | 0.0035* |
| HSA (%)(0,0.3) | 0.149696 | -3.63 | 0.0067* |
| Trehalose %*Trehalose % | 0.315586 | 3.31 | 0.0106* |

Log10 Total Loss Model Summary of fit $R^2$=0.99

| Term | Std Error | t Ratio | Prob>\|t\| |
|---|---|---|---|
| HSA (%)(0,0.3) | 0.087618 | -13.22 | <.0001* |
| Trehalose %(1,10) | 0.087923 | -10.21 | <.0001* |
| HSA (%)*HSA (%) | 0.210133 | 6.46 | 0.0007* |
| Trehalose %*HSA (%) | 0.109792 | 5.88 | 0.0011* |
| Urea(0,0.25) | 0.087923 | -3.82 | 0.0087* |
| Urea*Urea | 0.207974 | 3.32 | 0.0160* |

FIG. 12C

13A
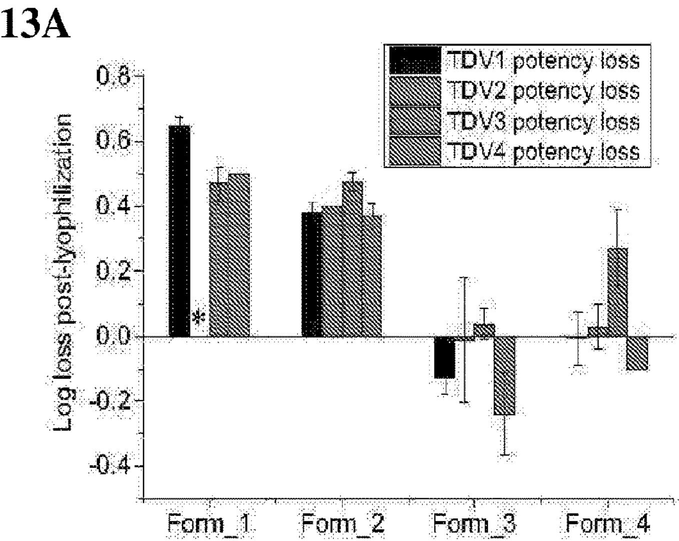
13B
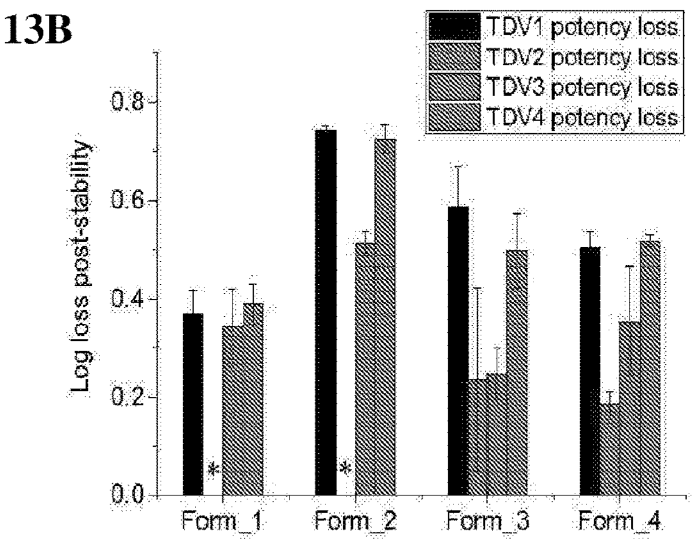
13C
FIGS. 13A-13C
(d)
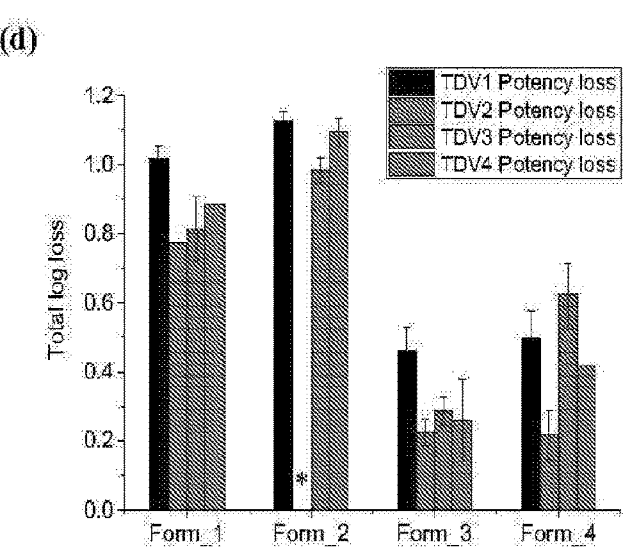

|  | TDV-1 | TDV-2 | TDV-3 | TDV-4 |
|---|---|---|---|---|
| Pre-Lyo | 4.06 | 3.16 | 4.60 | 5.15 |
| Post-Lyo (T0) | 3.41 | 2.52 | 4.14 | 4.66 |
| Pred. 78 wks | 4.32 | 2.95 | 4.90 | 5.62 |

|  | TDV-1 | TDV-2 | TDV-3 | TDV-4 |
|---|---|---|---|---|
| Pre-Lyo | 4.03 | 3.09 | 4.62 | 5.15 |
| Post-Lyo (T0) | 3.65 | 2.69 | 4.14 | 4.78 |
| Pred. 78 wks | 3.36 | 2.78 | 3.89 | 4.57 |

14C

| | TDV-1 | TDV-2 | TDV-3 | TDV-4 |
|---|---|---|---|---|
| Pre-Lyo | 4.07 | 3.16 | 4.61 | 4.89 |
| Post-Lyo (T0) | 4.20 | 3.21 | 4.57 | 5.19 |
| Pred. 78 wks | 3.98 | 2.90 | 4.97 | 5.34 |

14D

| | TDV-1 | TDV-2 | TDV-3 | TDV-4 |
|---|---|---|---|---|
| Pre-Lyo | 4.10 | 3.22 | 4.92 | 5.10 |
| Post-Lyo (T0) | 4.10 | 3.33 | 4.59 | 5.27 |
| Pred. 78 wks | 4.30 | 3.05 | 4.81 | 5.39 |

15A

15B

COMPOSITIONS AND METHODS FOR STABILIZING FLAVIVIRUSES WITH IMPROVED FORMULATIONS

PRIORITY

This is a Continuation Application of U.S. patent application Ser. No. 17/062,923, filed Oct. 5, 2020, an application which is a Continuation of U.S. patent application Ser. No. 16/322,791, filed Feb. 1, 2019, an application filed as a national stage under 371 of Application No. PCT/US2017/045375 filed Aug. 3, 2017 and claiming benefit from provisional U.S. application No. 62/370,611, filed on Aug. 3, 2016, the contents of each of which are hereby incorporated by reference in their entirety.

FIELD

Embodiments herein relate to compositions and methods for stabilizing flaviviruses. In certain embodiments, compositions and methods disclosed herein concern stabilizing live, attenuated or unattenuated (e.g. live whole) flaviviruses. Other embodiments relate to compositions and methods for reducing degradation of live, attenuated or unattenuated flaviviruses. Other embodiments relate to improved formulations for prolonging stabilization of live attenuated or unattenuated flaviviruses during manufacturing, storage, accelerated storage, transport and delivery. Yet other embodiments relate to uses of compositions disclosed herein in kits for transportable applications and administration methods.

BACKGROUND

Vaccines and vaccine formulations have been shown to be important for protecting humans and animals from the detrimental effects of a wide variety of diseases, such as those caused by viruses. One of the most successful prophylactic technologies for viral vaccines is to immunize animals or humans with a weakened or attenuated strain of the virus (a "live, attenuated virus"). Appropriately attenuated viral strains that are part of immunogenic compositions exhibit limited replication after immunization, and therefore, do not give rise to disease. However, the limited viral replication of the attenuated virus is sufficient to express the full repertoire of viral antigens and generates potent and long-lasting immune responses to the virus. Thus, upon subsequent exposure to a pathogenic strain of the virus, the immunized subject has a reduced chance of developing disease. These live, attenuated viral vaccines are among the most successful vaccines used in public health.

In order for live, attenuated viral vaccines to be effective, they must be capable of replicating after immunization, and the viruses themselves must be protected from degradation during preparation as well as transport prior to administration to a subject, in order to ensure for example, that the correct dosage concentration is delivered to the subject. Some vaccines are sensitive to temperature extremes; either excessive heat or accidental freezing can inactivate the vaccine. Maintaining this "cold chain" throughout distribution is particularly difficult in the developing world. Therefore, there remains a need for improving the stability of both existing and newly developed live, attenuated viruses and live viruses in order to improve manufacturing of vaccines, as well as, transport and delivery of the formulations.

SUMMARY

Embodiments herein relate to compositions and methods for stabilizing live flaviviruses. In certain embodiments, compositions and methods disclosed herein concern stabilizing live, attenuated or unattenuated whole flaviviruses. Other embodiments relate to compositions and methods for reducing degradation of live, attenuated or unattenuated flaviviruses. Yet other embodiments relate to improved formulations for prolonging stabilization of live attenuated or unattenuated flaviviruses during manufacturing (e.g. vaccines or anti-viral treatments), storage, transport and administration to a subject. Yet other embodiments relate to uses of compositions or formulations disclosed herein in kits for transportable applications and methods.

Embodiments herein relate to formulations for stabilizing live viruses that can include one or more live flaviviruses, one or more carbohydrate agents, and one or more amino acids or salts, esters or amide derivatives thereof. In accordance with these embodiments, formulations of use herein stabilize live flaviviruses. In other embodiments, formulations of use herein stabilize live flaviviruses for commercial use.

In certain embodiments, formulations disclosed herein can include, but are not limited to, formulations for stabilizing flaviviruses. Flaviviruses can include, but are not limited to, dengue virus, West Nile virus, tick-borne encephalitis virus, yellow fever virus, Japanese encephalitis virus, Kunjin virus, St. Louis encephalitis virus, Murray Valley encephalitis virus, Zika virus, or any related virus thereof.

In some embodiments, formulations disclosed herein can further include a buffer. In accordance with these embodiments, the buffer can include, but is not limited to, phosphate buffered saline (PBS), TRIS buffer, HEPES buffer or the like. In accordance with these embodiments, the buffer can include at least one salt of sodium chloride (NaCl), monosodium and/or disodium phosphate ($Na_2HPO_4$), potassium chloride (KCl), and potassium phosphate ($KH_2PO_4$). In some embodiments, the buffer of formulations disclosed herein can include sodium chloride (NaCl) having a concentration of about 10.0 mM to about 200.0 mM. In other embodiments, formulations for stabilizing live or live, attenuated flaviviruses do not contain magnesium chloride ($MgCl_2$).

In certain embodiments, formulations disclosed herein can further include one or more protein agents. In accordance with these embodiments, the one or more protein agents can include, but is not limited to, albumin, gelatin and/or dextran. For example, the albumin can include, but is not limited to, a recombinant albumin, a native albumin, human serum albumin (HSA), recombinant human serum albumin (rHSA), native human serum albumin (nHSA), or an albumin-like agent. In other embodiments, the one or more protein agents in the composition can include, but are not limited to, any serum albumin, a human serum albumin (HSA), a bovine serum albumin (BSA), any comparable mammalian serum, gelatin, dextran, a polyol polymer, or combinations thereof. In accordance with these embodiments, one or more protein agents in a formulation disclosed herein can include albumin, such as human serum albumin or recombinant albumin having a concentration of about 0.01% to about 2.0% (w/v). In one embodiment, a formulation disclosed herein can include human serum albumin (HSA) having a concentration of about 0.01% to about 2.0% (w/v).

In other embodiments, the one or more carbohydrate agents of formulations disclosed herein can include, but are not limited to, trehalose (e.g. D-trehalose dehydrate), galactose, fructose, lactose, sucrose, chitosan, mannitol or combinations thereof. In accordance with these embodiments, the one or more carbohydrate agent concentration can be from about 0.5% to about 15.0% (w/v). In certain embodiments, the one or more carbohydrate agents in a formulation disclosed herein can include trehalose and/or sucrose. In other embodiments, the one or more carbohydrate agents in a formulation disclosed herein can include mannitol in combination with at least one of trehalose and sucrose. In other embodiments, the one or more carbohydrate agents in the composition can include mannitol in combination with both trehalose and sucrose. In certain embodiments, formulations disclosed herein do not include sorbitol. In other embodiments, some formulations disclosed herein do not contain poloxamer 407 or other poloxamer.

In some embodiments, the one or more amino acids in a formulation can include, but are not limited to, alanine, arginine, methionine, or combinations thereof. In certain embodiments, one or more amino acids can include an amino acid derivative or salt thereof. In yet other embodiments, an amino acid derivative can include monosodium glutamate (MSG) or potassium glutamate. In certain embodiments, the one or more amino acids or derivatives thereof are present in a formulation at a concentration of about 0.5 mM to about 150.0 mM.

In some embodiments, formulations disclosed herein can include one or more osmolytes. In accordance with these embodiments, one or more osmolytes can include urea (for example a carbamide) or other substitutable agent, for example, caprolactam, PEG 400 or PEG 600. In accordance with these embodiments, the one or more osmolyte concentration (e.g. urea) can be about 0.01% to about 0.5% (w/v).

In certain embodiments, formulations disclosed herein can include sucrose and/or trehalose in a buffer and urea. In other embodiments, the formulation can further include one or more amino acids. In certain embodiments, the one or more amino acids can include at least one of alanine and methionine. In accordance with these embodiments, these formulations can further include at least one of mannitol and MSG. In certain embodiments, a formulation can include trehalose and mannitol in a buffer without urea or amino acids. In accordance with these embodiments, the buffer can include PBS (or TRIS, HEPES or other suitable buffer), NaCl and albumin (e.g., HSA).

In some embodiments, a formulation can include a base buffer, sucrose, albumin, mannitol, alanine, methionine, MSG and/or urea in any combination. In accordance with these embodiments, certain formulations can include recombinant HSA having a concentration of about 0.01% to about 2.0% (w/v), sucrose concentration having a concentration of about 1.0% to about 15.0% (w/v), mannitol concentration having a concentration of about 0.1% to about 15.0% (w/v), alanine having a concentration of about 0.5 mM to about 100 mM, methionine concentration having a concentration of about 1.0 mM to 5.0 mM, MSG concentration having a concentration of about 1.0 mM to about 50.0 mM, and urea concentration having a concentration of about 0.05% to about 1.0% (w/v).

In some embodiments, formulations contemplated herein can include recombinant albumin or HSA, trehalose and/or sucrose in a base buffer, mannitol, alanine, methionine, MSG and urea.

In some embodiments, recombinant HSA concentration can be about 0.01% to about 2.0% (w/v), trehalose concentration can be about 1.0% to about 10.0% (w/v), sucrose concentration can be about 1.0% to about 15.0% (w/v), mannitol concentration can be about 0.1% to about 15.0% (w/v), alanine can be about 0.5 mM to about 100 mM, methionine concentration can be about 1.0 mM to 5.0 mM, MSG concentration can be about 5.0 mM to about 100.0 mM, and urea concentration can be about 0.05% to about 1.0% (w/v).

In some embodiments, formulations can include recombinant HSA, sucrose, alanine and urea. In other embodiments, recombinant HSA concentration can be about 0.01% to about 0.2%, sucrose can be a concentration can be about 1.0% to about 15.0% (w/v), alanine can be about 0.5 mM to about 100 mM, and urea concentration can be about 0.05% to about 1.0% (w/v). In certain embodiments regarding this paragraph, sucrose can be replaced with trehalose at a concentration of about 1.0% to about 10% (w/v).

In some embodiments, stabilizing one or more live flaviviruses can include reducing loss or reducing degradation of the one or more live flaviviruses upon freezing, freeze drying, at refrigeration temperatures, at room temperature and at about 25° C., as compared to a composition not containing one or more of these agents. In some embodiments, stabilizing one or more live flaviviruses as contemplated herein can include obtaining a 10%, a 20%, a 30%, a 40% or a 50% or more reduction in loss or degradation of the live or live, attenuated flaviviruses.

In some embodiments, methods disclosed herein can include partially or wholly dehydrating the formulation that includes the live flavivirus. In other embodiments, methods can include partially or wholly rehydrating the formulation that includes the live or live, attenuated flaviviruses prior to administration to a subject as part of an immunogenic composition (e.g. vaccine composition). In yet other embodiments, methods can include freezing live or live, attenuated flavivirus compositions disclosed herein.

Other embodiments relate to kits for stabilizing live or live, attenuated flaviviruses. In accordance with these embodiments, kits can include any composition or formulation disclosed herein and at least one container.

Certain embodiments concern live, attenuated flavivirus compositions disclosed herein and methods directed to manufacturing an immunogenic composition (e.g. a vaccine) capable of reducing or preventing onset of a medical condition such as an infection or disease caused by one or more of the flaviviruses. In certain embodiments, one or more live, attenuated flaviviruses can be part of a pharmaceutical composition that can include a pharmaceutically acceptable excipient or carrier. In accordance with these embodiments, the pharmaceutical composition can be administered to a subject in order to reduce onset of a condition caused by a flavivirus infection when administered to a subject, and/or prepared for administration to a subject. A subject can be a mammal for example, a domesticated animal a pet, livestock, other animal or a human subject (e.g. an adult, adolescent or child).

In some embodiments, compositions can include recombinant HSA or HSA, sucrose, methionine and urea. In accordance with these embodiments, recombinant HSA or HSA can have a concentration ranging from about 0.01% to about 2.0% (w/v), sucrose can have a concentration ranging from about 0.5% to about 10.0% (w/v), methionine can have a concentration ranging from about 1.0 mM to about 5.0 mM, and urea can have a concentration ranging from about 0.05% to about 0.5% (w/v). In other embodiments, a formulation having recombinant HSA or HSA, sucrose, methionine and urea can further include one or more of alanine at about 5.0 mM to about 25.0 mM, mannitol at about 1.0% to about 15% (w/v) and monosodium glutamate (MSG) at about 1.0 mM to about 20.0 mM. In certain embodiments, the compositions can be in a sucrose base buffer disclosed herein. In yet other embodiments, sucrose can be replaced with trehalose in these compositions.

In other embodiments, a composition can include recombinant HSA, sucrose and/or trehalose, arginine and urea. In accordance with these embodiments, recombinant HSA or HSA can have a concentration ranging from about 0.05% to about 0.5% (w/v), sucrose and/or trehalose can have a concentration ranging from about 0.5% to about 10.0% (w/v), arginine can have a concentration ranging from about 1.0 mM to about 50.0 mM, and urea can have a concentration ranging from about 0.01% to about 0.5% (w/v).

In some embodiments, a composition can include recombinant HSA, sucrose and/or trehalose, MSG (monosodium glutamate) and urea. In accordance with these embodiments, recombinant HSA or HSA can have a concentration ranging from about 0.05% to about 2.0% (w/v), sucrose and/or trehalose can have a concentration ranging from about 0.5% to about 10.0% (w/v), MSG can have a concentration ranging from about 1.0 mM to about 20.0 mM and urea can have a concentration ranging from about 0.01% to about 0.5% (w/v).

In some embodiments, compositions and methods disclosed herein can include combining one or more live or live, attenuated flaviviruses with a formulation that includes one or more carbohydrate agents and one or more amino acids or salts, esters or amide derivatives thereof. In accordance with these methods, formulations disclosed herein can stabilize one or more live or live, attenuated flaviviruses from degradation. Formulations disclosed herein are capable of stabilizing for example any serotype or strain of flavivirus. In certain embodiments, flaviviruses include enveloped viruses, for example, dengue virus (e.g. serotypes 1-4), yellow fever virus, West Nile virus and Zika virus.

BRIEF DESCRIPTION OF THE DRAWINGS

The following drawings form part of the instant specification and are included to further demonstrate certain aspects of some embodiments disclosed herein. Certain embodiments may be better understood by reference to one or more of these drawings in combination with the detailed description presented herein.

FIGS. 9A-9B represent exemplary graphs illustrating effects of single excipients and excipient combinations (in a base buffer containing trehalose) regarding a flavivirus viral potency in both liquid and lyophilized forms, lyophilized log loss (9A) and stability loss (9B) in one embodiment disclosed herein.

FIGS. 11A-11B are exemplary summaries of excipient screening data sets on flaviviruses potency losses, in one embodiment disclosed herein.

FIGS. 12A-12C are exemplary bar graphs illustrating Definitive Screening Design (DSD) design of experiments formulations for a flavivirus formulated for titer in liquid, lyophilized (stored at −80° C.) and overall stability (12A) and stability trend (12B) of the samples for transport (lyophilized formulation stored at 25° C.) and log drop under the various conditions tested (12C), in some embodiments disclosed herein.

FIGS. 13A-13C are exemplary bar graphs representing flavivirus serotypes (in a tetravalent immunogenic composition) regarding formulation design and viral titer losses, in some embodiments disclosed herein.

DESCRIPTION OF ILLUSTRATIVE EMBODIMENTS

Definitions

Figure 1:
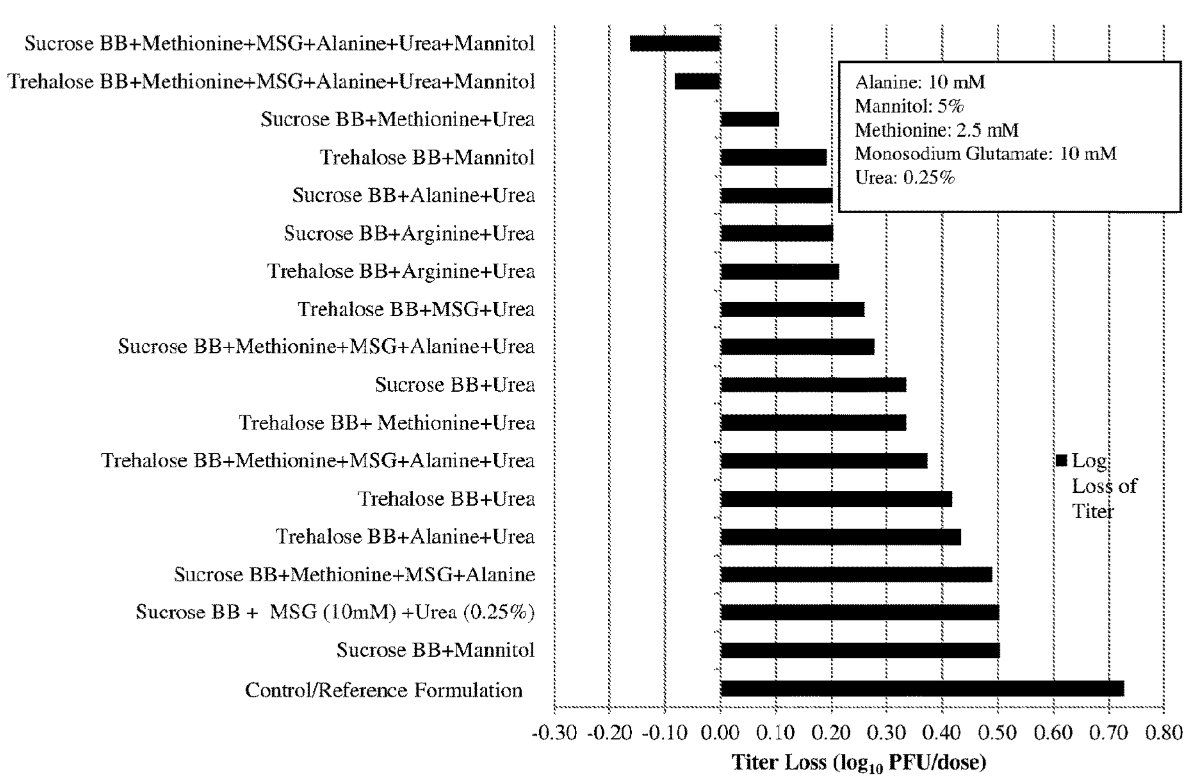
FIG. 1 represents an exemplary histogram plot illustrating data obtained from experiments performed while analyzing stability of live flaviviruses in various formulations, according to some embodiments disclosed herein.

As used herein, “a” or “an” can mean one or more than one of an item, component or element.

As used herein, "about" can mean up to and including plus or minus five percent, for example, about 100 mM can mean 95 mM and up to 105 mM.

As used herein "TDV" refers to exemplary dengue viruses (e.g. a live, attenuated dengue virus serotype, TDV-1, dengue-dengue chimeras, dengue chimera with a dengue-2 backbone (e.g. dengue-2 PDK-53 or modified version thereof with at least 95% homology to PDK-53 etc.).

As used herein "DMEM" can mean Dulbecco's modified minimal essential medium.

As used herein "PBS" can mean Phosphate Buffered Saline.

As used herein "FBS" can mean Fetal Bovine Serum.

As used herein "HSA" can mean Human Serum Albumin.

As used herein "Lyo" can mean lyophilized or dehydrated depending on the frame of reference.

As used herein the specification, "subject" or "subjects" can include, but are not limited to, mammals such as humans (e.g. adult, adolescents, young children or infant) or mammals, domesticated or wild, for example dogs, cats, other household pets (e.g., hamster, guinea pig, mouse, rat), ferrets, rabbits, pigs, goats, horses, cattle, other livestock, prairie dogs, wild rodents, or zoo animals.

As used herein, the terms "virus chimera," "chimeric virus," "flavivirus chimera" and "chimeric flavivirus" can mean a chimera having at least 2 different viruses represented in a construct for example a construct of a flavivirus chimera has 2 different flaviviruses represented by including non-structural and structural elements from each of flavivirus. Examples of flavivirus chimeras can include, but are not limited to, dengue virus, West Nile virus, Japanese encephalitis virus, St. Louis encephalitis virus, tick-borne encephalitis virus, yellow fever virus, Zika virus and any combination thereof. For example, a dengue-dengue, dengue-Zika, or a yellow-fever/dengue chimera is contemplated.

As used herein, the term "dengue-dengue chimera" can mean at least two different dengue virus serotypes make up the dengue-dengue chimera.

As used herein, "nucleic acid chimera" can mean a construct of the present disclosure including a nucleic acid sequence from at least two different viruses for example, a chimeric flavivirus or a dengue-dengue chimera disclosed herein can be a nucleic acid chimera.

As used herein, "a live flavivirus" can mean a wild-type live flavivirus (e.g. for use in manufacturing live, attenuated flaviviruses). "Live, attenuated flavivirus" can mean a live flavivirus having a mutation, a flavivirus chimera or other selected for traits where the virus has reduced to no infectivity and reduced expansion or is unable to be transmitted from one host to another (e.g. via mosquito) and is of use in manufacturing immunogenic compositions and where other traits can include reduced virulence, increased safety, increased efficacy or improved growth, etc.

DETAILED DESCRIPTION

In the following sections, various exemplary compositions and methods are described in order to detail various embodiments. It will be obvious to one of skill in the relevant art that practicing the various embodiments does not require employment of all or even some of the specific details outlined herein, but rather that concentrations, times and other specific details may be modified through routine experimentation. In some embodiments, well known methods or components have not been included in the description.

In certain embodiments, stability of live flaviviruses of use in immunogenic or vaccine formulations have been studied in various formulations disclosed herein. In certain embodiments, formulations which increases flavivirus stability to reduce loss of titer of liquid, frozen, lyophilized, partially lyophilized and re-hydrated live flavivirus formulations has been demonstrated.

In some embodiments, formulations disclosed herein can include, but are not limited to, formulations for stabilizing flaviviruses. Flaviviruses can include, but are not limited to, dengue virus, West Nile virus, tick-borne encephalitis virus, yellow fever virus, Japanese encephalitis virus, Kunjin virus, St. Louis encephalitis virus, Murray Valley encephalitis virus, Zika virus, or any related virus thereof.

In some embodiments, formulations disclosed herein can include a buffer. In accordance with these embodiments, the buffer can include, but is not limited to, phosphate buffered saline (PBS), Histidine, TRIS, 2-[4-(2-hydroxyethyl) piperazin-1-yl]ethanesulfonic acid (HEPES) or similar buffer. In accordance with these embodiments, the buffer can include a salt of sodium chloride (NaCl), monosodium and/or disodium phosphate ($Na_2HPO_4$), potassium chloride (KCl), and potassium phosphate ($KH_2PO_4$) or combination thereof. In some embodiments, the buffer of formulations disclosed herein can include NaCl, monosodium and/or disodium phosphate ($Na_2HPO_4$), potassium chloride (KCl), and potassium phosphate ($KH_2PO_4$) or combination thereof having a concentration of about 10.0 mM to about 200.0 mM; or about 10 mM to about 150 mM; or about 15 mM to about 75 mM or about 15 mM to about 50 mM. In other embodiments, formulations for stabilizing live flaviviruses do not contain magnesium chloride ($MgCl_2$).

In certain embodiments, formulations disclosed herein can further include one or more protein agents. In accordance with these embodiments, the one or more protein agents can include, but is not limited to, albumin, gelatin and/or dextran. For example, the albumin can include, but is not limited to, a recombinant albumin, a native albumin, human serum albumin (HSA) or an albumin-like agent. In other embodiments, the one or more protein agents in the composition can include, but is not limited to, any serum albumin, a human serum albumin (HSA), a bovine serum albumin (BSA), any comparable mammalian serum, gelatin, dextran, a polyol polymer, or combinations thereof.

In some embodiments, one or more protein agents in a formulation disclosed herein can include albumin, such as human serum albumin or recombinant albumin, having a concentration of about 0.01% to about 2.0% (w/v); or about 0.05% to about 1.0% (w/v); or 0.05% to about 0.5% (w/v); or 0.075% to 0.2% (w/v); or 0.1% to 0.3% (w/v). In accordance with these embodiments, any formulation disclosed herein can include human serum albumin (HSA) having a concentration of about 0.01% to about 2.0%.

In other embodiments, the one or more carbohydrate agents of formulations disclosed herein can include, but are not limited to, trehalose, galactose, fructose, lactose, sucrose, chitosan, mannitol or combinations thereof. In accordance with these embodiments, the one or more carbohydrate agent concentration can be from about 0.5% to about 15.0% (w/v); or about 1.0% to about 10% or about 5.0% to about 8.0%. In certain embodiments, the one or more carbohydrate agents in the composition can include trehalose and/or sucrose. In other embodiments, the one or more carbohydrate agents in the composition can include mannitol in combination with at least one of trehalose and sucrose. In yet other embodiments, the one or more carbohydrate agents in the composition can include mannitol in combination with both trehalose and sucrose. In certain embodiments, the one or more carbohydrate agents of the formulations disclosed herein have 10% (w/v) or less carbohydrate concentration. In other embodiments, the one or more carbohydrate agents of the formulations disclosed herein have less than 10% (w/v) carbohydrate concentration. In certain embodiments, the formulations disclosed herein do not include sorbitol. In other embodiments, formulations disclosed herein do not contain poloxamer 407 or other poloxamer.

In some embodiments, the one or more amino acids in a formulation can include, but are not limited to, alanine, arginine, methionine, or combinations thereof. In certain embodiments, one or more amino acids can include an amino acid derivative or salt thereof. In yet other embodiments, an amino acid derivative can include monosodium glutamate (MSG) or potassium glutamate. In certain embodiments, the one or more amino acids or derivatives thereof are present in a formulation at a concentration of about 0.5 mM to about 150.0 mM; or about 0.5 mM to 100 mM; or about 1 mM to about 50 mM or about 1.0 mM to about 15.0 mM or about 2.5 mM to 10 mM.

In some embodiments, formulations disclosed herein can include one or more osmolytes. In accordance with these embodiments, one or more osmolytes can include urea (for example a carbamide) or other substitutable agent, for example, caprolactam, PEG 400 or PEG 600. In accordance with these embodiments, the one or more osmolyte concentration can be about 0.01% to about 1.0% (w/v); or about 0.01% to about 0.5% (w/v); or about 0.05% to about 0.5% (w/v) or about 0.075% to about 0.4% (w/v) or about 0.125% (w/v).

In certain embodiments, formulations disclosed herein can further include, sucrose or trehalose, one or more amino acids and urea. In accordance with these embodiments, these formulations can further include at least one of mannitol, MSG and urea. In certain embodiments, a formulation can include trehalose in a suitable buffer and mannitol in a buffer. In accordance with these embodiments, the buffer can include PBS or TRIS or HEPES or other suitable buffer, NaCl and albumin (e.g., HSA). In certain embodiments, the buffer is PBS or HEPES. In certain embodiments, the one or more amino acids can include alanine and/or methionine. In other embodiments a formulation can include sucrose in a suitable buffer and urea.

In certain embodiments, flavivirus formulations can include, but are not limited to, one or more live flaviviruses, buffer, one or more amino acids, and one or more carbohydrate agents. For example, immunogenic compositions and vaccine formulations disclosed herein can include buffers having concentrations of about 1.0 to 30.0 mM Phosphate Buffer, about 1.0 to 30.0 HEPES Buffer, about 1.0 to 30.0 Histidine Buffer, about 1.0 to 30.0 Tris Buffer, with or without salt and trehalose, sucrose or a combination of trehalose and sucrose. Other exemplary immunogenic compositions or vaccine formulations can include about 1.0 to 30.0 mM Phosphate Buffered Saline (PBS) with about 10.0 to about 100 mM sodium chloride at a pH of about 7.2, See Table 1 below.

TABLE 1

Exemplary formulations of immunogenic compositions

| No | Sugar | Buffer | NaCl |
|---|---|---|---|
| 1 | Trehalose (10%) + | 10 mM Phosphate Buffer (pH: 7.2) | — |
| 2 | 0.1% HSA | 10 mM Phosphate Buffer (pH: 7.2) | 50 mM |
| 3 | | 10 mM HEPES Buffer (pH: 7.2) | — |
| 4 | | 10 mM HEPES Buffer (pH: 7.2) | 50 mM |
| 5 | | 10 mM Histidine Buffer (pH: 7.2) | — |
| 6 | | 10 mM Histidine Buffer (pH: 7.2) | 50 mM |
| 7 | | 10 mM Tris Buffer (pH: 7.2) | — |
| 8 | | 10 mM Tris Buffer (pH: 7.2) | 50 mM |
| 9 | Sucrose (10%) + | 10 mM Phosphate Buffer (pH: 7.2) | — |
| 10 | 0.1% HSA | 10 mM Phosphate Buffer (pH: 7.2) | 50 mM |
| 11 | | 10 mM HEPES Buffer (pH: 7.2) | — |
| 12 | | 10 mM HEPES Buffer (pH: 7.2) | 50 mM |
| 13 | | 10 mM Histidine Buffer (pH: 7.2) | — |
| 14 | | 10 mM Histidine Buffer (pH: 7.2) | 50 mM |
| 15 | | 10 mM Tris Buffer (pH: 7.2) | — |
| 16 | | 10 mM Tris Buffer (pH: 7.2) | 50 mM |
| 17 | Control, Reference Formulation (15% Trehalose + 0.1% HSA + % Pluronic F127 ®) | 10 mM Phosphate Buffer (pH: 7.4) | 137 mM |

In other embodiments, a formulation can include a base buffer, sucrose, albumin, mannitol, alanine, methionine, MSG and/or urea in any combination. In accordance with these embodiments, certain formulations can include recombinant HSA having a concentration of about 0.01% to about 2.0% (w/v) or about 0.05% to about 1.0% (w/v), sucrose concentration having a concentration of about 1.0% to about 15% (w/v) or less than 10% (w/v), mannitol concentration having a concentration of about 0.5% to about 15.0% (w/v), alanine having a concentration of about 0.5 mM to about 100 mM or about 5.0 mM to about 50 mM, methionine concentration having a concentration of about 1.0 mM to 5.0 mM or about 1.5 mM to about 3.0 mM, MSG concentration having a concentration of about 5.0 mM to about 100.0 mM or about 5.0 mM to about 25 mM, and urea concentration having a concentration of about 0.05% to about 1.0% (w/v) or about 0.1% to about 0.5% (w/v).

In some embodiments, formulations contemplated herein can include recombinant albumin or HSA, trehalose, mannitol, alanine, methionine, MSG and urea. In accordance with these embodiments, recombinant HSA concentration can be about 0.01% to about 2.0% (w/v) or about 0.05 to about 1.0%, trehalose concentration can be about 1.0% to about 15.0% (w/v) or about 2.5% to less than 10%, mannitol concentration can be about 0.1% to about 10.0% (w/v), alanine can be about 1.0 mM to about 50 mM or about 5 mM to about 25 mM, methionine concentration can be about 0.05 mM to about 5.0 mM or about 0.1 mM to about 4.0 mM, MSG concentration can be about 1.0 mM to about 50.0 mM or about 5.0 mM to about 25.0 mM, and urea concentration can be about 0.05% to about 0.5% (w/v) or about 0.05 to about 0.3% (w/v).

In certain embodiments, formulations disclosed herein can include recombinant HSA, sucrose, alanine and urea. In other embodiments, recombinant HSA concentration can be about 0.01% to about 2.0% (w/v) or about 0.05% to about 0.5% (w/v), sucrose can be a concentration of about 1.0% to about 10% or about 5%, alanine concentration can be about 1.0 mM to about 50 mM, and urea is concentration can be about 0.05% to about 0.5% (w/v) or about 0.05 to about 0.3% (w/v).

In some embodiments, stabilizing one or more live flaviviruses can include reducing loss or reducing degradation of the one or more live flaviviruses upon freezing, freeze drying, at refrigeration temperatures, at room temperature and at about 25° C., as compared to a composition not containing one or more of these agents. In some embodiments, stabilizing one or more live flaviviruses as contemplated herein can include obtaining a 10%, a 20%, a 30%, a 40% or a 50% or more reduction in loss of the live or live, attenuated flaviviruses when formulated by compositions and methods disclosed herein.

In some embodiments, methods disclosed herein can include partially or wholly dehydrating the formulation that includes the live flavivirus. In other embodiments, methods can include partially or wholly rehydrating the formulation that includes the live or live, attenuated flaviviruses prior to administration to a subject as part of an immunogenic composition (e.g. vaccine composition). In yet other embodiments, methods can include freezing live or live, attenuated flavivirus compositions disclosed herein.

Certain embodiments disclosed herein concern live, attenuated flavivirus compositions and methods directed to manufacturing an immunogenic composition (e.g. a vaccine) capable of reducing or preventing onset of a medical condition such as an infection or disease caused by one or more of the flaviviruses contemplated herein. In certain embodiments, one or more live, attenuated flaviviruses can be part of a pharmaceutical composition that can include a pharmaceutically acceptable excipient or carrier. In accordance with these embodiments, the pharmaceutical composition can be administered to a subject in order to reduce onset of a condition caused by a flavivirus infection when administered to a subject, and/or prepared for administration to a subject. A subject can be a mammal for example, a domesticated animal a pet, livestock, other animal or a human subject (e.g. an adult, adolescent or child).

In some embodiments, a composition disclosed herein can include recombinant HSA or HSA, sucrose, methionine and urea. In accordance with these embodiments, recombinant HSA can have a concentration ranging from about 0.05% to about 0.5% (w/v), sucrose can have a concentration ranging from about 0.5% to about 10.0% (w/v), methionine can have a concentration ranging from about 1.0 mM to about 5.0 mM, and urea can have a concentration ranging from about 0.05% to about 0.5% (w/v). In other embodiments, a formulation having recombinant HSA or HSA, sucrose, methionine and urea can further include one or more of alanine at about 5.0 mM to about 25.0 mM, mannitol at about 1.0% to about 15% (w/v) and monosodium glutamate (MSG) at about 1.0 mM to about 20.0 mM. In certain embodiments, the compositions can be in a sucrose base buffer disclosed herein.

In other embodiments, a composition can include recombinant HSA, sucrose and/or trehalose, arginine and urea. In accordance with these embodiments, recombinant HSA or HSA can have a concentration ranging from about 0.05% to about 1.0% (w/v), sucrose and/or trehalose can have a concentration ranging from about 0.5% to about 10.0% (w/v), arginine can have a concentration ranging from about 1.0 mM to about 50.0 mM, and urea can have a concentration ranging from about 0.01% to about 0.5% (w/v) or about 0.05 to about 0.3% (w/v).

In some embodiments, a composition can include recombinant HSA, sucrose and/or trehalose, MSG (monosodium glutamate) and urea. In accordance with these embodiments, recombinant HSA or HSA can have a concentration ranging from about 0.05% to about 0.5% (w/v), sucrose and/or trehalose can have a concentration ranging from about 0.5% to about 15.0% (w/v) or less than 10% (w/v), MSG can have a concentration ranging from about 1.0 mM to about 20.0 mM and urea can have a concentration ranging from about 0.01% to about 0.5% (w/v) or about 0.05 to about 0.3% (w/v).

In some embodiments, compositions and methods disclosed herein can include combining one or more live or live, attenuated flaviviruses with a formulation that includes one or more carbohydrate agents and one or more amino acids or salts, esters or amide derivatives thereof. In accordance with these methods, formulations disclosed herein can stabilize one or more live or live, attenuated flaviviruses from degradation. Formulations disclosed herein are capable of stabilizing for example any serotype or strain of flavivirus. In certain embodiments, flaviviruses include enveloped viruses, for example, dengue virus (e.g. serotypes 1-4), yellow fever virus, West Nile virus and Zika virus.

In other embodiments, a composition disclosed herein can include a flavivirus in a buffer, urea and one or more amino acids that can include, but are not limited to, alanine, arginine, methionine or combinations thereof, and one or more carbohydrate agents that can include, but is not limited to, at least one of sucrose, trehalose and/or mannitol. Certain compositions disclosed herein also can include salt or a salt solution. In accordance with these embodiments, these flavivirus formulations can be used for liquid, frozen or lyophilized storage of a live flaviviruses or live, attenuated flaviviruses at about −80° C. to about 40° C. or above without significant loss of the viral titer in the composition. For example, long-term storage at 4° C. and 25° C. can be achieved using formulations disclosed herein. In certain embodiments, compositions contemplated herein can be partially or wholly dehydrated and/or hydrated. In accordance with these embodiments, long term storage of flavivirus formulations disclosed herein can include accelerated storage of lyophilized formulations and transport or storage at room temperature for long periods of time, greater than 5 weeks.

In some embodiments, live flaviviruses contemplated herein to benefit from compositions and formulations of the present disclosure can include, but are not limited to, dengue virus, West Nile virus, tick-borne encephalitis virus, yellow fever virus, Japanese encephalitis virus, Kunjin virus, St. Louis encephalitis virus, Murray Valley encephalitis virus, Zika virus, or any related flavivirus thereof. In accordance with these embodiments, live flaviviruses or live, attenuated flaviviruses of use in vaccines can be stored at various temperatures where formulations disclosed herein increase stability of the formulation by, for example, reducing degradation of the flavivirus such as reduction in titer loss of the flaviviruses in the formulation. Therefore, use of these formulations to preserve flaviviruses provides solutions regarding efficient manufacturing, transport and delivery of known doses of flaviviruses in the form of immunogenic compositions at reduced costs and time for production. The disclosed formulations allow for more accurate delivery of a live flavivirus or live, attenuated flavivirus immunogenic composition to a patient in need of such a formulation.

In certain embodiments, compositions disclosed herein can be used in methods for preparing vaccine compositions of use for administration to a subject in need thereof. In certain embodiments, immunogenic compositions against flavivirus infection or complications thereof are provided. For example, compositions disclosed herein can be used in order to manufacture vaccines or immunogenic compositions where improved storage conditions and reduced flavivirus degradation are sought. In other embodiments, one or more or all four dengue virus serotypes can be manufactured into an immunogenic composition disclosed herein to reduce degradation of the flavivirus or preserve viral titer in order to more accurately deliver a known quantity of flavivirus to a subject. In certain embodiments, when combined, immunogenic compositions can include multivalent vaccine compositions (e.g., bi-, tri- and tetravalent) to more accurately confer simultaneous protection against infection by more than one species or strain of flavivirus. In some embodiments, flaviviruses can include live flaviviruses and/or live, attenuated flaviviruses. In other embodiments, more than one serotype or strain of a flavivirus or different flaviviruses or chimeras can be combined in an immunogenic composition. In accordance with these embodiments, compositions disclosed herein can provide a stabilizing formulation to more accurate delivery of immunogenic compositions against flaviviruses where transport and storage survival of the live flaviviruses is improved.

In certain compositions, live, attenuated flaviviruses can include nucleic acids encoding one or more proteins from 2 or more different flaviviruses such as a chimera. In other embodiments, immunogenic compositions and formulations disclosed herein can include one or more dengue serotypes referenced as TDV-1 (e.g. dengue serotype 1, a dengue 1/2 chimera), TDV-2 (e.g. dengue serotype 2, a modified live, attenuated dengue-2 virus), TDV-3 (e.g. dengue serotype 3, a dengue 3/2 chimera), and TDV-4 (e.g. dengue serotype 4, a dengue 4/2 chimera), and combinations thereof. It is contemplated that any dengue virus construct (e.g. any flavivirus chimera) or live attenuated dengue virus can be stabilized by formulations disclosed herein. In some embodiments, live, attenuated dengue virus chimeras provided herein can contain the nonstructural protein genes of one dengue virus (e.g. a dengue-2 virus), or the equivalent thereof, and one or more of the structural protein genes or immunogenic portions thereof of at least a second flavivirus (e.g. yellow-fever, other dengue serotype, Zika virus). For example, certain embodiments concern dengue-dengue, dengue-yellow fever, dengue-Zika, dengue-West Nile, dengue-JEV or other flavivirus chimera as mono-, di-, tri- or tetravalent formulations against one or more flaviviruses.

Some embodiments concern methods for decreasing inactivation of a live flavivirus or live, attenuated flaviviruses including, but not limited to, combining one or more flaviviruses with a composition capable of reducing inactivation of the flaviviruses disclosed herein wherein the composition decreases inactivation of the flavivirus. In accordance with these embodiments, the live flaviviruses can include particular flaviviruses, such as those having similar features as the enveloped flaviviruses such as dengue virus serotypes, other flaviviruses having a similar genetic make-up, structural and non-structural protein layout and/or secondary structure or the like to flaviviruses such as dengue virus, Zika virus and yellow fever virus. For example, these formulations are capable of reducing degradation of flaviviruses during particular processes such as encapsidation, manufacturing, transport and administration of a formulated immunogenic composition to a subject, etc. Flaviviruses share several common features such as a common size (40-65 nm), symmetry (enveloped, icosahedral nucleocapsid), nucleic acid (positive-sense, single-stranded RNA of around 10,000-11,000 bases). It is contemplated that any flavivirus or RNA-enveloped virus can be stabilized by the compositions disclosed herein.

In certain embodiments, a live, attenuated flavivirus or flavivirus chimera contemplated herein can be formulated into a pharmaceutical composition wherein the pharmaceutical composition can be administered alone or in combination with other immunogenic agents, and/or can be used to prepare a vaccine composition to be administered to a subject. In certain embodiments, mono-, bi-, tri or tetravalent dengue virus compositions can be formulated into a pharmaceutical composition using compositions disclosed herein to reduce degradation of the formulation, for example, during transport. In accordance with these embodiments, flaviviruses can be lyophilized in any formulation disclosed herein and transported at room temperature without significant loss of titer (See the Examples for some exemplary formulations and methods).

Embodiments herein concern methods and compositions to reduce or prevent degradation and/or inactivation of live, attenuated flaviviruses. In accordance with these embodiments, certain compositions can include combinations of components that reduce degradation and/or inactivation of live flaviviruses and/or live, attenuated flaviviruses. Other embodiments herein concern combinations of agents capable of enhancing stability these flaviviruses. Yet other compositions and methods herein are directed to reducing the need for lower temperatures (e.g., refrigerated or frozen storage) while increasing the shelf life of aqueous and/or reconstituted live flaviviruses or live, attenuated flaviviruses.

In accordance with these embodiments, one or more live or live, attenuated flaviviruses can be combined with one or more amino acids and one or more carbohydrates. In certain embodiments, flavivirus formulations disclosed herein include at least three components: a PBS-based buffer or other buffer and urea. In other embodiments, a salt agent can be added to these compositions in order to enhance buffering capacity or other property of the formulation.

In certain embodiments, carbohydrate agents contemplated of use in compositions herein can include, but are not limited to, sucrose, fructose, galactose, trehalose, mannitol or other similar carbohydrate. In other embodiments, amino acids or derivatives thereof contemplated of use in the compositions and formulations disclosed herein include, but are not limited to, alanine, arginine, methionine, glutamate, monosodium glutamate (MSG) or salts, esters or amide derivatives thereof. In still other embodiments, protein agents of use in the compositions and formulations disclosed herein include, but are not limited to, serum albumin, a human serum albumin (HSA), recombinant form of albumin, a bovine serum albumin (BSA), a fetal bovine serum (FBS), gelatin, dextran, a polyol polymer, or combinations thereof. In some embodiments, the protein agent comprises an albumin at a concentration from about 0.05% to about 2.0% of the particular immunogenic composition.

In certain embodiments, formulations and compositions disclosed herein can include a phosphate buffered saline (PBS) base buffer, with at least one of sodium chloride (NaCl), monosodium and/or disodium phosphate ($Na_2HPO_4$). In some embodiments, the base buffer can also include potassium chloride (KCl) and/or potassium phosphate ($KH_2PO_4$). In other embodiments, a buffer for example, a base buffer, can include sodium chloride at a concentration of about 10.0 mM to about 200.0 mM. It is contemplated that $MgCl_2$ is not included in any of the formulations disclosed herein as it was demonstrated to adversely affect stability of the live flaviviruses.

In certain embodiments, compositions disclosed herein can be used to lyophilize and/or rehydrate live or live, attenuated flaviviruses; transport the flaviviruses at various temperatures from frozen to room temperature and other storage features with improved stability. Compositions contemplated herein can increase stabilization and/or reduce inactivation and/or degradation of a live or live, attenuated flaviviruses at various storage temperatures, during processing and purification, during transport and delivery and during freeze-thaws cycles.

In certain embodiments, compositions disclosed herein can be partially or wholly dehydrated or hydrated. Further, compositions disclosed herein can be used during and after lyophilization of a live flavivirus or live, attenuated flavivirus compositions (see for example, Table 2 below). In accordance with these embodiments, a composition can be 20% or more, 30% or more, 40% or more, 50% or more, 60% or more, 70% or more, 80% or more, 90% or more, or 95% or more dehydrated. Compositions described herein are capable of increasing shelf-life of an aqueous or rehydrated flavivirus composition. In accordance with these embodiments, compositions disclosed herein can increase stability of live flaviviruses or live, attenuated flaviviruses at a wide-range of temperatures such as room temperature, subzero temperatures, elevated temperatures (e.g., from −80° C. to 40° C. and above) under lyophilized or liquid/frozen conditions. In other embodiments, compositions disclosed herein can increase stability of a live flavivirus or live, attenuated flaviviruses 2-fold, 4-fold, 10-fold or more than a live, attenuated flavivirus composition not formulated in at least a composition of a base buffer (e.g., PBS-based buffer, TRIS, HEPES or Histidine etc.), one or more carbohydrate agents, and one or more amino acids.

TABLE 2

Exemplary Lyophilization Parameters of Formulations Disclosed Herein

| | Freeze | | | Primary/ Secondary Drying | | Final |
|---|---|---|---|---|---|---|
| Step | 1 | 2 | 3 | 1 | 2 | 1 |
| Shelf Temp (° C.) | −45 | −45 | −45 | −37 | +25 | 4 |
| Ramp Rate (° C./min) | — | 1.7 | — | 0.1 | 0.1 | 1.0 |
| Time (min) | — | 120 | 120 | 2400 | 360 | HOLD |
| Vacuum (mT) | — | — | 50 | 50 | 50 | 50 |

In certain embodiments, compositions contemplated herein can decrease inactivation and/or degradation of a hydrated live flavivirus for greater than 24 hours at various temperatures (e.g., about 20° C. to about 25° C. or even as high as 40° C.) or refrigeration temperatures (e.g., about 0° to about 10° C. or up to 20° C.). In some embodiments, compositions disclosed herein can maintain stability for 90% or greater flaviviruses for 24 hours or more. In addition, formulations and compositions contemplated herein can reduce inactivation of a hydrated flavivirus during at least 2, at least 3, at least 4, at least 5, at least 6 and more freeze-thaws cycles. Other compositions and methods concern formulations and compositions capable of reducing inactivation of a hydrated live flavivirus or live, attenuated flaviviruses for about 24 hours to about 26 weeks or greater at refrigeration temperatures (e.g., about 0° to about 10° C.).

Still other methods concern using formulations and compositions for 50% or more reduction in the loss of flavivirus titer, for example, after lyophilization and/or after a certain period of time and/or after exposure to a certain temperature. In certain embodiments, the methods disclosed herein provide formulations and compositions capable of reducing the loss of flavivirus titer for a period of 5, or 6, or 7 or more weeks, post-lyophilization and exposure to 25° C. temperatures, as compared to a composition or formulation without formulations disclosed herein.

In certain aspects, formulations can include hydrolyzed gelatin or dextran instead of serum albumin as a protein agent. However, in certain formulations gelatin can be excluded for a variety of reasons including the fact that it is an animal product. Other considerations are that gelatin can cause allergic reactions in immunized children and adults and could be a cause of vaccine-related adverse events. Additionally, gelatin can be sourced from bovine or porcine bones and spinal material. These sources can include extraneous agents and raise safety concerns. Additionally, albumin can be collected from humans, which also poses a potential risk of introducing unsafe extraneous agents. Therefore, certain compositions concern using agents other than animal by-products that have equally stabilizing effects on live attenuated or unattenuated flaviviruses is contemplated. In certain embodiments, recombinant albumin can used in formulations disclosed herein to reduce adverse effects of other albumins.

Compositions disclosed herein can provide for increased protection of live flaviviruses from for example, freezing and/or thawing, and/or elevated temperatures. In certain embodiments, compositions disclosed herein can stabilize, reduce deterioration and/or prevent inactivation of dehydrated live, attenuated viral products in room temperature conditions (e.g., about 25° C.). In other embodiments, formulations and compositions contemplated herein can stabilize, reduce deterioration and/or prevent inactivation of aqueous live, attenuated viral products at about 25° C. or up to or about 40° C. Compositions and methods disclosed herein can facilitate the storage, distribution, delivery and administration of viral vaccines in developed and underdeveloped regions.

Those skilled in the art will recognize that compositions or formulas herein relate to viruses that are unattenuated or attenuated by any method, including but not limited to, cell culture passage, reassortment, incorporation of mutations in infectious clones, reverse genetics, insertions, deletions, other recombinant DNA or RNA manipulation. In addition, those skilled in the art will recognize that other embodiments relate to viruses that are engineered to express any other proteins or flavivirus RNA including, but not limited to, recombinant flaviviruses. Such viruses may be used as vaccines for infectious diseases, vaccines to treat oncological conditions, or viruses to introduce express proteins or RNA (e.g., gene therapy, antisense therapy, ribozyme therapy or small inhibitory RNA therapy) to treat disorders.

Pharmaceutical Compositions

Some embodiments herein relate to pharmaceutical compositions for live or live, attenuated flaviviruses in aqueous or lyophilized form. Those skilled in the art will recognize based on the present disclosure that formulations that improve viral stability (e.g. thermal) and prevent freeze-thaw inactivation of pharmaceutical compositions disclosed herein can improve products that are liquid, powdered, freeze-dried or lyophilized and can be prepared by methods known in the art. After reconstitution, such stabilized vaccines formulations and immunogenic compositions can be administered by a variety routes, including, but not limited to intradermal administration, subcutaneous administration, intramuscular administration, intranasal administration, by inhalation, pulmonary administration or oral administration. In other embodiments, delivery devices to administer any pharmaceutical compositions disclosed herein are contemplated. In accordance with these embodiments, a variety of devices for vaccine delivery are known in the art, including, but not limited to, syringe and needle injection, bifurcated needle administration, administration by intradermal patches or pumps, intradermal needle-free jet delivery (intradermal, etc.), intradermal particle delivery, or aerosol powder delivery.

In certain embodiments, compositions can be described that typically include a physiologically acceptable buffer. Those skilled in the art recognize that PBS-based buffers, TRIS-based buffers, HEPES-based buffers, Histidine-based buffers and buffer systems were found to have unexpected stabilizing effect on the flavivirus formulations and compositions disclosed herein. In addition, those skilled in the art recognize that adjusting salt concentrations to near physiological levels (e.g., saline or 0.15 M total salt) may be optimal for parenteral administration of compositions to prevent cellular damage and/or pain at the site of injection. Those skilled in the art also will recognize that as carbohydrate concentrations increase, salt concentrations can be decreased to maintain equivalent osmolarity and osmolality to the formulation. In certain embodiments, a buffering media with pH greater than 6.0 to about pH 10 is contemplated. In other embodiments, a buffering media with a pH greater than 6.8 to about 8.0 is contemplated. In yet other embodiments, a buffering media with a pH greater than 7.0 to about 7.5 is contemplated.

Embodiments herein provide for administration of immunogenic compositions and vaccine formulations to subjects in a biologically compatible form suitable for pharmaceutical administration in vivo. "Biologically compatible form suitable for administration in vivo" refers to a form of the active agent (e.g., live, attenuated flavivirus compositions) to be administered in which any toxic effects are outweighed by the therapeutic effects of the active agent. Administration of a therapeutically active amount of the therapeutic compositions is defined as an amount effective, at dosages and for periods of time necessary to achieve a desired result. For example, a therapeutically active amount of a compound may vary according to factors such as the disease state, age, sex, and weight of the individual, and the ability formulations to elicit a desired response in the individual. Dosage regimes may be adjusted to provide the optimum therapeutic response.

An active agent, such as a vaccine, may be administered to a subject in an appropriate carrier or diluent, which is co-administered with the agent. The term "pharmaceutically acceptable carrier" as used herein is intended to include diluents such as saline and aqueous buffer solutions. The active agent may also be administered parenterally or intraperitoneally. Pharmaceutical compositions suitable for injection may be administered by means known in the art. For example, sterile aqueous solutions (water soluble) or dispersions and sterile powders for the extemporaneous preparation of sterile injectable solutions or dispersion may be used. In all cases, compositions and formulations can be sterile and can be fluid to the extent that that can be easy ejected from a syringe.

Under ordinary conditions of storage and use, these preparations may contain a preservative to prevent the growth of microorganisms. Compositions and formulations may further be treated to prevent against the contaminating action of microorganisms such as bacteria and fungi. Sterile injectable solutions can be prepared by incorporating active compound in an amount with an appropriate solvent or with one or a combination of ingredients enumerated above, as required, followed by sterilization.

In certain embodiments, compositions and formulations in liquid forms (solutions) can be administered in a manner compatible with the dosage formulation and in such amount as is therapeutically effective. In accordance with these embodiments, the formulations are easily administered in a variety of dosage forms, such as the type of injectable solutions described above. It is contemplated that slow release capsules, timed-release microparticles, and the like can also be employed for administering compositions herein. These particular aqueous solutions are especially suitable for intravenous, intramuscular, subcutaneous and intraperitoneal administration. In some embodiments, formulations disclosed herein can be administered before, during and/or after exposure to a flavivirus of the present disclosure.

Analytical Methods

In certain embodiments, method for identifying an excipient that improves stability of one or more live viruses can include generating an experimental virus stability dataset; constructing an exploratory statistical model by performing univariate regression and multivariate data analyses on the stability dataset; identifying at least one excipient, wherein the at least one excipient increases stability of one or more live viruses. In accordance with these methods, hits and levels of the at least one excipient can be integrated into a definitive screening design (DSD). In other methods, optimal excipient concentrations can be identified for the at least one excipient, wherein the optimal excipient concentration reduces viral potency loss compared to viruses without the at least one excipient. In yet other embodiments, experimental virus stability dataset can be modeled using stepwise regression tools available in JMP 11.2.0 intended for response surface methods (RSM). In accordance with these methods, one or more live viruses can include flaviviruses.

Further methods for identifying optimum conditions for stability of flaviviruses can include evaluating excipients that include, but are not limited to, trehalose, galactose, fructose, sucrose, chitosan, sorbitol, mannitol, serum albumin, human serum albumin (HSA), bovine serum albumin (BSA), fetal bovine serum (FBS), gelatin, dextran, a polyol polymer, alanine, arginine, methionine, MSG and urea. These methods are contemplated to be of use for identifying stabilizing formulations for any virus or live, attenuated virus formulation.

Kits

Other embodiments disclosed herein concern kits for use with compositions and methods as disclosed herein. Compositions and live, attenuated virus formulations may be provided in a kit for use in scientific studies or for delivery and/or use to administer to a subject. In accordance with these embodiments, kits can include, but are not limited to, a suitable container, live or live, attenuated flavivirus compositions, including live, attenuated flaviviruses, and one or more additional agents such as other anti-viral agents, anti-fungal or anti-bacterial agents.

In other embodiments, kits can further include a suitably aliquoted composition of use in a subject to be vaccinated or treated, as appropriate. In addition, compositions and formulations disclosed herein may be partially or wholly dehydrated or may be aqueous. Kits contemplated herein may be stored at room temperatures or at refrigerated temperatures as disclosed herein, depending on the particular formulation.

In other embodiments, kits can generally include at least one vial, test tube, flask, bottle, syringe or other container, into which a composition can be placed, and suitably aliquoted. Where an additional component is provided, kits can also generally contain one or more additional containers into which this agent or component may be placed. Kits herein can also include a composition and any other reagent(s) in containers for commercial sale. Such containers may include injection or blow-molded plastic containers into which the desired vials are retained (e.g., immunogenic or vaccine compositions).

EXAMPLES

The following examples are included to demonstrate certain embodiments presented herein. It is appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

Example 1

Buffer Screen

In certain exemplary methods, liquid compositions and lyophilizable compositions suitable for preclinical and clinical testing and use of flavivirus immunogenic compositions or vaccines were identified. Certain experiments were performed to initially identify candidate buffers and excipients to be used in subsequent stabilization studies. Buffers tested included HEPES, PBS and Tris-based buffers. Excipients tested included various carbohydrates, such as trehalose, galactose, fructose, sorbitol, lactose, sucrose, chitosan or combinations thereof. Other excipients tested included various protein agents, serum albumin, a human serum albumin (HSA), recombinant HSA, a bovine serum albumin (BSA), a fetal bovine serum (FBS), gelatin, dextran, a polyol polymer, or combinations thereof. Yet other excipients screened included various amino acids or salts, esters or amide derivatives thereof, such as alanine, arginine, glutamate (e.g. monosodium glutamate (MSG)) methionine, or combinations thereof. Other components used in these initial testes included various polyols/polymers (e.g., mannitol, gelatin, dextran), osmolytes (e.g., urea), salts (e.g., magnesium chloride, sodium chloride), and chelating agents (e.g., EDTA).

In some exemplary methods, live, attenuated dengue viruses were used as an exemplary flaviviruses in various compositions for pre-clinical and clinical testing. Compositions for these methods are provided herein. In one exemplary experiment, predetermined amounts of a live, attenuated dengue virus immunogenic compositions were used. In another exemplary experiment, a live, attenuated dengue serotype 3 immunogenic composition was used. It is noted that this serotype can be considered the least stable and least immunogenic and was therefore used to develop stabilizing compositions that can be used with the other dengue virus serotypes in addition to one that is less stable. It is contemplated that any attenuated or unattenuated flavivirus can be used in these exemplary compositions to increase stability of the flaviviruses and reduce degradation.

Example 2

Screening for Stabilizing Formulations

In some flavivirus formulations disclosed herein, hydrolyzed gelatin can be used instead of serum albumin as a protein source. However, gelatin, while providing stability to the live, attenuated viruses, can cause allergic reactions when administered to a subject and can sometimes be a cause of vaccine-related adverse events. Certain compositions disclosed herein can include combinations of components that provide comparable outcomes to reduce deterioration of live, attenuated flaviviruses while providing formulations having reduced allergic reactions when administered to a subject. For example, polyols can be used as an additional or alternative source of a protein agent in flavivirus formulations disclosed herein. In some examples, formulations having no albumin or gelatin that are comparable or can provide increased stability to live, attenuated flaviviruses were created. These formulations include, but are not limited to, various concentrations of agents such as a PBS-based buffer, one or more carbohydrate agents, one or more amino acids, one or more protein agents, and/or one or more salt agents.

Stability of live, attenuated flavivirus immunogenic compositions were tested as a function of potency loss using various stabilizing formulations (e.g., titer loss or $Log_{10}$ PFU/dose). Samples of dengue virus serotype 3 (TDV-3) were lyophilized and then exposed to 25° C. for a five week period. Potency loss, or a reduction in the loss of titer over this period, was evaluated for the various formulations, as illustrated in FIG. 1. One base buffer used was PBS with 50 mM NaCl, 0.1% HSA, and 10% carbohydrate. Alanine was present at 10 mM, methionine was present at 2.5 mM, MSG was present at 10 mM, mannitol was present at 5%, and urea was present at 0.25%. A previously-developed formulation that included F-127, trehalose, and albumin (FTA, positive control formulation) was used as a reference. As demonstrated, the various formulations illustrated in FIG. 2 reduce potency loss even more than reference (that was previously demonstrated to improve flavivirus stability), and therefore, provide improved means for stabilizing flavivirus vaccines.

Virus potency observations before/after lyophilization and during accelerated storage stability of the lyophilized flavivirus (e.g. dengue serotype-3, TDV-3) samples are illustrated in Table 3 below. For each formulation, the $\log_{10}$ loss in virus potency due to lyophilization was calculated by subtracting the titer of lyophilized virus samples stored at −80° C. from the initial titer (frozen liquid control stored at −80° C.). In addition, for each formulation, $\log_{10}$ loss in potency during accelerated stability was calculated by subtracting the titer after storage of the lyophilized formulation at 25° C. from same formulation that was stored at −80° C. at 5 weeks.

Most of the formulations demonstrated improved lyophilization yields during the lyophilization process compared to the positive reference control, FTA. After 5 weeks stability study at 25° C., the following trends in virus stability were observed. In one example, flavivirus (e.g. dengue serotype-3, TDV-3) formulations containing high trehalose/sucrose alone (10%), virus potency loss was in the following order: 10% sugar+0.1% HSA>10% sugar+0.1% HSA+Met+MSG+Ala>10% sugar+0.1% HSA+Urea. In another example, flavivirus (e.g. dengue serotype-3, TDV-3) formulations containing combinations of low trehalose/sucrose (1%) and mannitol (4%), virus potency loss was in the following order: 1% sugar+4% Mannitol+0.1% HSA>1% sugar+4% Mannitol+0.1% HSA+Urea>1% sugar+4% Mannitol+0.1% HSA+Met+MSG+Ala. In flavivirus (e.g. dengue serotype-3, TDV-3) formulations containing mannitol alone, virus potency loss was in the following order: 5% Mannitol+0.1% HSA>5% Mannitol+0.1% HSA+Urea>5% Mannitol+0.1% HSA+Met+MSG+Ala.

TABLE 3

Pre-lyophilization, post-lyophilization and post-stability flavivirus (e.g. dengue serotype-3, TDV-3) potency

| No. (corresponds to Table 14) | Samples | liquid | SD | −80° C. | SD | 25° C. | SD | Lyo log loss | Stability log loss (5W) | Total log loss |
|---|---|---|---|---|---|---|---|---|---|---|
| 1 | 1% Trehalose + 0.1% HSA + 4% Mannitol + Met + MSG + Ala | 4.54 | 0.07 | 4.31 | 0.10 | 4.25 | 0.05 | 0.23 | 0.06 | 0.29 |
| 5 | 10% Sucrose + 0.1% HSA + Urea | 5.06 | 0.12 | 4.82 | 0.03 | 4.38 | 0.09 | 0.24 | 0.44 | 0.68 |
| 3 | 1% Sucrose + 0.1% HSA + 4% Mannitol + Met + MSG + Ala | 4.63 | 0.05 | 4.48 | 0.07 | 3.99 | 0.10 | 0.15 | 0.49 | 0.64 |
| 2 | 10% Trehalose + 0.1% HSA + Urea | 4.71 | 0.08 | 4.68 | 0.08 | 4.17 | 0.07 | 0.03 | 0.51 | 0.54 |
| 10 | 5% Mannitol + 0.1% HSA + Met + MSG + Ala | 4.57 | 0.11 | 4.12 | 0.01 | 3.42 | 0.07 | 0.45 | 0.70 | 1.15 |
| 6 | 1% Sucrose + 0.1% HSA + 4% Mannitol | 4.66 | 0.13 | 4.58 | 0.15 | 3.87 | 0.12 | 0.08 | 0.71 | 0.79 |
| 4 | 1% Trehalose + 0.1% HSA + 4% Mannitol + Urea | 4.22 | 0.05 | 4.32 | 0.10 | 3.57 | 0.07 | −0.1 | 0.75 | 0.65 |
| 13 | 10% Trehalose + 0.1% HSA | 5.04 | 0.08 | 4.53 | 0.06 | 3.78 | 0.10 | 0.51 | 0.75 | 1.26 |
| 9 | 1% Sucrose + 0.1% HSA + 4% Mannitol + Urea | 4.77 | 0.04 | 4.56 | 0.07 | 3.78 | 0.10 | 0.21 | 0.78 | 0.99 |
| 8 | 10% Sucrose + 0.1% HSA | 5.02 | 0.06 | 4.84 | 0.08 | 4.05 | 0.11 | 0.18 | 0.79 | 0.97 |
| 14 | Control, reference formulation | 5.03 | 0.04 | 4.57 | 0.04 | 3.76 | 0.04 | 0.56 | 0.81 | 1.37 |
| 12 | 10% Sucrose + 0.1% HSA + Met + MSG + Ala | 5.20 | 0.23 | 4.85 | 0.11 | 4.00 | 0.08 | 0.35 | 0.85 | 1.2 |
| 7 | 1% Trehalose + 0.1% HSA + 4% Mannitol | 4.55 | 0.12 | 4.52 | 0.14 | 3.65 | 0.15 | 0.03 | 0.87 | 0.9 |
| 11 | 10% Trehalose + 0.1% HSA + Met + MSG + Ala | 4.90 | 0.04 | 4.60 | 0.04 | 3.72 | 0.03 | 0.30 | 0.88 | 1.18 |
| 15 | 5% Mannitol + 0.1% HSA + Urea | 3.62 | 0.13 | 3.84 | 0.02 | 0.00 | n/a | −0.22 | 3.84 | 3.62 |
| 16 | 5% Mannitol + 0.1% HSA | 4.01 | 0.14 | 4.08 | 0.08 | 0.00 | n/a | −0.07 | 4.08 | 4.01 |

Example 3

Prediction Profiling

As an additional method for evaluating the efficacy of various formulations on flavivirus vaccine stabilization, prediction profiling methods can be used as a way to down-select various excipients included in the formulation and/or identify excipients that are more effective than others. The effects of various excipients were tested using expression profiling, (data not shown) after lyophilization, five weeks after lyophilization, and five weeks after lyophilization and exposure to 25° C. The data obtained from the prediction profiling were compared to a desirability value, which was used as a guideline for determining the best retention of virus potency after lyophilization and after exposure to 25° C. for 5 weeks. Sucrose and trehalose were found to be interchangeable using these prediction profiling methods. Positive interactions were observed between excipients that can result in increased flavivirus stability profiles after lyophilization and incubation at 25° C. for 5 weeks (data not shown).

Example 4

Lyophilization Stabilization Study

Figure 2:
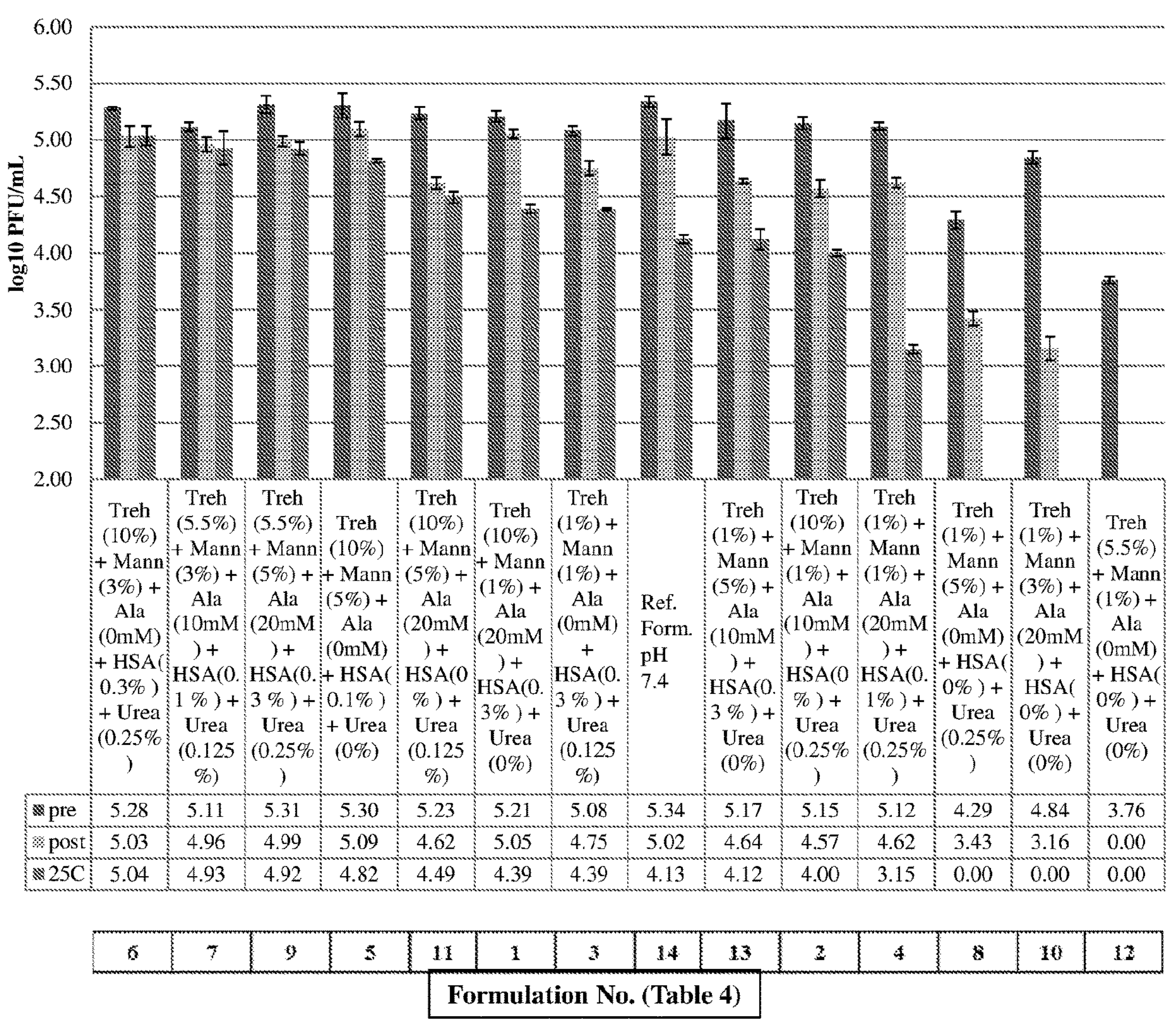
FIG. 2 represents an exemplary bar graph illustrating data obtained from experiments performed while analyzing stability of live flaviviruses in various formulations, before lyophilization, after lyophilization, and after lyophilization and storage at room temperature (e.g. 25° C.) for about 5 weeks, according to some embodiments disclosed herein.
Figure 3A:
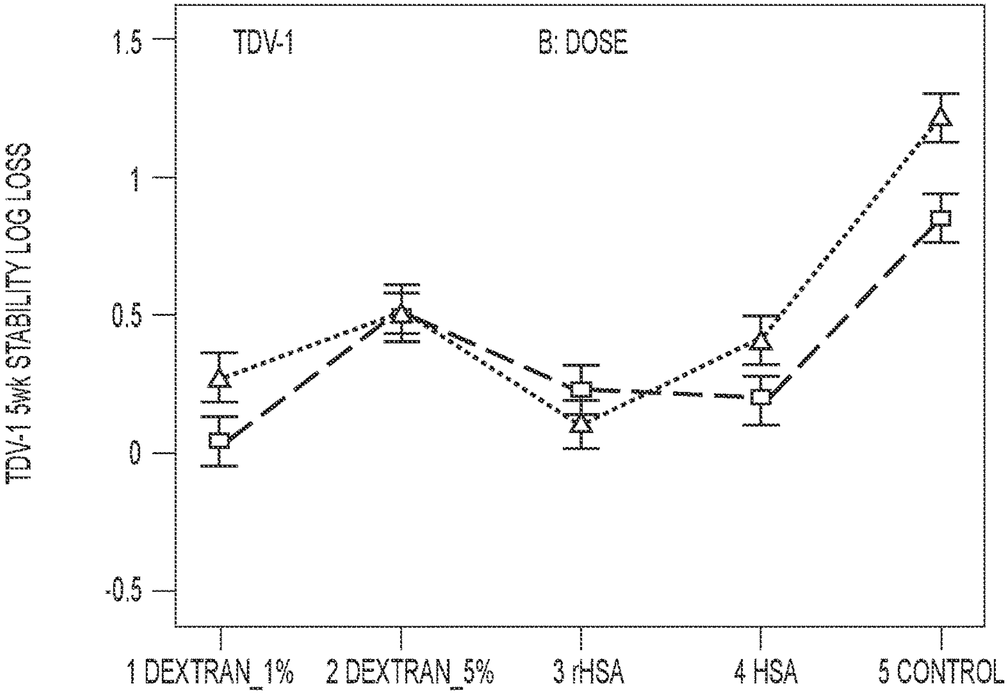
FIGS. 3A and 3B are exemplary graphs representing data from experiments using various formulations for testing stability of live flaviviruses after exposure to room temperature (e.g. 25° C.) for 5 weeks after lyophilization, log loss (3A) and total log loss (3B) at both a 50% bulk drug substance (BDS dose) (solid triangles) and a current dose (CTM Dose) (solid squares), in one embodiment disclosed herein.
Figure 3B:
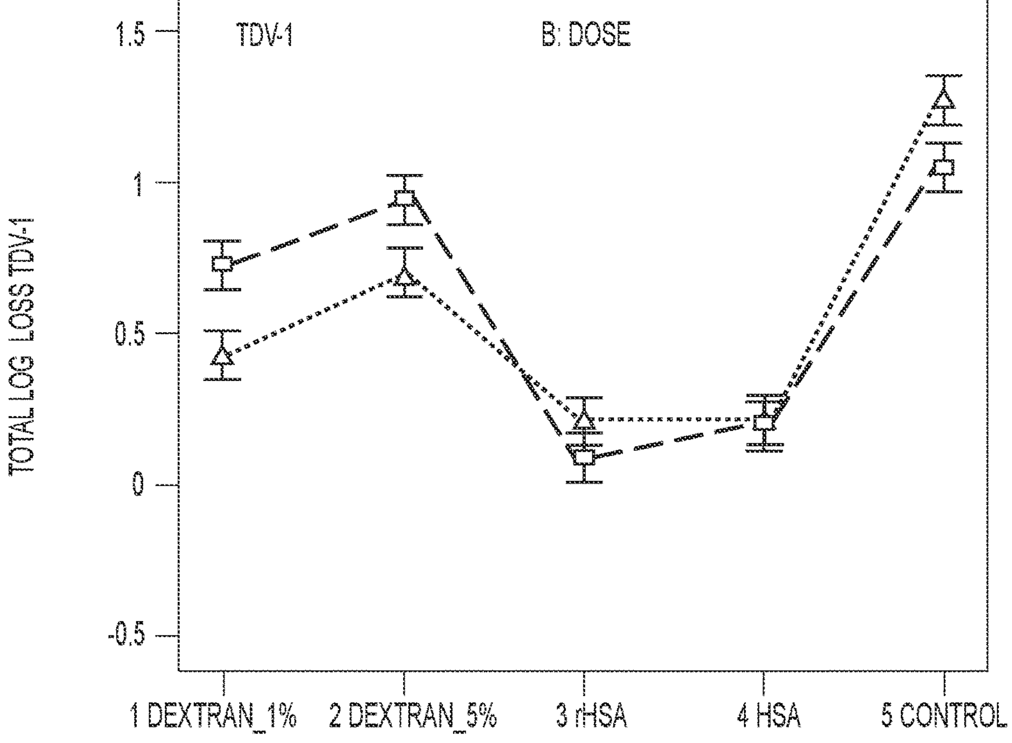
Figure 4A:
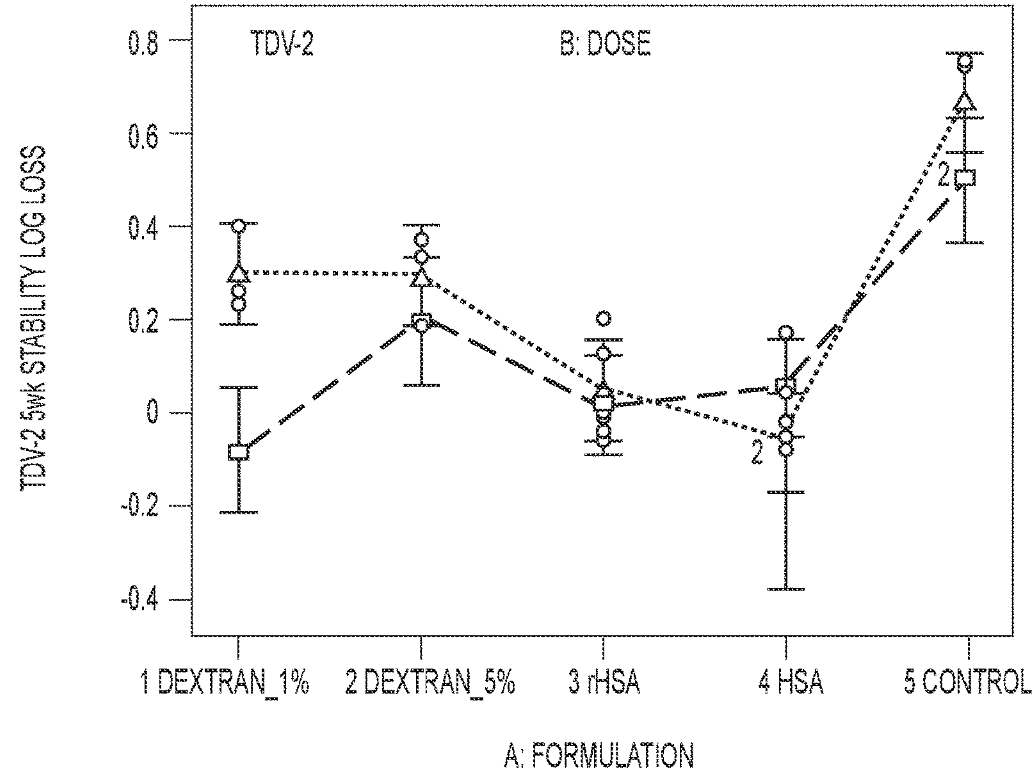
FIGS. 4A and 4B are exemplary graphs representing data from experiments using various formulations for testing stability of live flaviviruses after exposure to room temperature (e.g. 25° C.) for 5 weeks after lyophilization, log loss (4A) and total log loss (4B) at both a 50% BDS (solid triangles) and a CTM (solid squares), in one embodiment disclosed herein.
Figure 4B:
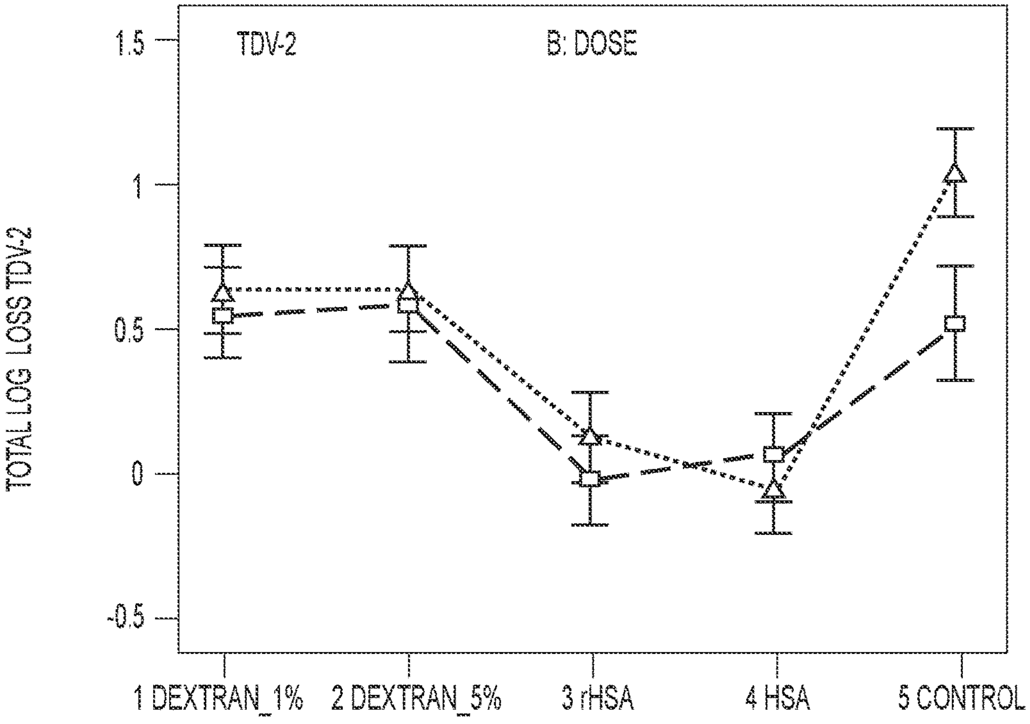
Figures 5A, 5B:
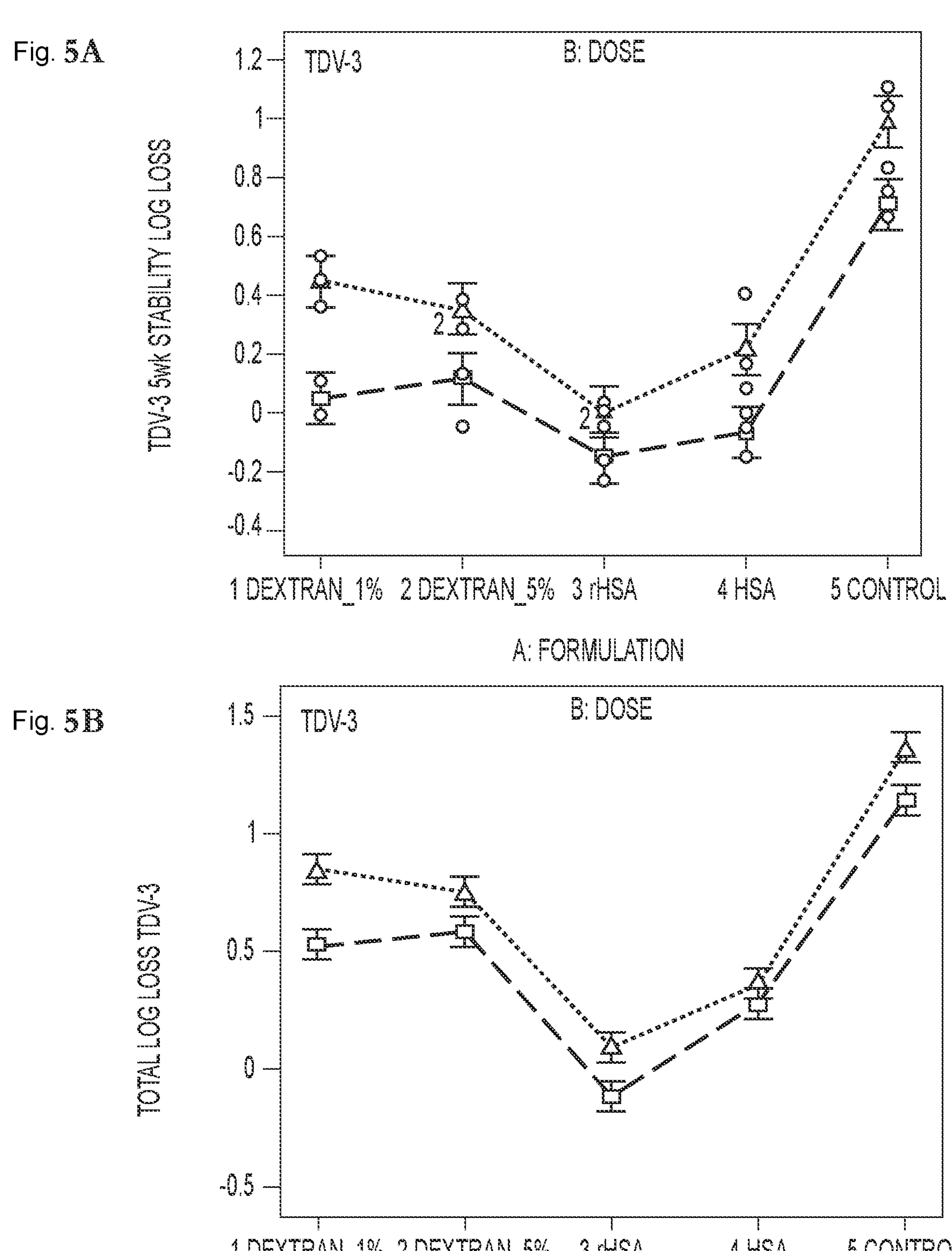
FIGS. 5A and 5B are exemplary graphs representing data from experiments using various formulations for testing stability of live flaviviruses after exposure to room temperature (e.g. 25° C.) for 5 weeks after lyophilization, log loss (5A) and total log loss (5B) at both a 50% BDS (solid triangles) and a CTM (solid squares), in one embodiment disclosed herein.
Figure 6A:
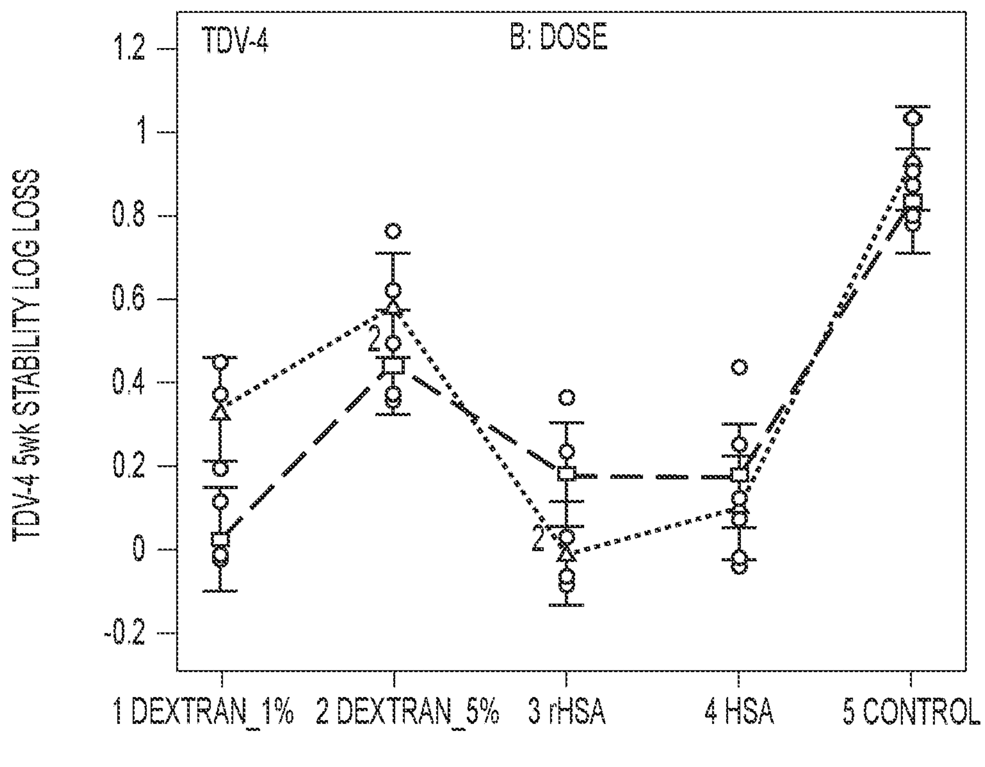
FIGS. 6A and 6B are exemplary graphs representing data from experiments using various formulations for testing stability of live flaviviruses after exposure to room temperature (e.g. 25° C.) for 5 weeks after lyophilization, log loss (6A) and total log loss (6B) at both a 50% BDS (solid triangles) and a CTM (solid squares), in one embodiment disclosed herein.
Figure 6B:
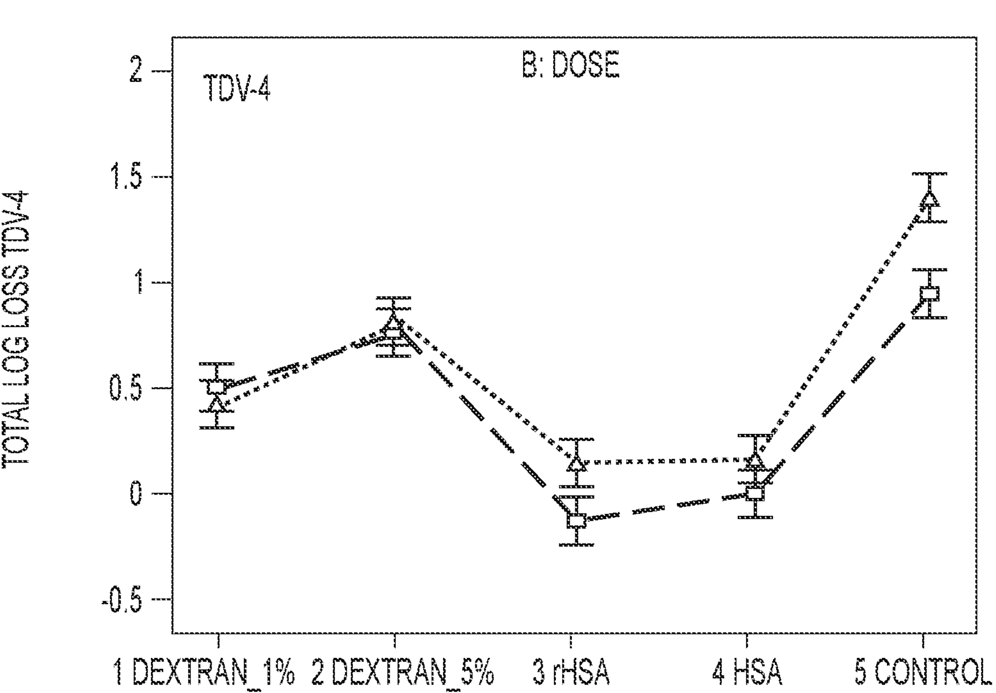

To evaluate effects of various excipients on the stability of a dengue virus serotype 3 vaccine, sample formulations of flavivirus (e.g. dengue serotype-3, TDV-3) vaccines were lyophilized and exposed to 25° C. for 5 weeks, as illustrated in FIG. 2 (see also, Table 4 below). Titers were obtained prior to lyophilization or pre-lyophilization (solid black bar in each triplicate, bar to the left of each test), after lyophilization or post-lyophilization (solid light gray bar in each triplicate, bar in the middle of each test), and after lyophilization and exposure to 25° C. for 5 weeks (solid medium-gray bar to the right of each test; two separate vials were titrated in triplicate). A control, reference formulation that included F-127, trehalose, and albumin (FTA) was used to assess potential improved formulation characteristics.

Statistically significant improvement was observed in virus potency retention after incubation at 25° C. for 5 weeks. Combinations of these excipients demonstrate higher tolerance to thermal stress in the solid state over time compared to the reference/control formulation.

TABLE 4

Exemplary compositions of various lyophilized flavivirus (e.g. dengue serotype-3, TDV-3) formulations All of the formulations in this table were prepared in 10 mM sodium phosphate buffer with 30 mM NaCl, pH 7.2.

| Formulation No. (corresponds to FIG. 2) | Composition | | | | |
|---|---|---|---|---|---|
| | Trehalose % | Mannitol (%) | Ala (mM) | HSA (%) | Urea (%) |
| 1 | 10 | 1 | 20 | 0.3 | 0 |
| 2 | 10 | 1 | 10 | 0 | 0.250 |
| 3 | 1 | 1 | 0 | 0.3 | 0.125 |
| 4 | 1 | 1 | 20 | 0.1 | 0.250 |
| 5 | 10 | 5 | 0 | 0.1 | 0.000 |
| 6 | 10 | 3 | 0 | 0.3 | 0.250 |
| 7 | 5.5 | 3 | 10 | 0.1 | 0.125 |
| 8 | 1 | 5 | 0 | 0 | 0.250 |
| 9 | 5.5 | 5 | 20 | 0.3 | 0.250 |
| 10 | 1 | 3 | 20 | 0 | 0.000 |

TABLE 4-continued

Exemplary compositions of various lyophilized flavivirus (e.g. dengue serotype-3, TDV-3) formulations All of the formulations in this table were prepared in 10 mM sodium phosphate buffer with 30 mM NaCl, pH 7.2.

| Formulation No. (corresponds to FIG. 2) | Composition Trehalose % | Mannitol (%) | Ala (mM) | HSA (%) | Urea (%) |
|---|---|---|---|---|---|
| 11 | 10 | 5 | 20 | 0 | 0.125 |
| 12 | 5.5 | 1 | 0 | 0 | 0.000 |
| 13 | 1 | 5 | 10 | 0.3 | 0.000 |
| 14 | Control, Reference sample (15% Trehalose + 0.1% HSA + 1% Pluronic F127 ®) | | | | |

Example 5

Modeling Stabilization Study with Trehalose and HSA

Potential impact of two excipients, trehalose and HSA, were assessed on stabilizing formulations for subsequent use in a definitive screen. Effects of 0.3% (w/v) HSA and 5% (w/v) trehalose concentrations on stability of exemplary live, attenuated flaviviruses after solid-state lyophilization were assessed (data not shown). These experiments demonstrated that effective stabilization formulations can include a lower concentration of Trehalose, 5% (w/v) and HSA at 0.3% (w/v), as indicated in Table 5 below. In addition, it is noted that mannitol and urea were also analyzed for their ability to stabilize live, attenuated viruses such as flaviviruses and demonstrated to have positive effects on flavivirus stabilization.

TABLE 5

Exemplary compositions of various lyophilized flavivirus (e.g. dengue serotype-3, TDV-3) formulations Max desirability

| Component | Concentration |
|---|---|
| Mannitol | 3.0% (w/v) |
| Trehalose | 5.0% (w/v) |
| Urea | 0.125% (w/v) |
| HSA | 0.3% (w/v) |

Example 6

Screening for Exemplary Tetravalent Stabilizing Formulations

Data obtained for the stabilization formulations for flavivirus (e.g. dengue serotype-3, TDV-3) (above) can be applied to other dengue virus serotypes, including as part of tetravalent dengue virus formulations. Two different target doses were evaluated for each dengue virus serotype (TDV-1, TDV-2, TDV-3 and TDV-4) illustrated in FIG. 3 to FIG. 6, a 50% BDS (triangles) and a CTM (squares). The bulk dose target formulation included about 50% of the bulk drug substance (BDS) for each dengue virus serotype, and the current dose target formulation included about 2.5% of bulk drug substance for each dengue virus serotype (also referred to as the Current Dose or CD). Both the current and bulk dose target formulations also included mannitol (3.0% (w/v)), trehalose (5% (w/v)), and urea (0.125% (w/v)). Table 6 below lists the formulations used to evaluate tetravalent virus stability.

TABLE 6

Exemplary tetravalent dengue virus vaccine formulations

| CD Form. No. | Composition | Final excipient concentrations after formulation with BDS PF 127 (%) | Native HSA (%) | rHSA (%) | Trehalose (%) | Mannitol (%) | Urea (%) | Dextran (%) |
|---|---|---|---|---|---|---|---|---|
| Form 1 CD | Mannitol(3%) + Trehalose (5%) + Urea(0.125%) + Dextran (1%) (low dextran) | 0.02 | 0.002 | | 5 | 3 | 0.125 | 1 |
| Form 2 CD | Mannitol(3%) + Trehalose (5%) + Urea(0.125%) + Dextran (5%) (high dextran) | 0.02 | 0.002 | | 5 | 3 | 0.125 | 5 |
| Form 3 CD | Mannitol(3%) + Trehalose (5%) + Urea(0.125%) + recombinant HSA(0.3%) | 0.02 | 0.002 | 0.3 | 5 | 3 | 0.125 | |
| Form 4 CD | Mannitol(3%) + Trehalose (5%) + Urea(0.125%) + native HSA(0.3%) | 0.02 | 0.3 | | 5 | 3 | 0.125 | |
| FTA_CD | FTA | 1 | 0.1 | | 15 | | | |
| Form 5 50% BDS | Mannitol(3%) + Trehalose (7.5%) + Urea(0.125%) + Dextran (1%) (low dextran) | 0.5 | 0.05 | | 7.5 | 3 | 0.125 | 1 |
| Form 6 50% BDS | Mannitol(3%) + Trehalose (7.5%) + Urea(0.125%) + Dextran (5%) (high dextran) | 0.5 | 0.05 | | 7.5 | 3 | 0.125 | 5 |
| Form 7 50% BDS | Mannitol(3%) + Trehalose (7.5%) + Urea(0.125%) + recombinant HSA(0.3%) | 0.5 | 0.05 | 0.3 | 7.5 | 3 | 0.125 | |
| Form 8 50% BDS | Mannitol(3%) + Trehalose (7.5%) + Urea(0.125%) + native HSA(0.3%) | 0.5 | 0.3 | | 7.5 | 3 | 0.125 | |
| CON_50% BDS | Reference/control | 1 | 0.1 | | 15 | | | |

Target viral titers for the tetravalent dengue virus formulations are illustrated below in Table 7.

TABLE 7

Target viral titers for tetravalent dengue virus vaccine formulations

| | Current dose target titer(CD) PFU/dose | 50% BDS target titer(50% BDS) PFU/dose |
|---|---|---|
| TDV-1 | 2.00E+04 | 5.09E+05 |
| TDV-2 | 5.00E+03 | 1.27E+05 |
| TDV-3 | 1.00E+05 | 2.54E+06 |
| TDV-4 | 3.00E+05 | 8.03E+06 |

As illustrated in FIGS. 3A to 3B to FIGS. 6A to 6B, excipients tested were dextran at 1% (w/v) and 5% (w/v) (as an alternative to HSA), recombinant HSA at 0.3% (w/v), and natural HSA at 0.3% (w/v), along with a FTA positive reference formulation. The effects of each were evaluated after exposure to 25° C. for 5 weeks after lyophilization (FIGS. 3A, 4A, 5A and 6A) and after total loss (FIGS. 3B, 4B, 5B and 6B), which is the summation of potency loss after lyophilization (liquid to solid) and loss after exposure to 25° C. for 5 weeks. Generally, the lower the titer loss and the more overlap between the doses, the higher the stabilizing effect of the excipient.

Example 7

Modeling Stabilization Study with Trehalose and HSA

Based on the above data pertaining to the concentrations of trehalose and HSA, modeling studies were used to reassess the design space for Flavivirus stabilizing formulations (data not shown). Modeling data tested the impact of 0.2% HSA and 5% trehalose concentrations on stability of exemplary live, attenuated Flaviviruses after lyophilization, according to one embodiment disclosed herein, indicated that stabilization formulations can include Trehalose at 5% and HSA at 0.2% (data not shown).

Example 8

Effects of Various Agents on Formulation Cake Integrity and Virus Stability

Various formulations were evaluated at different concentrations and in combinations in lyophilized formulations for their ability to improve dengue virus stability (e.g. dengue virus serotype 3) as well as to form freeze-dried cakes with suitable appearance and suitable physical integrity for a variety of intended purposes. As described herein, lyophilized cakes were rated on a subjective scale from 1 to 3, where 1=bad, 2=fair, and 3=good. Cakes with a rating of 1 were distinguished as having extensive structural collapse, meltback on the bottom and sides, significant shrinkage and retraction from all sides, and/or appearance of granules. Cakes with a rating of 2 had partial shrinkage and retraction from the sides, moderate meltback on the bottom, and/or large cracks or fissures running through the cake horizontally or vertically. Cakes with a rating of 3 were pharmaceutically elegant, appearing as compact, (mostly white, excipient combination depending) cake structures with generally flat surfaces and no or minimal shrinkage or retraction of the cake from the top of the cake or sides of the vial. Effects of varying ratios of carbohydrate such as sugars and mannitol were tested for effects on cake integrity using placebo formulations. An optimized sugar/mannitol ratio was selected for studying the effect of sugar/mannitol (e.g. trehalose or sucrose to mannitol) on virus stability with respect to lyophilization and stability of the lyophilized virus. In this example, this experiment was performed with formulated bulk drug substance a dengue virus serotype 3 (e.g. TDV3).

An exemplary list of placebo formulations evaluated is provided in Table 8 below. Based on results of screening the placebo formulations, three different sugar to mannitol ratios were selected for screening virus stability: sugar (10% (w/v)) alone; sugar to mannitol ratio of 1:4; and mannitol alone (5% (w/v)). Stabilizing excipients (urea and amino acids) identified from previous studies were also evaluated in combinations with different sugar to mannitol ratios.

TABLE 8

Sugar/Mannitol formulations examined during lyophilization stability and cake studies

| Sugar/Mannitol Formulation No. | Sugar | Sugar (w/v) (%) | Mannitol (w/v) (%) |
|---|---|---|---|
| 1 | Trehalose | 1.0 | 4.0 |
| 2 | Trehalose | 2.0 | 4.0 |
| 3 | Trehalose | 2.0 | 3.0 |
| 4 | Trehalose | 10.0 | 0 |
| 5 | Sucrose | 1.0 | 4.0 |
| 6 | Sucrose | 2.0 | 4.0 |
| 7 | Sucrose | 2.0 | 3.0 |
| 8 | Sucrose | 10.0 | 0 |
| 9 | No sugar | 0 | 5.0 |

All of the formulations were prepared in 10 mM sodium phosphate buffer with 30 mM NaCl, pH 7.2 and 0.1% (w/v) HSA. The list of virus-containing formulations that were evaluated as a part of this study is provided in Table 9.

TABLE 9

Formulations evaluated for dengue virus (dengue virus serotype 3) lyophilization and accelerated stability studies

| Form. No. (corresponds to Table 3) | Composition |
|---|---|
| 1 | 10% Trehalose + 0.1% HSA |
| 2 | 10% Trehalose + 0.1% HSA + 0.25% Urea |
| 3 | 10% Trehalose + 0.1% HSA + 10 mM MSG + 10 mM Alanine + 2.5 mM Methionine |
| 4 | 10% Sucrose + 0.1% HSA |
| 5 | 10% Sucrose + 0.1% HSA + 0.25% Urea |
| 6 | 10% Sucrose + 0.1% HSA + 10 mM MSG + 10 mM Alanine + 2.5 mM Methionine |
| 7 | 1% Trehalose + 4% Mannitol + 0.1% HSA |
| 8 | 1% Trehalose + 4% Mannitol + 0.1% HSA + 0.25% Urea |
| 9 | 1% Trehalose + 4% Mannitol + 0.1% HSA + 10 mMMSG + 10 mM Alanine + 2.5 mM Methionine |
| 10 | 1% Sucrose + 4% Mannitol + 0.1% HSA |
| 11 | 1% Sucrose + 4% Mannitol + 0.1% HSA + 0.25% Urea |
| 12 | 1% Sucrose + 4% Mannitol + 0.1% HSA + 10 mM MSG + 10 mM Alanine + 2.5 mM Methionine |
| 13 | 5% Mannitol + 0.1% HSA |
| 14 | 5% Mannitol + 0.1% HSA + 0.25% Urea |
| 15 | 5% Mannitol + 0.1% HSA + 10 mM MSG + 10 mM Alanine + 2.5 mM Methionine |
| 16 | FTA(15% Trehalose + 0.1% HSA + 1% PF127) |

In certain methods, effects of varying the ratio of sugar (e.g., trehalose and/or sucrose) to mannitol on cake appearance of lyophilized samples and subsequently on flavivirus (e.g. dengue virus) stability was evaluated. In one method, to evaluate effect of sugar to mannitol ratio on cake integrity and appearance, placebo formulations were prepared and lyophilized. Following lyophilization, the physical integrity and appearance of cake formation was evaluated (data not shown). Cake integrity appeared to be good with mannitol alone, sugar to mannitol ratio of 1:4 and 2:4, however, partial collapse was observed with formulations prepared with a sugar to mannitol ratio of about 2:3. There was no notable difference in cake integrity observed between trehalose and sucrose formulations. When sugar alone was used, the cake integrity did not appear and test as well was observed using mannitol alone. Based on the cake integrity observations of this exemplary study, the following combinations were selected for virus stability studies: sugar alone, sugar to mannitol ratio of 1:4, and mannitol alone.

In one example, a flavivirus (dengue serotype 3) composition with the selected sugar to mannitol ratios was prepared in combination with the amino acid mixture or urea as additional excipients (see Table 8). Following lyophilization, the physical integrity of cakes was evaluated (data not shown). In examples of formulations containing sugar alone, the cake integrity was similar to control FTA formulations. Formulations containing mannitol alone and sugar to mannitol ratio of 1:4 formed cakes with what appeared to be acceptable appearances and good physical integrity. Addition of urea or the amino acid mixture did not significantly affect cake integrity. These proven formulations appear to be useful for pharmaceutical compositions of use in immunogenic formulations.

Example 9

Combined Semi-Empirical Screening and Design of Experiments (DoE)

To experimentally approach formulation development of a live virus vaccine candidate with improved stability, one would ideally determine the causes and mechanisms of virus degradation and then design formulations to minimize their occurrence. Although this approach has been demonstrated with several viral vaccines it has focused primarily on liquid based formulations and not lyophilized formulations. More empirical approaches are often required including traditional excipient screening studies, quality by design (QbD) approaches (including systematic integration of risk management and prior scientific knowledge with Design of Experiments, DoE), or a combination of both approaches. In this study, a combination approach was demonstrated in a step-wise fashion utilizing a live attenuated dengue vaccine candidate as a model live virus vaccine. To identify formulations that achieve a target product profile of a parenterally administered, lyophilized, multivalent live virus vaccine was tested with sufficient long-term storage at 2-8° C. First, semi-empirical screening was performed to identify virus stabilizers followed by a more detailed evaluation of the top stabilizing excipient "hits" using and exploratory data analysis that acted as guidance for the design of a predictive statistical model by DoE. The step-wise use of a combination approach provides a basis for a systematic, stage appropriate approach to live virus vaccine formulation development during early stage product development.

Preliminary Screening of Pharmaceutical Excipients on Flavivirus (e.g. Dengue Serotype-3, TDV-3) Stability Preliminary screening identified a number of potential stabilizing excipients, in terms of maintaining viral potency during lyophilization and an accelerated stability, while producing acceptable physical integrity of the dried cake after freezing. (See FIGS. 7 and 8). For this initial excipient screening, flavivirus (e.g. dengue serotype-3, TDV-3) formulations were prepared in a base buffer that contained either trehalose or sucrose in 10 mM phosphate buffer with 30 mM NaCl, pH 7.2. As outlined above, other buffers were also evaluated, including HEPES, Tris, and histidine (with and without NaCl). No differences were observed in the storage stability of the aforementioned buffers; however, flavivirus (e.g. dengue serotype-3, TDV-3) appeared to have additional stability when NaCl was included (data not shown). Lyophilized flavivirus (e.g. dengue serotype-3, TDV-3) formulations were prepared using various excipients from different known categories of pharmaceutical additives. Lyophilized flavivirus (e.g. dengue serotype-3, TDV-3) formulations were prepared using various excipients (see Table 12). These additives were selected based on a combination of experience, literature searches of formulation composition of live virus vaccines (marketed and investigational) and scientific rationale. The cake appearance of the lyophilized samples was assessed (Tables 10 and 11) based on a rating system (1-3, where 1 is the worst cake profile and 3 is the best cake profile by observation and physical characteristics).

FIGS. 7A-7D and Table 10 depict lyophilized Flavivirus (e.g. dengue serotype-3, TDV-3) formulations and virus titers at pre and post-lyophilization with respect to different stabilizers in a trehalose base buffer. Loss in virus titer was calculated following lyophilization (FIGS. 7A-7D) and the cake appearance of the lyophilized samples was also assessed (Table 10) based on a visual rating system (as described above). These results demonstrated that many excipients were able to stabilize flaviviruses (e.g. dengue serotype-3, TDV-3) during lyophilization (in the base buffer) including urea, EDTA, polyols, proteins, polymers and amino acids, which resulted in <0.2 log loss in titer. Certain excipients did not individually protect against lyophilization (e.g. $MgCl_2$ and poloxamer 407) while others (sorbitol) could stabilize virus during lyophilization, but failed to produce an elegant cake structure and were excluded from further analysis. Therefore, these agents were not used in the disclosed formulations herein. Similar excipient trends were observed when sucrose replaced trehalose in the base buffer (FIGS. 8A-8B).

Figures 7A, 7B:
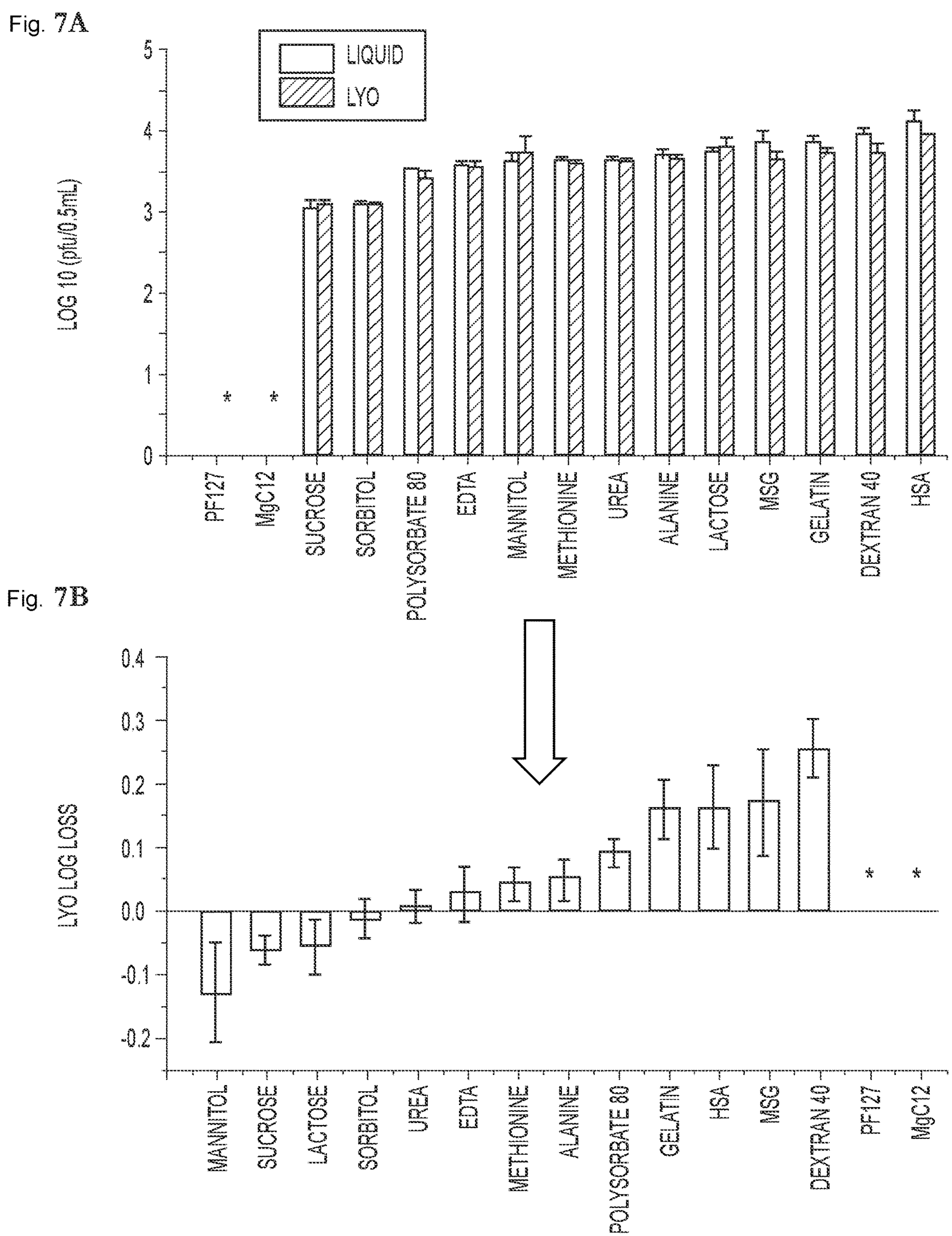
FIGS. 7A-7D represent exemplary bar graphs illustrating effects of single excipients (in a base buffer containing trehalose) regarding a flavivirus viral potency in both liquid and lyophilized forms, in one embodiment disclosed herein.

In this example, FIG. 7A illustrates flavivirus (e.g. dengue serotype-3, TDV-3) viral titers in pre and post lyophilized samples and FIG. 7B illustrates flavivirus (e.g. dengue serotype-3, TDV-3) titer loss following lyophilization. Data are represented as mean values±s.d. Virus titers are provided in $\log_{10}$ pfu/0.5 ml. * represents titers below LOD. Base buffer of these examples contained 10% trehalose in 10 mM phosphate buffer with 30 mM NaCl, pH 7.2. With respect to these exemplary experiments wherein trehalose was replaced by sucrose, FIG. 8A illustrates flavivirus (e.g. dengue serotype-3, TDV-3) viral titer loss following lyophilization. Data are represented as mean values±s.d. Virus titers are given in log 10 pfu/ml.

Figures 7C, 7D:
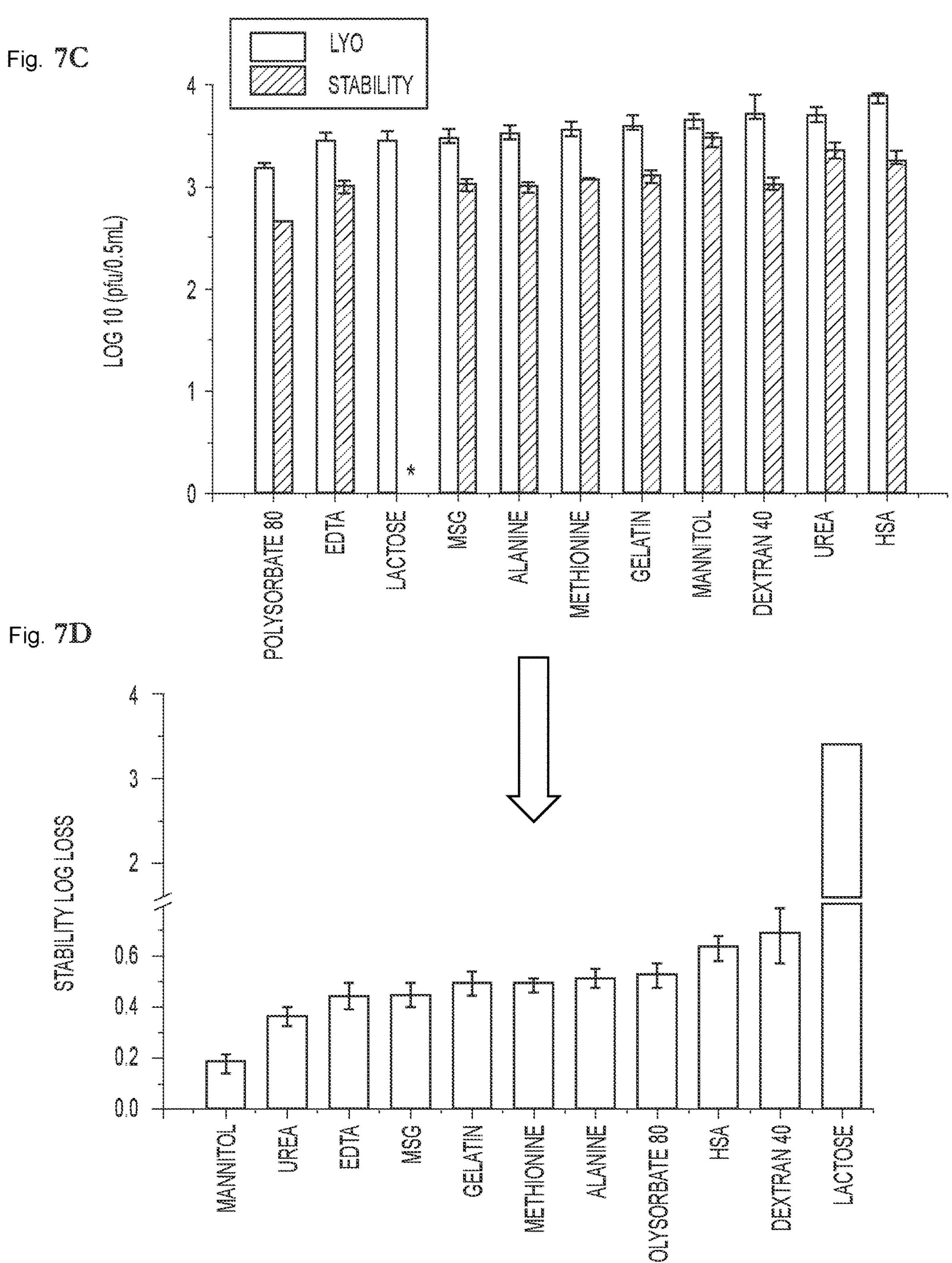
Figure 8A:
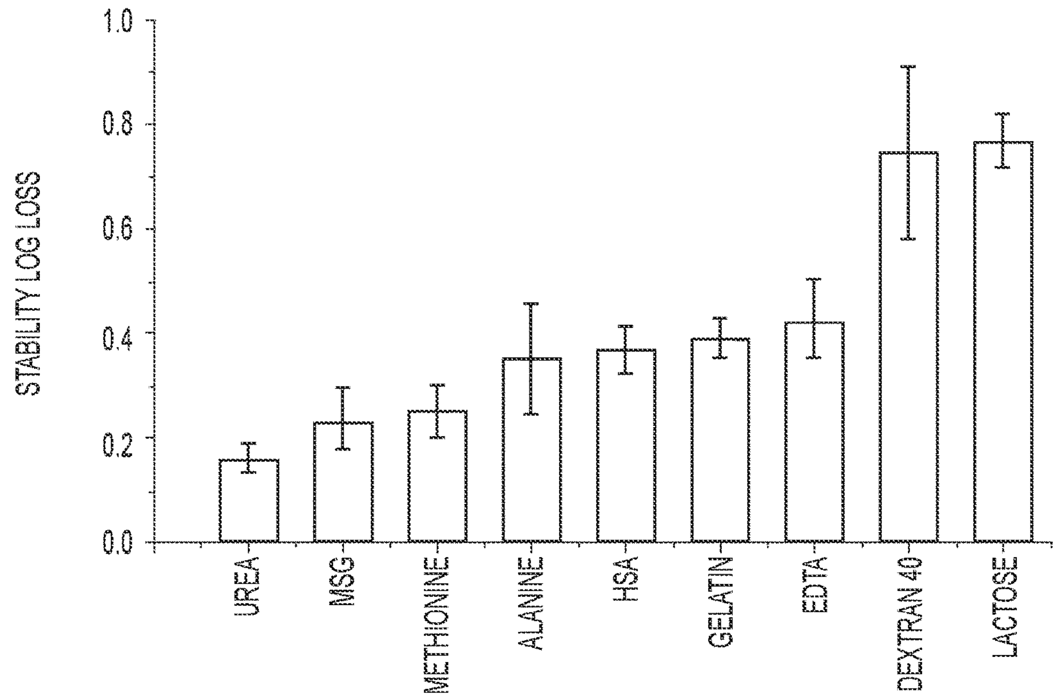
FIGS. 8A-8B represent exemplary graphs illustrating effects of single excipients (in a base buffer containing sucrose) regarding a flavivirus viral potency in both liquid and lyophilized forms, stability loss (8A) and lyophilized log loss (8B) in one embodiment disclosed herein.
Figure 8B:
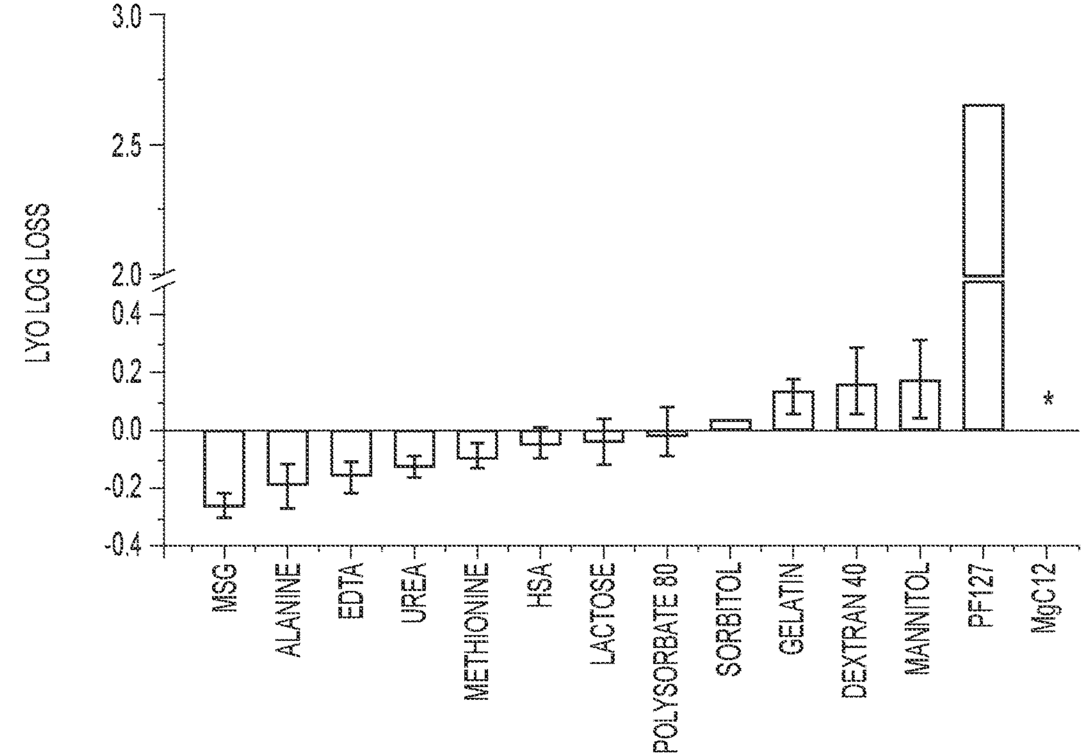

Particular excipient candidates from exemplary experiments illustrated in FIGS. 7A & 8A were further evaluated for their ability to stabilize flavivirus (e.g. dengue serotype-3, TDV-3) via short-term accelerated storage stability at 25° C. for 2 weeks. Virus potency, as measured by viral titers in a plaque assay, and the loss in virus titer over time (expressed as stability login loss), are illustrated in FIGS. 7C and 7D and FIG. 8B for trehalose and sucrose containing base buffer formulations, respectively. FIG. 7C illustrates flavivirus (e.g. dengue serotype-3, TDV-3) viral titers in lyophilized samples after an accelerated stability study, and FIG. 7D illustrates flavivirus (e.g. dengue serotype-3, TDV- 3) titer loss after 2 weeks at room temperature (~25° C.). FIG. 8B illustrates flavivirus (e.g. dengue serotype-3, TDV-3) viral titer loss after lyophilized samples were stored for 5 weeks at room temperature (~25° C.). These results depict that formulations containing HSA, urea, alanine, methionine, MSG, mannitol, or gelatin displayed similar trends in both the base formulations and displayed improved virus stabilization during storage at 25° C. These results indicate that HSA, urea, alanine, methionine, MSG, and mannitol are flavivirus (e.g. dengue serotype-3, TDV-3) stabilizers and were selected for further screening using the same trehalose/-sucrose base buffer formulations.

TABLE 10

The visual cake integrity rating of lyophilized formulations based on visual appearance for flavivirus (e.g. dengue serotype-3, TDV-3) lyophilized formulations containing trehalose (as illustrated in FIG. 7A-7D) (as detailed above, 1-3, where 1 is the worst and 3 is the best).

| Lyophilized formulation | Average Cake Appearance |
|---|---|
| $MgCl_2$ | 1 |
| Sorbitol | 2 |
| Mannitol | 2 |
| Polysorbate 80 | 2 |
| Lactose | 3 |
| Sucrose | 3 |
| HSA | 3 |
| Urea | 3 |
| Alanine | 3 |
| EDTA | 3 |
| Methionine | 3 |
| Gelatin | 3 |
| MSG | 3 |
| Dextran 40 | 3 |
| Reference agent, poloxamer 407 | 3 |

TABLE 11

The visual cake integrity rating of lyophilized formulations based on visual appearance for flavivirus (e.g. dengue serotype-3, TDV-3) lyophilized formulations containing sucrose (as illustrated in FIG. 8A-8B) (as detailed above, 1-3, where 1 has the worst and 3 has the best cake appearance and physical attributes).

| Lyophilized formulation | Average Cake Appearance |
|---|---|
| Mannitol | 1 |
| Sorbitol | 1 |
| MgCl2 | 1 |
| Alanine | 2 |
| Urea | 2 |
| HSA | 3 |
| Lactose | 3 |
| Trehalose | 3 |
| MSG | 3 |
| Methionine | 3 |
| EDTA | 3 |
| PS80 | 3 |
| Gelatin | 3 |
| Dextran 40 | 3 |
| PF127 | 3 |

These results demonstrated that many excipients listed in Table 12 were able to stabilize flavivirus (e.g. dengue serotype-3, TDV-3) during lyophilization (in the base buffer) including urea, EDTA, polyols, proteins, polymers and amino acids, which resulted in <0.2 log loss in titer. The additives $MgCl_2$ and poloxamer 407 imparted the lowest individual agent virus stabilizing potential during lyophilization with >2 log loss individually (however, poloxamer 407 had a synergistic stabilizing effect in the presence of other excipients; see below for more details). Certain excipients (e.g., $MgCl_2$ and poloxamer 407) did not individually protect against lyophilization while others (e.g., sorbitol) could stabilize virus during lyophilization. Similar excipient trends were observed when sucrose replaced trehalose in the base buffer (FIG. 8).

TABLE 12

Summary list of excipients screened for ability to stabilize Flavivirus (e.g. dengue serotype-3, TDV-3) virus during lyophilization and accelerated storage as well as to form pharmaceutically elegant lyophilized cakes. Excipients were evaluated in presence of various base buffers containing additional additives as described in the text.

| Category | Excipients |
|---|---|
| Proteins/Polymers | Human serum albumin and rHSA (0.1, 0.3, and 2%) |
| | Gelatin (3.0%) |
| | Dextran 40 (1-10%) |
| Sugars | Sucrose (1-10%) |
| | D-Trehalose dihydrate (1-15%) |
| | Lactose (4%) |
| Polyols | Sorbitol (3.0%) |
| | Mannitol (1, 3, 5%) |
| Surfactants | Polysorbate-80 (0.05%), PF127 (1.0%) |
| Amino acids | Monosodium 1-glutamate (10 mM) |
| | Methionine (2.5 mM) |
| | Alanine (10 mM) |
| | Arginine (10 mM) |
| Osmolytes | Urea (0.125 and 0.25%) |
| Salts | Magnesium chloride (100 mM) |
| Chelating agents | EDTA (1 mM) |

Some of the exemplary excipient candidates were further evaluated for their ability to stabilize flaviviruses (e.g. dengue serotype-3, TDV-3) via short-term accelerated storage stability at 25° C. for 2 weeks. Virus potency as measured by viral titers in a plaque assay, and the loss in virus titer over time (expressed as stability login loss), are shown in FIGS. 7C and 7D for trehalose containing base buffer formulations, and in FIGS. 8A and 8B for sucrose containing base buffer formulations. Formulations containing, for example, HSA, urea, alanine, methionine, MSG, mannitol, and/or gelatin displayed similar trends in both the base formulations and displayed improved virus stabilization during storage at 25° C. Interestingly, dextran displayed superior stability with trehalose but not with sucrose base buffer. Despite polysorbate 80 and lactose displaying good lyoprotection, these excipients were not able to stabilize flaviviruses (e.g. dengue serotype-3, TDV-3) during storage in the dried state at 25° C. In summary, HSA, urea, alanine, methionine, MSG, and mannitol were identified as potential flavivirus (e.g. dengue serotype-3, TDV-3) stabilizers and were selected for further screening using the same trehalose/sucrose base buffer formulations.

Figure 15A:
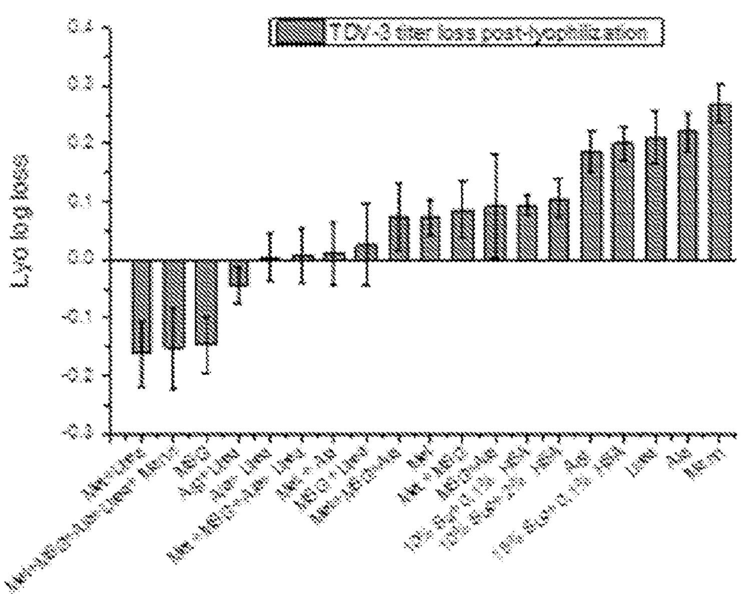
FIGS. 15A-15B are exemplary bar graphs representing data from screening for the effect of various excipient combinations on flavivirus potency, lyophilized log loss (15A) and stability log loss (15B), in some embodiments disclosed herein.
Figure 15B:
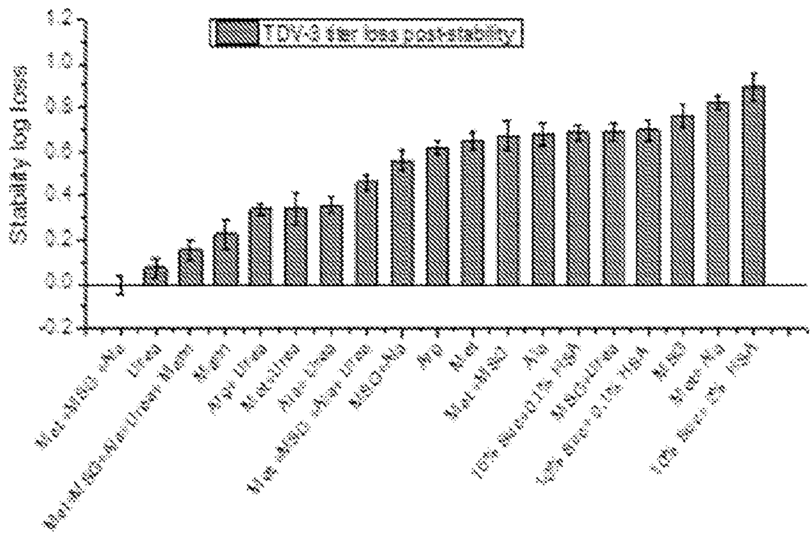

Screening of Excipient Combinations for Flavivirus (e.g. Dengue Serotype-3, TDV-3) Stability The effect of combining the lead excipients at the different concentrations on flavivirus (e.g. dengue serotype-3, TDV-3) titers before and after lyophilization and accelerated stability was evaluated. Referring now to FIG. 9 and FIG. 15, base buffer contained 10% trehalose in 10 mM phosphate buffer with 30 mM NaCl, pH 7.2, and 0.1% HSA. FIGS. 9A and 15A illustrate flavivirus (e.g. dengue serotype-3, TDV-3) titer loss following lyophilization; and FIG. 9B and FIG. 15B illustrate flavivirus (e.g. dengue serotype-3, TDV-3) viral titer loss after lyophilized samples were stored for 5 weeks at room temperature (~25° C.). In these figures, data are represented as mean values±s.d. Virus titers are given in login pfu/ml.

For these studies, HSA (at 0.1 and 0.2% w/v) was added to the base formulations because in certain methods related to the initial screen indicated HSA functioned as an effective lyoprotectant (FIGS. 9 and 15). Loss (<0.2 log loss) of flaviviruses (e.g. dengue serotype-3, TDV-3) titer post-lyophilization at both HSA concentrations was observed in base formulations containing either 10% sucrose or trehalose, respectively (FIGS. 9A and 15A). Therefore, subsequent base buffer formulations were prepared containing phosphate buffer, NaCl, 10% sugar (trehalose or sucrose) with 0.1% HSA and indicated additional excipients. Most of the excipient combinations in either of these base formulations displayed improved virus stability in both post lyophilization and accelerated stability samples (FIGS. 9 and 15). Maximum lyoprotection was demonstrated by using a combination of amino acids and urea added in the base formulations. After 5 weeks at 25° C., either of the base formulations with mannitol and urea was added, either with or without amino acids such as alanine, arginine, MSG and methionine displayed a highly improved viral stability (FIGS. 9 and 15). Increasing the sugar concentrations in the base formulations to 15% did not appear to provide any additional advantage in terms of protecting viral titers.

TABLE 13

The visual cake integrity rating of lyophilized formulations based on visual appearance for flavivirus (e.g. dengue serotype-3, TDV-3) lyophilized formulations (as seen in FIG. 9A-9B) (as detailed above, 1-3, where 1 represents the worst and 3 represents the best cake appearance and physical features).

| Lyophilized formulation | Average Cake Appearance |
|---|---|
| Met + MSG + Ala + Urea + Mann | 2 |
| 15% Tre + 0.1% HSA | 2 |
| Met | 2 |
| Mann | 3 |
| 10% Tre + 2% HSA | 3 |
| 10% Tre + 0.1% HSA | 3 |
| Met + MSG + Ala + Urea | 3 |
| MSG | 3 |
| Ala | 3 |
| Urea | 3 |
| Met + MSG + Ala | 3 |
| Met + MSG | 3 |
| Met + Ala | 3 |
| MSG + Ala | 3 |
| Met + Urea | 3 |
| MSG + Urea | 3 |
| Ala + Urea | 3 |
| Arg | 3 |
| Arg + Urea | 3 |

Figures 10A, 10B:
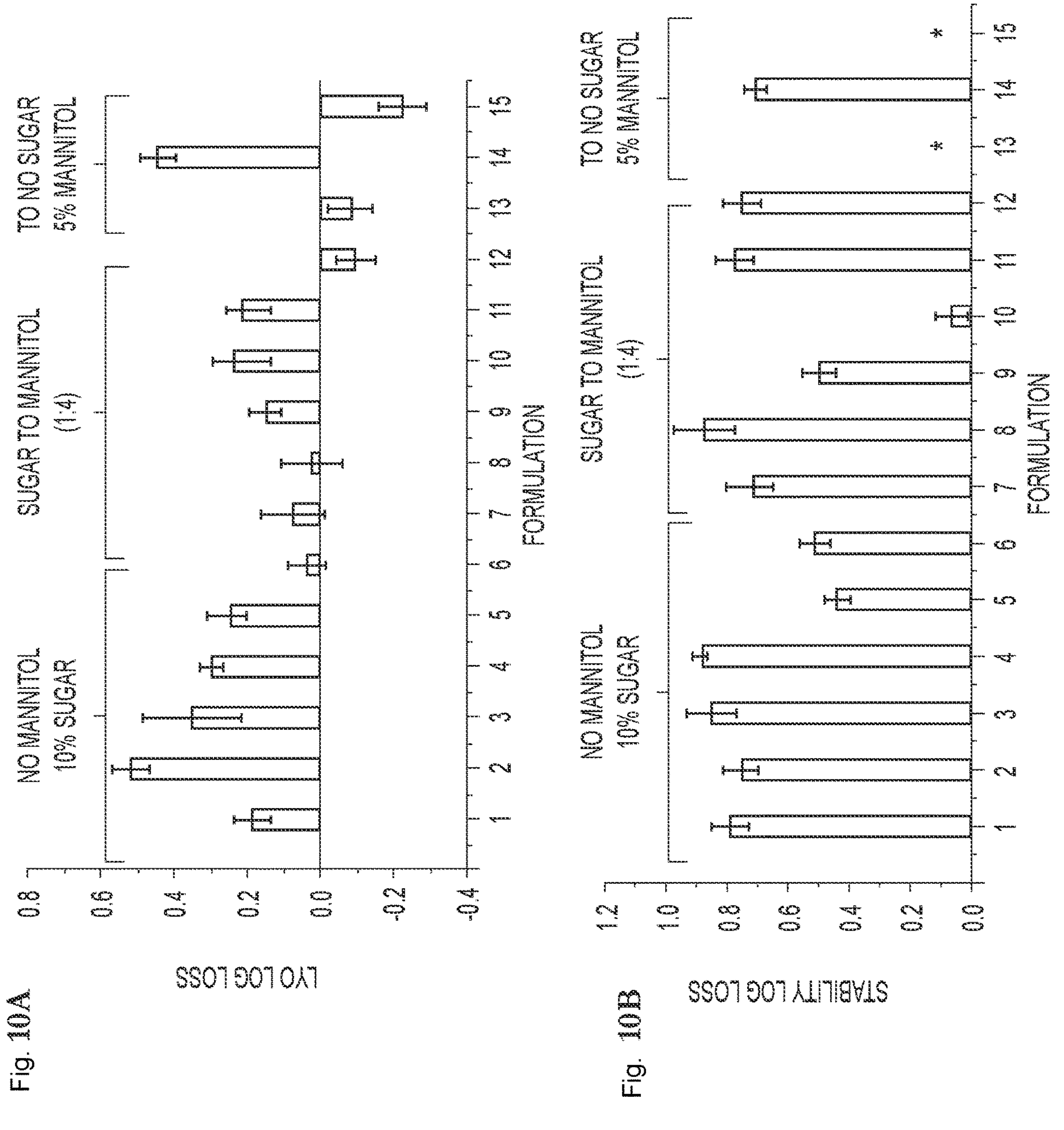
FIGS. 10A-10B are exemplary graphs representing data from screening for the effect of different agents, carbohydrates (e.g. trehalose and sucrose) and mannitol (in a base buffer) on flaviviral stability and log loss, in one embodiment disclosed herein.

The final screening experiments investigated the effect of varying sugar to mannitol ratios on flavivirus (e.g. dengue serotype-3, TDV-3) potency and lyophilized cake integrity. Referring now to the composition formulations detailed in Table 9 and FIGS. 10A to 10B. FIG. 10A illustrates flavivirus (e.g. dengue serotype-3, TDV-3) titer loss following lyophilization, and FIG. 10B illustrates flavivirus (e.g. dengue serotype-3, TDV-3) titer loss after lyophilized samples were stored for 5 weeks at room temperature (~25° C.). Base buffer contained 10 mM phosphate buffer with 30 mM NaCl, pH 7.2, and 0.1% HSA. Data are represented as mean values±s.d. Virus titers are given in login pfu/ml. * N/A below LOD.

Flavivirus (e.g. dengue serotype-3, TDV-3) formulations with the selected sugar to mannitol ratios were prepared in combination with the amino acid mixture or urea as additional excipients in a base buffer (Table 9). Most of the formulations (as found in Tables 3 & 9) demonstrated improved viral titer yields after lyophilization (Table 3). The addition of urea demonstrated improved virus stabilizing potential, compared with the amino acid mixture, in base buffer containing either sucrose or trehalose after storage at 25° C. for 5 weeks (Tables 3 & 9, Formulation 5 and 6; FIG. 10A). Interestingly, when mannitol was added to the base formulations, the amino acid mixture demonstrated increased virus stabilizing potential compared to urea (Tables 3 & 9, Formulation 9 and 10; FIG. 10A). Nevertheless, certain formulations (e.g., 13, 14, and 15) containing mannitol alone demonstrated poor virus stabilizing effect irrespective of addition of urea or amino acid mixture. These observations demonstrate an important effect of amorphous sugar on virus stability, and these experiments further demonstrate sugar and mannitol interactions as important excipients in terms of stabilizing flaviviruses. To further study the effects of these promising stabilizing excipients on flaviviruses (e.g. dengue serotype-3, TDV-3) during freeze-drying and accelerated storage, a rational design of experiment approach was employed as described below.

Design of Experiment

Referring now to FIG. 11, illustrates a comprehensive viral potency loss dataset for every formulation analyzed during screening studies. Data were sorted into three stages of screening represented by Screening Groups 1, 2, and 3 coinciding with data presented in FIGS. 8-10, and FIG. 15. These data illustrate $\log_{10}$ pfu/0.5 mL titers for liquid (pre-lyo), post-lyo, and 5 weeks at 25° C. stability samples. FIGS. 11A and 11B illustrate identification of statistically significant terms that provide protection from freeze-drying and thermal challenge ($\mathrm{Log}_{10}$ lyo loss (FIG. 11A) and $\log_{10}$ drop 5 weeks at 25° C. (FIG. 11B)). Data were modeled using stepwise regression to determine which terms were significantly impacting potency as statistically observed. In addition to using the Bayesian Information stopping Criterion to help converge on a best fit model, main effect and interaction terms were considered significant if their probability value was <0.05. The adequacy of the model fit was also assessed using the $R^2$ values.

The semi-empirical screening of excipients and formulations generated a large dataset of frozen liquid (pre-lyo), post-lyo, and accelerated stability (5 weeks at 25° C.) viral potency measurements for 85 individually prepared formulations of flaviviruses (e.g. dengue serotype-3, TDV-3) (data not shown). Analyzing the comprehensive dataset visually reveals that, with each sequential screening experiment, there is an increase in retention of flavivirus (e.g. dengue serotype-3, TDV-3) potency for each condition in addition to improved cake appearance. Varying excipient concentrations and their combinations throughout the screening exercises assembled an empirically derived data set that could be utilized using regression modeling to construct an exploratory statistical model.

To determine which excipients (or terms) were individually contributing or interacting to affect flavivirus (e.g. dengue serotype-3, TDV-3) potency losses, the dataset was modeled using stepwise regression tools available in JMP 11.2.0 intended for response surface methods (RSM). The regression analysis utilized the minimum Bayesian Information Stopping Criterion to arrive at the best model and terms and interactions that did not show significance (probability statistic <0.05) were excluded. Model fits with $R^2$ values of 0.44 and 0.73 were determined for $\log_{10}$ lyo loss and $\log_{10}$ drop 5 weeks at 25° C., respectively (FIGS. 11A and 11B). Excipients including HSA, urea, mannitol, and the sugars sucrose and trehalose were identified as being statistically significant for limiting flavivirus (e.g. dengue serotype-3, TDV-3) potency loss after lyophilization (data not shown). Similar sets of excipients were demonstrated to protect flavivirus (e.g. dengue serotype-3, TDV-3) potency loss during accelerated storage stability. Certain additives: urea, mannitol, and HSA demonstrated single term significance while combinations of trehalose or sucrose with urea, and trehalose with mannitol were identified as having significant two term interactions. Amino acids, alanine, methionine, and MSG were included in the model because they seemed to provide stabilizing effects during the screening stages, but were shown in this analysis to not be statistically significant. Utilizing these exploratory models as guidance, the additives HSA, urea, mannitol and trehalose or sucrose were chosen as promising candidates for further study.

TABLE 14

DOE formulation design

| DOE | Composition | | | | |
|---|---|---|---|---|---|
| Form. No. | Trehalose % | Mannitol (%) | Ala (mM) | HSA (%) | Urea (%) |
| 1 | 10 | 1 | 20 | 0.3 | 0 |
| 2 | 10 | 1 | 10 | 0 | 0.250 |
| 3 | 1 | 1 | 0 | 0.3 | 0.125 |
| 4 | 1 | 1 | 20 | 0.1 | 0.250 |
| 5 | 10 | 5 | 0 | 0.1 | 0.000 |
| 6 | 10 | 3 | 0 | 0.3 | 0.250 |
| 7 | 5.5 | 3 | 10 | 0.1 | 0.125 |
| 8 | 1 | 5 | 0 | 0 | 0.250 |
| 9 | 5.5 | 5 | 20 | 0.3 | 0.250 |
| 10 | 1 | 3 | 20 | 0 | 0.000 |
| 11 | 10 | 5 | 20 | 0 | 0.125 |
| 12 | 5.5 | 1 | 0 | 0 | 0.000 |
| 13 | 1 | 5 | 10 | 0.3 | 0.000 |

Figure 12A:
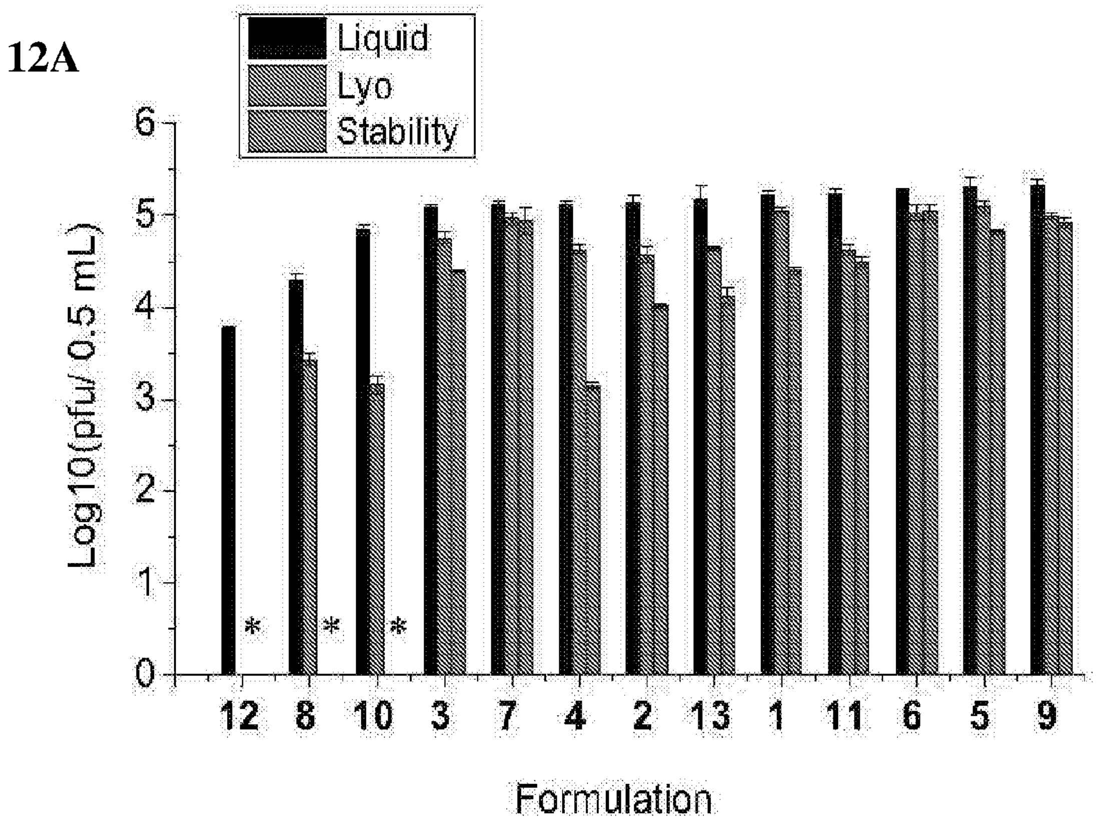

Referring now to Table 14 and FIG. 12, the Table and Figures provide as follows: Table 14: DOE formulation design FIG. 12A: Flavivirus (e.g. dengue serotype-3, TDV-3) viral titers in liquid, lyophilized (stored at −80° C.) and stability samples (lyophilized formulations stored at 25° C., 5 weeks), FIG. 12B: Flavivirus (e.g. dengue serotype-3, TDV-3) titer loss during lyophilization and 5 weeks stability at 25° C. All formulations contained 10 mM sodium phosphate, 30 mM NaCl, pH 7.2 as an exemplary buffer. FIG. 12C represents three Sorted Estimates Charts generated by analysis of DSD data using forward stepwise regression and the stopping rule set to minimize the corrected Akaike's Information Criterion (AICc) using JMP 11.2.0. Main effect and interaction terms were considered significant if their probability value was <0.05. The adequacy of the model fit was also assessed using the $R^2$ values.

The lead excipient hits and levels identified by the exploratory univariate regression and multivariate data analyses were integrated into a definitive screening design (DSD) (Table 14) in order to confirm by design the significance of their impact to stability and to explore the optimal concentration range for each excipient. Although displaying similar statistical impacts, trehalose was chosen over sucrose because of its additional interactions identified by the exploratory model analysis. Although alanine was not found to be a significant, it was included in the DSD as a representative amino acid, which were present in the most promising formulations during screening. The choice of excipient concentration ranges was informed by the response surface model prediction profiler (data not shown) and the DSD was constructed using the Design of Experiments platform in JMP 11.2.0 and generated 13 individual formulations for assessment. Flaviviruses (e.g. dengue serotype-3, TDV-3) were added to each formulation outlined in Table 14, lyophilized, and challenged at 25° C. for 5 weeks. Definitive Screening Design (DSD) design of experiments formulations for each flavivirus (e.g. dengue serotype-3, TDV-3) and titer in liquid, lyophilized (stored at 80° C.) and stability samples (lyophilized formulations stored at 25° C.) were illustrated. (FIGS. 11A and 11B) Main effect and interaction terms were considered significant if their probability value was <0.05. Solid vertical lines represent p value threshold and any bar crossing these lines demonstrates significant effect. The adequacy of the model fit was also assessed using the R2 values. * N/A below LOD. Formulation details are as follows: F1: 10% Tre+1% Mann+Ala(20 mM)+0.3% HSA; F2:10% Tre+1% Mann+Ala(10 mM)+0.25% U; F3:1% Tre+1% Mann+0.3% HSA+0.125% U; F4:1% Tre+1% Mann+Ala(20 mM)+0.1% HSA+0.25% U; F5:10% Tre+5% Mann+0.1% HSA; F6:10% Tre+3% Mann+0.3% HSA+0.25% U; F7:5.5% Tre+3% Mann+Ala(10 mM)+0.1% HSA+0.125% U; F8:1% Tre+5% Mann+0.250% U; F9:5.5% Tre+5% Mann+Ala (20 mM)+0.3% HSA+0.25% U; F10:1% Tre+3% Mann+Ala(20 mM); F11:10% Tre+5% Mann+Ala(20 mM)+0.125% U; F12: 5.5% Tre+1% Mann; F13: 1% Tre+5% Mann+Ala (10 mM)+0.3% HSA. Mann, mannitol; Tre, trehalose dihydrate; HSA, human serum albumin; Ala, alanine; and U, urea.

Figure 12B:
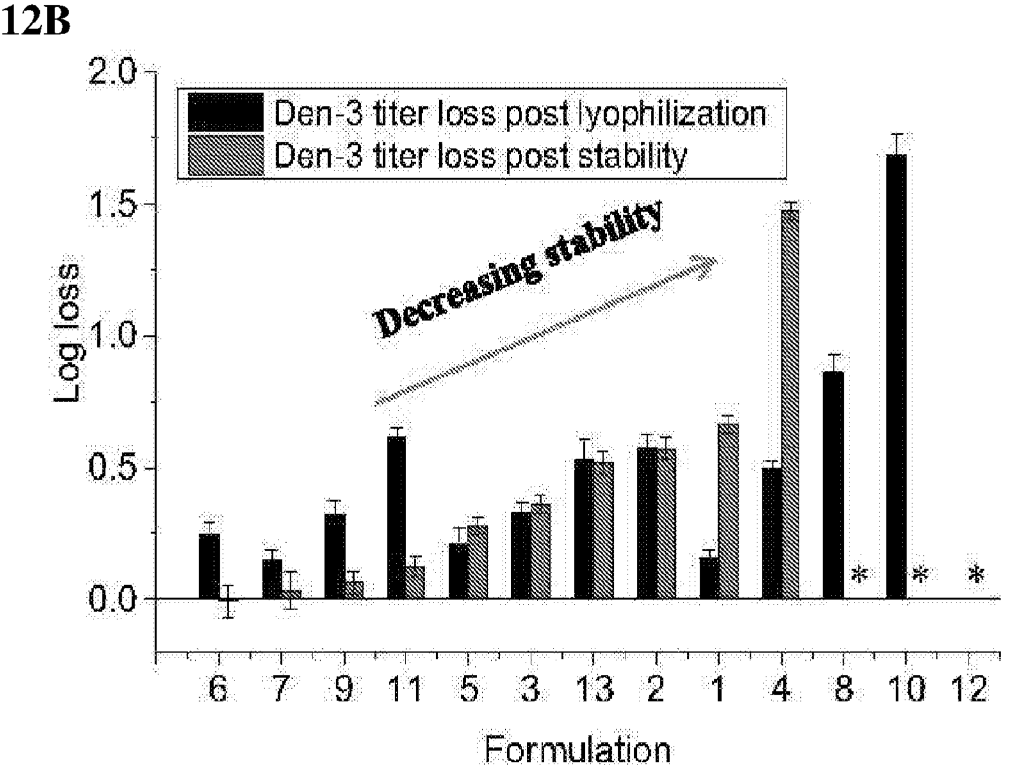

Frozen liquid (pre-lyo), post lyo (time 0), and 5 week stability samples were measured for viral potency by plaque assay (FIGS. 12A and 12B). The data set generated by the DSD was analyzed using forward stepwise regression and the stopping rule set this time to minimize the corrected Akaike's Information Criterion (AICc) in JMP 11.2.0. This stepwise regression approach identified the most significant terms and further illuminated the design space for each of the excipients tested (FIG. 12C). Model fits with $R^2$ values of 0.79, 0.89, and 0.99 for each of the responses, including login total potency loss. The analysis of losses in viral potency highlighted that mid to high concentrations of trehalose and HSA significantly stabilized potency loss when in concert with low to mid concentrations of mannitol and mid to high concentrations of urea. It is noted that alanine demonstrated no statistically significant effect (not identified by the model).

A contour profiler showing optimized design space for the Definitive Screen Design response surface model for two factor terms, trehalose and HSA, with Mannitol and urea having locked mixture values of 3% and 0.125%, respectively, was generated using JMP 11.2.0. Utilization of JMP's prediction profiler (data not shown). The contour profiler was generated from the predictive DSD models for each of the responses identified the optimal excipient concentrations that protect against viral potency losses as being: 5% trehalose, 3% mannitol, 0.3% HSA, and 0.125% urea.

Evaluate Excipient Combinations for Tetravalent Dengue Vaccine Dosage Form

TABLE 15

Formulation design using DOE

| DOE Formulation No. | Composition |
|---|---|
| Form_1 | Mannitol (3%) + Trehalose (5%) + Urea (0.125%) + Dextran (1% (low dextran) |
| Form_2 | Mannitol (3%) + Trehalose (5%) + Urea (0.125%) + Dextran (5%) (high dextran) |
| Form_3 | Mannitol (3%) + Trehalose (5%) + Urea (0.125%) + recombinant HSA (0.3%) |
| Form_4 | Mannitol (3%) + Trehalose (5%) + Urea (0.125%) + native HSA (0.3%) |

Referring now to Table 15 and FIG. 13, panels provides as follows: Table 15: Formulation design using DOE, (FIG. 13A: Titer loss of tetravalent formulation: TDV serotypes 1-4 (an immunogenic formulation) after lyophilization, FIG. 13B: Titer loss of TDV serotypes 1-4 (in a tetravalent vaccine formulation) after lyophilized samples were stored at 25° C. for 5 weeks, FIG. 13C: Total viral titer loss of TDV serotypes 1-4 after lyophilization and 25° C. storage for 5 weeks. All DOE formulations also contained 10 mM sodium phosphate, 30 mM NaCl, pH 7.2*Not calculated (below LLOD).

Tetravalent DOE formulations (TDV-1, -2, -3, -4) were prepared by varying the concentration of dextran (DOE Formulations 1 & 2), rHSA (DOE Formulation 3), and nHSA (DOE Formulation 4) in the base formulation containing trehalose, mannitol, phosphate buffer and NaCl (Table 15). DOE formulations were evaluated and rated as a function of lyophilized cake integrity (data not shown) and combined login loss in virus titer (FIG. 13B) following lyophilization and accelerated stability. DOE formulations containing rHSA or nHSA displayed improved virus potency yields when compared to dextran-containing formulations. DOE formulations containing rHSA displayed the highest viral potency recovery for all serotypes with <0.3 log loss for TDV-2 to TDV-4 and 0.5 log loss for TDV-1 (FIG. 13B). Partial cake collapse, however, was observed with the HSA containing formulations (data not shown). Interestingly, DOE formulations containing dextran were more elegant in terms of cake physical appearance, but were not able to preserve virus potency after lyophilization (FIG. 13B).

Real Time Stability Study of Tetravalent Dengue Vaccine Formulations

Figures 14A, 14B:
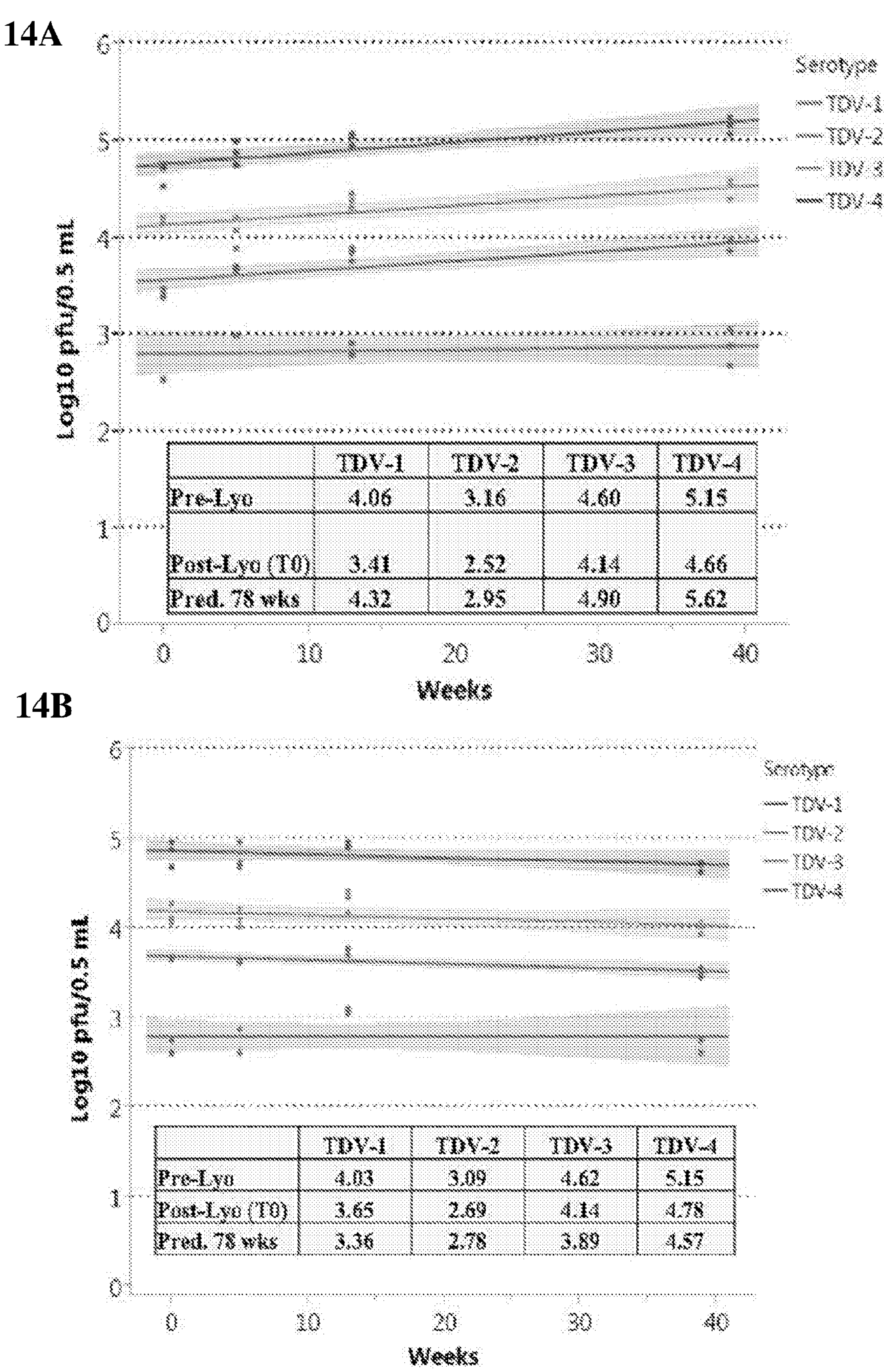
FIGS. 14A-14D are exemplary line graphs representing different flaviviruses (e.g. dengue-1, -2, -3 and -4) as lyophilized immunogenic formulations stored at refrigeration temperatures (e.g. 4° C.) for about 39 weeks, in some embodiments disclosed herein.
Figure 14C:
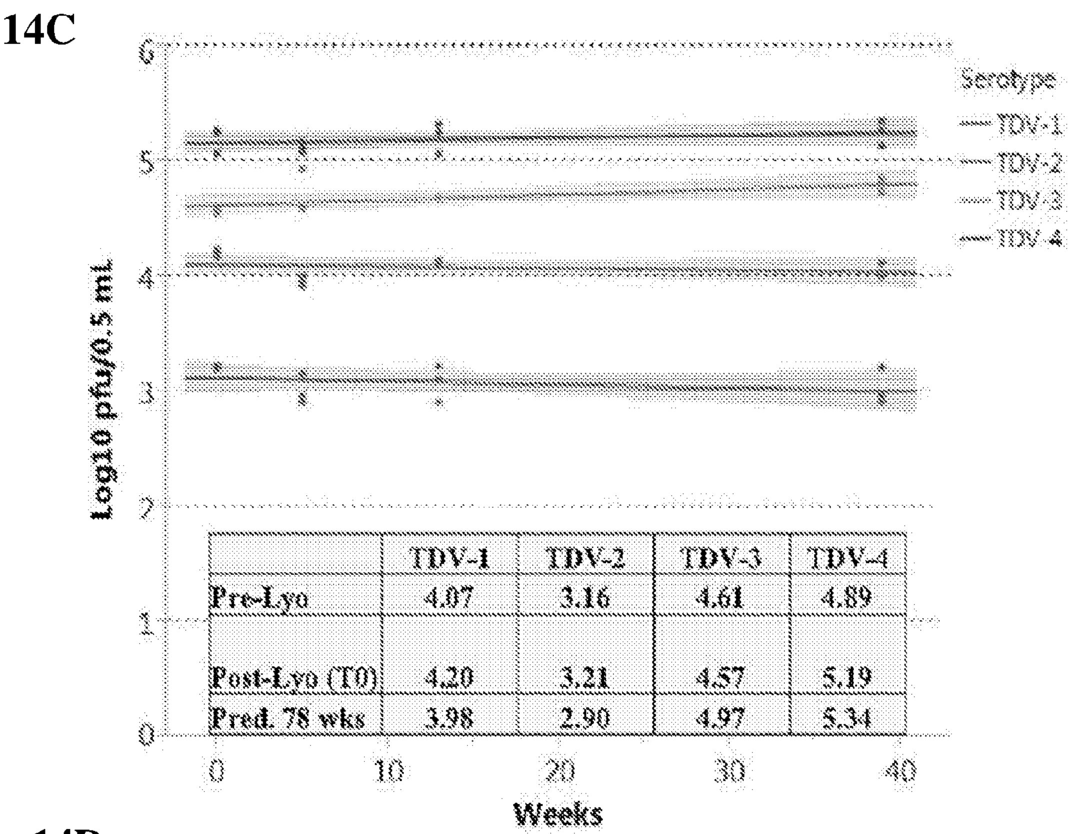
Figure 14D:
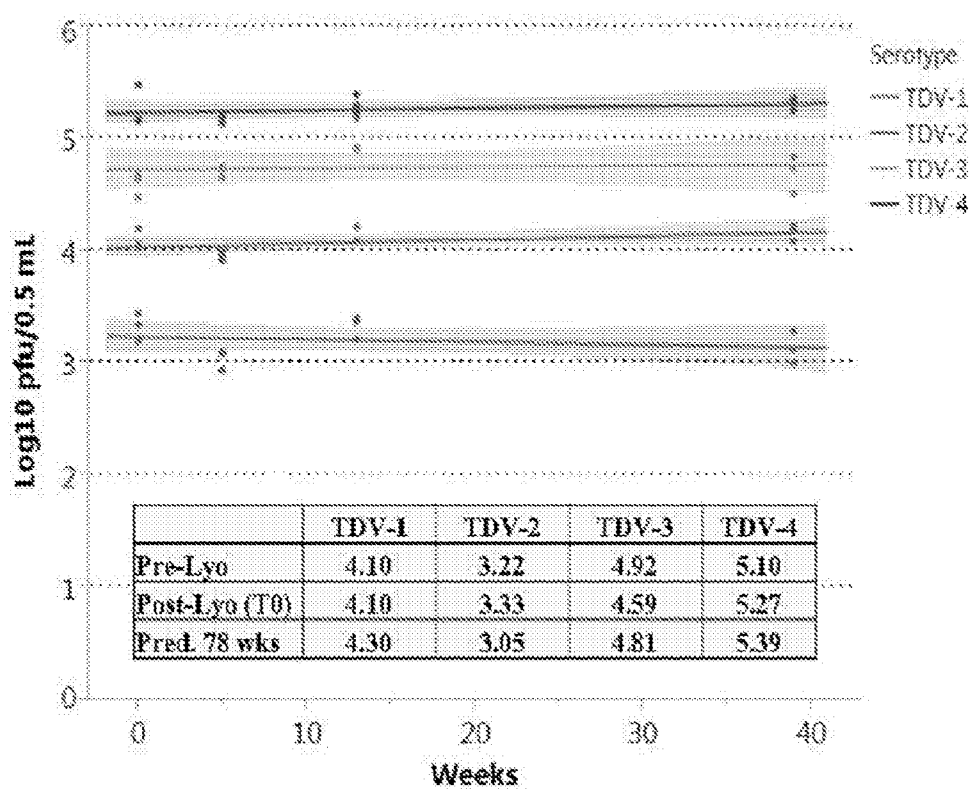

In addition to the accelerated stability study with the tetravalent TDV at 25° C., a 4° C. stability study was initiated to generate real-time stability at the target long-term storage temperature. Each DOE formulation was stored at 4° C. for up to 39 weeks with viral potency measurements taken at time zero, 5, 13, and 39 weeks. Referring now to FIG. 14, DOE formulations 1-4, contained 5% trehalose, 3% mannitol, 0.125% urea, in 10 mM sodium phosphate with 30 mM NaCl pH 7.2 and the following additives: 1% dextran (FIG. 14A), 5% dextran (FIG. 14B), 0.3% recombinant HSA (FIG. 14C), or 0.3% native HSA (FIG. 14D). Lyophilized samples were stored at 4° C. and reconstituted for viral potency measurements at 0, 5, 13, and 39 weeks. Highlighted region represents the upper and lower 95% Confidence Interval determined in JMP 11.2.0. The integrated table in each graph contains $Log_{10}$ pfu/0.5 mL titer data for each serotype for liquid (Pre-Lyo), time 0 (Post-Lyo (TO)), and the predicted titer at 78 weeks (Pred. 78 wks). (Of note: the predicted titer was determined by use of the Adapt2 Version 3.4.1 Tool developed by PRISM Training and Consultancy Limited, UK).

All candidate tetravalent TDV formulations demonstrated minimal to no loss in virus potency for all serotypes after 39 weeks at 4° C. (FIGS. 14A-14D). Apparent increases in viral potency over time can be interpreted as zero loss given assay variability (based on in-house observations). Longitudinal time point virus titers were predicted by extrapolation from the best fit line at 78 weeks (2× the last real-time data point) (FIGS. 14A-14D) and demonstrated minimal loss in viral potency predicted over time. However, formulations containing dextran appeared to lose significant amounts of virus titer after lyophilization, compared to those with either HSA, making the total net loss in potency higher for the formulations containing dextran than HSA. These real-time data suggest that the identified and optimized candidate formulations exhibit the desired solid state stability profiles at the target storage temperature.

TABLE 16

The cake appearance of the lyophilized samples was assessed (FIG. 15A-15B) based on a visual rating system (1-3, where 1 is the worst and 3 is the best).

| Lyophilized formulation | Average Cake Appearance |
|---|---|
| Met + MSG + Ala + Urea + Mann | 3 |
| Met + MSG + Ala + Urea | 3 |
| MSG + Ala | 3 |
| Met + Urea | 3 |
| MSG + Urea | 3 |
| Ala + Urea | 3 |
| 15% Suc + 0.1% HSA | 3 |
| 10% Suc + 2.0% HSA | 3 |
| 10% Suc + 0.1% HSA | 3 |
| Met | 3 |
| MSG | 3 |
| Ala | 3 |
| Urea | 3 |
| Mann | 3 |
| Met + MSG + Ala | 3 |
| Met + MSG | 3 |
| Met + Ala | 3 |
| Arg | 3 |
| Arg + Urea | 3 |

In certain experiments, the effect of combining the lead excipients at the different concentrations on flavivirus (e.g. dengue serotype-3, TDV-3) titers before and after lyophilization and accelerated stability were evaluated. For these studies, HSA (at 0.1 and 0.2% w/v) was added to the base formulations described above because the results of the initial screen indicated HSA functioned as an effective lyoprotectant (FIG. 15). FIG. 15 demonstrates the results from screening of the effect of various excipient combinations (in a base buffer containing trehalose) on flavivirus (e.g. dengue serotype-3, TDV-3) viral potency. Base buffer contained 10% trehalose in 10 mM phosphate buffer with 30 mM NaCl, pH 7.2. Results indicate (FIG. 15A) flavivirus (e.g. dengue serotype-3, TDV-3) titer loss following lyophilization, (FIG. 15B) flavivirus (e.g. dengue serotype-3, TDV-3) titer loss after lyophilized samples were stored for 5 weeks at room temperature (~25° C.). Data are represented as mean values±s.d. Virus titers are given in log 10 pfu/ml.

As illustrated in FIG. 15, a <0.2 log loss of flavivirus (e.g. dengue serotype-3, TDV-3) titer post-lyophilization was observed at both HSA concentrations in base formulations containing either 10% sucrose or trehalose, respectively (FIG. 15A). Therefore, subsequent base buffer formulations were prepared containing phosphate buffer, NaCl, 10% sugar (trehalose or sucrose) with 0.1% HSA and indicated additional excipients. Most of the excipient combinations in either of these base formulations displayed improved virus stability in both post lyophilization and accelerated stability samples (FIGS. 15A-15B). Maximum lyoprotection was demonstrated by using a combination of amino acids and urea added in the base formulations. After 5 weeks at 25° C., either of the base formulations with mannitol and urea added, either with or without amino acids such as alanine, arginine, MSG and methionine demonstrated vastly improved viral stability (FIGS. 15A-15B). Increasing the sugar concentrations in the base formulations to 15% did not appear to provide any additional advantage in terms of protecting viral titers.

Preservation of virus potency in a live attenuated viral vaccine is vital for successful immunization across the shelf life of the product, which in turn, is largely dependent on the composition of the formulation and the type of final pharmaceutical dosage form (i.e., liquid vs lyophilized). Since lyophilization involves freezing and desiccation stresses, single excipients are often not sufficient for virus stabilization and hence a combination of additives is often required to protect against different degradation mechanisms. Sugars such as sucrose or trehalose, appeared to be very important in these lyophilized formulation for lyoprotection of the flavivirus titers and for other live virus vaccines. For example, trehalose in combination with gelatin was demonstrated to have better stabilization of a live-attenuated mumps vaccine compared to a combination of sucrose and sorbitol. Conversely, sucrose and lactalbumin afforded better thermal protection to a live, attenuated peste des petits ruminants (PPR) vaccine as opposed to trehalose alone.

In certain exemplary methods, the effect of both the sucrose and trehalose was systematically studied in combination with other excipients on the stability of flaviviruses (e.g. dengue serotype-3, TDV-3). Formulations containing urea, EDTA, polyols, proteins, polymers and amino acids displayed high virus recoveries post lyophilization with <0.2 log loss in flavivirus (e.g. dengue serotype-3, TDV-3) titer independent of sugar type (trehalose vs. sucrose). Among the studied excipients, viral potency losses were observed to be significant after lyophilization with formulations containing $MgCl_2$ and poloxamer 407 compared to other formulations. $MgCl_2$ is well known for its stabilization of poliovirus; however, the instant methods provide support of detrimental effects on flavivirus stability. Stabilizing effects of $MgCl_2$ may be virus dependent.

Once the lead excipients of these methods were identified, selected excipient combinations were tested on their ability to preserve flaviviruses (e.g. dengue serotype-3, TDV-3) potency. Formulations containing certain combinations of amino acids as well as urea displayed significant observable flavivirus lyoprotection, and when further combined with mannitol, imparted the highest virus potency stabilization after 25° C. storage for 5 weeks. While not wishing to be bound by any strict formulation, urea appears to have an important role in protecting flavivirus integrity/stability during dehydration. Addition of amino acids improved stability of various proteins in sucrose containing formulations during storage and could potentially play a role in stabilization via preferential hydration and/or increased solvent surface tension. Mannitol also demonstrated improved stabilizing effects on flaviviruses.

One approach adopted for formulation design of lyophilized live flavivirus vaccine candidates was a combination of semi-empirical experimentation and enhanced exploratory data analyses. The starting list of pharmaceutical excipients to examine for this work was reduced to 18 additives using scientific rationale based on literature review, pharmaceutical experience and considerations of the final target product profile (see Table 9). The empirical screening of excipient combinations generated a historical dataset that was interrogated by multivariate analyses and visualizations to generate exploratory graphs from initial models that guided selection of key excipients, their potential ranges, as well as excipient interactions in terms of their virus stabilization effects. Building an experimental dataset from the start instead of designing multivariate screening experiments, avoided adding excipients that had no effect and/or the use of inappropriate ranges for the excipients in a designed study.

Building an experimental virus stability dataset, performing an exploratory data analysis and retroactively fitting the data into 'initial' regression models is not without its limitations. This is why the models generated at this stage were described as exploratory (FIGS. 11A and 11B) in that they helped guide the statistically designed experiment likely to result in more reliable predictive models (DSD; Table 15). Historical datasets not statistically designed for precise, predictive modeling may contain non-essential data points, inconsistent response measurements, and/or incomplete measurement data for response parameters. These types of dataset artifacts are unlikely to contribute to accurate and reliable statistical models. This is illustrated by the low $R^2$ value for the model fit of login loss in titer after lyophilization (FIG. 11A). This may have been in part due to the difficulty in modeling the space between the two concentrations of HSA tested (0.1% and 2%), which contributed to artificially inflating the significance of the HSA*HSA interaction (FIG. 12A), thus identifying possible misleading curvilinear terms. Having a clear scientific understanding of the dataset imparts the ability to rationally utilize the exploratory data analysis and initial statistical models as guidance for selection of excipients and their concentrations.

Selection of the lead excipients and their potential working concentrations was essential to feed into and maximize the effectiveness of the predictive model derived from the designed experiment. Examination of the response data in the DSD screening models (FIG. 12C), and identifying the most desirable settings and ranges via the prediction profiler in JMP culminated in the creation of a contour plot (data not shown) capable of illustrating and mapping the design space of the optimal formulation for stabilization of lyophilized Flavivirus (e.g. dengue serotype-3, TDV-3). The DSD identified significant interactions between trehalose and HSA, found the stabilizing characteristics to be independent of alanine, and was able to confirm the optimal concentrations of mannitol and urea. The DSD model has good fits with high $R^2$ values that provided confidence in the reliability of the model allowing final selection of the lead formulation.

The models were authenticated as predictive and verified when the lead lyophilized formulation was prepared containing flaviviruses (e.g. a tetravalent mixture of TDV-1, -2, -3, and -4) and challenged at accelerated (25° C. for 5 weeks) and real time stability studies (4° C. for 39 weeks). As predicted by the DSD models, limited loss in virus potency after lyophilization and storage at 25° C. was found for Formulations 3 and 4. Despite elevated losses in potency after lyophilization for dextran containing formulations, all four formulations were predicted to maintain minimal to no loss of potency during storage in solid state for all serotypes at 4° C. for up to 78 weeks (2× the last stability time point), therefore, demonstrating that the candidate lyophilized formulations identified for stabilization of monovalent flaviviruses (e.g. dengue serotype-3, TDV-3) at 25° C. are stabilizing for all four dengue virus serotypes. Currently, many vaccine manufactures wish to replace human derived HSA with rHSA to avoid potential risks associated with human derived products. The substitution of dextran and rHSA for native HSA was an attempt to address this concern.

The instant study provides a case study of the efficiency with which a combined empirical screening and statistical modeling analysis can be used to identify and confirm the primary contributors (and their optimal concentrations) for stabilization and formulation development of candidate lyophilized live virus vaccines. This combined approach to formulation development of lyophilized live virus vaccines not only can save both money and time, but also enables building an enhanced viral stability data package that can support parallel process and formulation development efforts as well as submissions to regulatory agencies who recommend a Quality by Design approach to vaccine product development.

Materials and Methods

In one exemplary method, frozen dengue virus stock (e.g. TDV-3) stocks: ~$7.30\times10^7$ pfu/mL) (for example, in certain methods Lot no: DMV013-3 was used) in FTA buffer (1% Pluronic F127® (F) poloxamer 407, 15% Trehalose (T), and 0.1% HSA (A) in PBS buffer, pH 7.4) were stored at −80° C. Stocks were thawed in a 37° C. water bath and aliquoted (100 μL in 1.5 mL tubes). The aliquots were stored at −80° C. until use. In certain methods, aliquots can be frozen and thawed more than one time. For example, the thermal history of these aliquots equates to two freeze thaw cycles. Frozen dengue virus stocks were thawed and mixed by gentle vortexing. Samples were prepared in the following buffers: 10 mM Tris (pH 7.2), 10 mM histidine (pH 7.2), 10 mM HEPES (pH 7.2), 10 mM sodium phosphate (pH 7.2), all with and without 50 mM NaCl, as well as 10 mM phosphate with 137 mM NaCl (PBS). All excipients stock solutions were prepared in their respective buffers and the pH was adjusted to 7.2 or 7.4. To prepare certain virus formulations, virus stock was mixed with the formulation buffer to achieve a final virus concentration of approximately $2\times10^5$ pfu/mL.

In one example, six hundred and fifty micro-liters (650 μL) of each of the dengue virus formulations (e.g. tetravalent dengue formulations) were then aliquoted into 2 mL vials, and the vials were either lyophilized or stored at −80° C. as a pre-lyophylization control. A conservative lyophilization cycle was used to ensure that candidate formulations being evaluated were properly freeze-dried. All the samples were loaded in a pre-cooled device to −45° C. Thermocouples were placed in reference (e.g. FTA) control/placebo vials. Thermocouples were placed in following fashion within the shelf: one in the middle, one in the front, two in the back. Once the cycle was completed, the chamber was backfilled with nitrogen until chamber pressure reached 580 Torr and vials were fully stoppered. The chamber was allowed to reach atmospheric pressure (760 Torr). At this point, the release valve was opened and the tray containing the stoppered, lyophilized vials was removed. All vials were then sealed. The freeze-dried vials were then visually assessed and photographed with a digital camera (8-megapixel) to record the cake appearance and structure. The lyophilized virus formulations were then stored at −80° C.

All placebo and virus samples were prepared in a base buffer containing 10 mM sodium phosphate (pH 7.2) with 30 mM NaCl and 0.1% HSA. FTA was prepared in 10 mM PBS (phosphate buffered saline with 137 mM NaCl (pH 7.4). All excipients stock solutions were prepared in their respective buffers and the pH was adjusted to about 7.0 to about 8.0 or about 7.2 to about 7.4. Both pre and post lyophilized virus samples were evaluated for potency using a microtiter IFA assay. Stability studies for selected virus and lyophilized formulations were performed at about room temperature (e.g. 25° C.) (four vials) for five weeks. Samples stored at −80° C. (four vials) for five weeks were used as controls.

In another example, frozen dengue virus stocks (e.g. TDV-1, TDV-2, and TDV-4 virus) in phosphate buffer, 15% Trehalose, 1% poloxamer 407 (F127®) and 0.1% HSA—were supplied and stored frozen at −80° C. until further use. Sucrose and trehalose were purchased from Pfanstiehl Laboratories (Waukegan, Illinois). L-Arginine, methionine, sodium L-glutamate, EDTA, dextran 40, magnesium chloride, mannitol, sorbitol, gelatin were purchased from Sigma Aldrich (St. Louis, Missouri). poloxamer 407 (F127®) sample was received from BASF. Salts for preparing buffers, polysorbate 80, urea were purchased from Fisher Scientific and Acros. Human serum albumin was purchased from Octapharma and Recombinant HSA (rHSA) was obtained from Novazymes.

In other examples, virus titers were determined by plaque assay using a 96-well microtiter method. Briefly, an adherent Vero cell monolayer was infected with dilutions of either monovalent or tetravalent virus, followed by the addition of a viscous overlay. Plates were then incubated at 37° C. for 2 or 3 days depending on serotype, then washed and fixed for staining. Staining was performed using serotype-specific monoclonal antibodies. The assay has a working variable range of ±0.34, 0.17, 0.19, and 0.19 log 10 pfu/0.5 mL (dose) for serotypes 1 through 4, respectively as determined by trending control analysis. Each sample was measured in triplicate and the results were reported as an average of the values.

Virus formulation and Lyophilization. Bulk solutions of each excipient were prepared in phosphate buffer containing 30 mM NaCl and the pH was adjusted to 7.2. Desired amounts of excipients were mixed with phosphate buffer with 30 mM NaCl to obtain the final concentrations and then appropriate amount of the virus stock was added to achieve $2\times10^5$ pfu/ml. All viral preparation work was carried out in a class II biosafety cabinet (Labconco, Kansas City, MO).

In certain methods, about 650 μl of viral vaccine formulations were dispensed in sterile 2 mL vials and partially sealed with sterile rubber stoppers. A conservative lyophilization cycle with the process ramping the temperature from −45 to 25° C. at a pressure of 50 mTorr over the course of over 2 days was used to produce lyophilized formulations. Samples were loaded in a FTS Lyo Star II (SP Scientific) that had pre-cooled shelves set to −45° C. Following a freeze step at −45° C. for 2 h and a ramp down to reduced pressure of 50 mTorr (about 2 hr.), the temperature was increased to −37° C. with ramp rate of 0.1° C./min. At the end of primary drying, temperature ramped up to 25° C. with ramp rate of 0.1° C./min and continued drying for 6 hr. Following completion of secondary drying, shelf was cooled to 4° C. and held at 4° C. until the cycle was completed (see Table 2 for more details). Upon cycle completion, vials were backfilled with nitrogen and stoppered under vacuum (580,000 Torr) prior to being removed from the chamber, and then tightly sealed with aluminum seals. The lyophilization cycle was monitored by placing thermocouples in the bottom center of at least three placebo vials per batch and using comparative pressure measurement (pirani vs. capacitance manometer).

Thermo stability testing of lyophilized virus formulations. Selected lyophilized vaccine formulations were stored at 4° C. in refrigerator and at 25° C. in a stability chamber. After indicated lengths of time, vials were sampled and rehydrated with 0.5 ml of sterile water for injection. Viral infectivity of the reconstituted vaccine was assessed using microtiter assay. To evaluate virus stability following lyophilization, infectious potency of rehydrated vaccine was determined by microtiter assay. Loss in virus titer following lyophilization was calculated by subtracting the titer of lyophilized virus samples stored at −80° C. from the initial titer (the frozen liquid control sample stored at −80° C.). Similarly, the loss of virus potency during real time and accelerated storage was determined by comparing the viral infectivity of the incubated samples with the infectivity of post lyophilization samples that were stored at −80° C. Errors for losses were calculated by propagation of error method using following equation $SE(C)-\sqrt{SE(A)^2+SE(B)^2}$. For each condition, samples were titrated in triplicate and average login titer was calculated.

Statistical Analysis. Response Surface methods were fit using stepwise regression tools and the Definitive Screening Design was generated using the Design of Experiments platform available in JMP profiler v11.2.0 (JMP Corporation, Cary, NC).

Pharmaceutical Cake Quality Determination. Lyophilized cakes were rated on a subjective scale from 1 to 3, where 1=bad, 2=fair, and 3=good. Cakes with a rating of 1 were distinguished as having extensive structural collapse, meltback on the bottom and sides, significant shrinkage and retraction from all sides, and/or appearance of granules. Cakes with a rating of 2 had partial shrinkage and retraction from the sides, moderate meltback on the bottom, and/or large cracks or fissures running through the cake horizontally or vertically. Cakes with a rating of 3 were pharmaceutically elegant, appearing as compact, (mostly white, excipient combination depending) cake structures with generally flat surfaces and no or minimal shrinkage or retraction of the cake from the top of the cake or sides of the vial.

Abbreviations

CM: Capacitance manometer
DOE: Design of experiment
HSA: Human serum albumin
HEPES: 2-[4-(2-hydroxyethyl) piperazin-1-yl]ethanesulfonic acid
IFA: Immunofocus Assay
MSG: Monosodium glutamate
NaCl: Sodium chloride
PBS: Phosphate buffered saline
rHSA: Recombinant human serum albumin
THAM/Tris: Tris (hydroxymethyl) aminomethane
Pfu: Plaque forming unit
PF127: Pluronic F-127®, poloxamer 407

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A lyophilized dengue virus composition comprising:
live, attenuated dengue virus;
at least one of trehalose and sucrose;
urea;
a protein agent comprising human serum albumin (HSA);
arginine; and
at least one salt comprising sodium chloride (NaCl), sodium phosphate ($Na_2HPO_4$), potassium chloride (KCl) or potassium phosphate ($KH_2PO_4$);
wherein the composition stabilizes the live, attenuated dengue virus.

2. The lyophilized dengue virus composition according to claim 1, wherein the composition further comprises a base buffer, the base buffer comprises phosphate buffered saline (PBS), HEPES buffer, histidine buffer or Tris buffer.

3. The lyophilized dengue virus composition according to claim 1, wherein the composition is configured to be partially or wholly rehydrated prior to administration of the composition to a subject as part of an immunogenic composition.

4. The lyophilized dengue virus composition according to claim 1, wherein the at least one salt comprises NaCl at a concentration of 10 mM to 200 mM.

5. The lyophilized dengue virus composition according to claim 1, further comprising mannitol.

6. The lyophilized dengue virus composition according to claim 1 further comprising, one or more amino acids or derivatives thereof or salts, esters or amide derivatives thereof.

7. The lyophilized dengue virus composition according to claim 6, wherein the one or more amino acids or derivatives thereof or salts, esters or amide derivatives thereof comprises methionine, arginine, alanine or a combination thereof.

8. The lyophilized dengue virus composition according to claim 6, wherein the one or more amino acids or derivatives thereof or salts, esters or amide derivatives thereof comprises monosodium glutamate (MSG).

9. The lyophilized dengue virus composition according to claim 1, wherein the protein agent further comprises dextran, polyol polymer or gelatin.

10. The lyophilized dengue virus composition according to claim 1, wherein the dengue virus comprises four dengue serotypes in the form of a dengue 1/2 chimera, a modified live attenuated dengue-2 virus, a dengue 3/2 chimera, and a dengue 4/2 chimera, wherein the dengue-2 virus as the backbone of the dengue 1/2 chimera, the dengue 3/2 chimera and the dengue 4/2 chimera is a PDK-53 dengue-2 strain.

11. The lyophilized dengue virus composition according to claim 1 wherein the composition does not contain magnesium chloride ($MgCl_2$).

12. The lyophilized dengue virus composition according to claim 1, wherein the protein agent is present in the composition at a concentration ranging from 0.05% to 1.0% (w/v).

13. The lyophilized dengue virus composition according to claim 1, wherein the trehalose and sucrose or combination of trehalose and sucrose is present in the composition at a concentration ranging from 0.5% to 15.0% (w/v).

14. The lyophilized dengue virus composition according to claim 6, wherein the one or more amino acids or derivatives thereof or salts, esters or amide derivatives is present in the composition at a concentration ranging from 1.0 mM to 25.0 mM.

15. The lyophilized dengue virus composition according to claim 1, wherein the urea concentration in the composition is from 0.01% to 1.0% (w/v).

16. The lyophilized dengue virus composition according claim 1, wherein at least one of the trehalose, sucrose and a combination of trehalose and sucrose is present in the composition at a concentration ranging from 0.5% to 15.0% (w/v), the urea concentration in the composition is from 0.01% to 1.0% (w/v), and the protein agent concentration in the composition is from 0.05% to 1.0% (w/v).

17. The lyophilized dengue virus composition according to claim 1, wherein the HSA concentration is from 0.05% to 0.5% (w/v); wherein the sucrose, trehalose or combination of sucrose and trehalose concentration is from 0.5% to 15.0% (w/v); wherein the arginine concentration is from 1.0 mM to about 20.0 mM; and wherein the urea concentration is from 0.1% to 0.3% (w/v).

18. The lyophilized dengue virus composition according to claim 17, wherein at least one of the sucrose, trehalose, and combination of sucrose and trehalose is present in the composition at a concentration ranging from 5.0% to 15.5% (w/v).

19. The lyophilized dengue virus composition according to claim 1, wherein the wherein the trehalose, sucrose, or combination of trehalose and sucrose is present in the composition at a concentration of less than 10.0% (w/v).

20. A method for stabilizing live, attenuated dengue virus, the method comprising:

combining live, attenuated dengue virus with a composition comprising:

at least one of trehalose and sucrose;

urea;

human serum albumin (HSA);

arginine; and at least one salt comprising sodium chloride (NaCl), sodium phosphate ($Na_2HPO_4$), potassium chloride (KCl) or potassium phosphate ($KH_2PO_4$); and lyophilizing the dengue virus composition, wherein the composition stabilizes the live, attenuated dengue virus.

21. The method according to claim 20, wherein the live flaviviruses comprises live, attenuated dengue virus comprises four dengue virus serotypes in the form of a dengue 1/2 chimera, a modified live, attenuated dengue-2 virus, a dengue 3/2 chimera, and a dengue 4/2 chimera, wherein the dengue-2 virus as the backbone of the dengue 1/2 chimera, the dengue 3/2 chimera and the dengue 4/2 chimera is a PDK-53 dengue-2 strain.

22. The method according to claim 20, wherein the lyophilized flavivirus dengue virus composition is stored at 25° C. for extended periods.

23. The method according to claim 20, further comprising partially or wholly rehydrating the composition prior to administration of the composition to a subject as part of an immunogenic composition.

24. The method according to claim 20, wherein the composition further comprises a buffer.

25. The method according to claim 20, wherein the composition further comprises one or more protein agents selected from the group consisting of gelatin, dextran, a polyol polymer, or combinations thereof.

26. The method according to claim 20, wherein the composition further comprises one or more amino acids or derivatives thereof or salts, esters or amide derivatives thereof.

27. The method according to claim 26, wherein the one or more amino acids or derivatives thereof or salts, esters or amide derivatives thereof are selected from the group consisting of alanine, methionine, MSG or combinations thereof.

28. The method according to claim 20, wherein the urea is present in the composition at a concentration ranging from 0.01% to 0.5% (w/v).

29. A kit for stabilizing live, attenuated dengue virus comprising:

a composition according to claim 1; and at least one container.

* * * * *